(12) United States Patent
Voskuhl

(10) Patent No.: US 10,758,496 B2
(45) Date of Patent: *Sep. 1, 2020

(54) ESTROGEN RECEPTOR LIGAND TREATMENT FOR NEURODEGENERATIVE DISEASES

(71) Applicant: The Regents of the University of California, Oakland, CA (US)

(72) Inventor: Rhonda R. Voskuhl, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 10 days.

This patent is subject to a terminal disclaimer.

(21) Appl. No.: 15/507,881

(22) PCT Filed: Sep. 1, 2015

(86) PCT No.: PCT/US2015/047909
§ 371 (c)(1),
(2) Date: Mar. 1, 2017

(87) PCT Pub. No.: WO2016/036721
PCT Pub. Date: Mar. 10, 2016

(65) Prior Publication Data
US 2017/0304216 A1    Oct. 26, 2017

Related U.S. Application Data

(60) Provisional application No. 62/047,285, filed on Sep. 8, 2014, provisional application No. 62/044,679, filed on Sep. 2, 2014.

(51) Int. Cl.
| | |
|---|---|
| *A61K 31/05* | (2006.01) |
| *C07D 307/93* | (2006.01) |
| *C07D 487/04* | (2006.01) |
| *C07D 307/82* | (2006.01) |
| *A61K 31/137* | (2006.01) |
| *A61K 31/225* | (2006.01) |
| *C07C 39/42* | (2006.01) |
| *A61K 38/13* | (2006.01) |
| *A61K 38/21* | (2006.01) |
| *A61K 45/06* | (2006.01) |

(52) U.S. Cl.
CPC ............ *A61K 31/05* (2013.01); *A61K 31/137* (2013.01); *A61K 31/225* (2013.01); *A61K 38/13* (2013.01); *A61K 38/21* (2013.01); *A61K 45/06* (2013.01); *C07C 39/42* (2013.01); *C07D 307/82* (2013.01); *C07D 307/93* (2013.01); *C07D 487/04* (2013.01); *A61K 2300/00* (2013.01); *C07C 2601/06* (2017.05)

(58) Field of Classification Search
None
See application file for complete search history.

(56) References Cited

U.S. PATENT DOCUMENTS

| | | | | |
|---|---|---|---|---|
| 6,936,599 B2 * | 8/2005 | Voskuhl | ................. | A61K 31/56 514/16.6 |
| 8,372,826 B2 | 2/2013 | Voskuhl | | |
| 8,658,627 B2 | 2/2014 | Voskuhl | | |
| 8,895,539 B2 | 11/2014 | Voskuhl | | |
| 9,168,262 B2 | 10/2015 | Voskuhl | | |
| 9,452,175 B2 | 9/2016 | Voskuhl | | |
| 2012/0282222 A9 * | 11/2012 | Voskuhl | ............... | A61K 31/277 424/85.6 |
| 2013/0203722 A1 * | 8/2013 | Voskuhl | ............... | A61K 31/565 514/182 |

FOREIGN PATENT DOCUMENTS

| | | | | |
|---|---|---|---|---|
| WO | WO-2002/085374 | | 10/2002 | |
| WO | WO 2006/065968 | * | 6/2006 | ......... A61K 31/4184 |
| WO | WO-2006/065968 A2 | | 6/2006 | |
| WO | WO-2007/038435 A2 | | 4/2007 | |
| WO | WO-2007/038636 A2 | | 4/2007 | |
| WO | WO-2008150547 A1 | | 12/2008 | |
| WO | WO-2010/050916 A1 | | 5/2010 | |
| WO | WO-2013/017619 A1 | | 2/2013 | |

OTHER PUBLICATIONS

Vickers, Drugs Aging, 2002, 19: 487-494 (Year: 2002).*
Lanka and Cudkowicz, Amyotrophic Lateral Sclerosis, 2008; 9: 131-140 (Year: 2008).*
Webpage from https://www.mayoclinic.org/diseases-conditions/huntingtons-disease/symptoms-causes/syc-20356117?p=1 (4 pages total; downloaded Oct. 14, 2018. (Year: 2018).*
Bendfeldt et al., Brain Research, 2010; 1325: 174-182 (Year: 2010).*
Zivadinov et al., Multiple Sclerosis 2007; 13: 490-501 (Year: 2007).*
Geurts et al. (Lancet Neurol., 2012; 11: 1082-92. (Year: 2012).*
Tiwari-Woodruff and Voskuhl (Journal of the Neurological Sciences, 2009; 286: 81-85 (Year: 2009).*
Fisher et al., "Gray Matter Atrophy in Multiple Sclerosis: A Longitudinal Study," Ann Neurol, 64(3): 255-265 (2008).
International Search Report of the International Searching Authority, dated Dec. 30, 2015, from related International Application No. PCT/US2015/047909.
International Search Report of the International Searching Authority, dated Nov. 30, 2016, from related International Application No. PCT/US2016/047485.
Mackenzie-Graham et al., "Estrogen Treatment Prevents Gray Matter Atrophy in Experimental Autoimmune Encephalomyelitis," J Neurosci Res, 90(7): 1310-1323 (2012).
Tiwari-Woodruff et al., "Differential Neuroprotective and Antiinflammatory Effects of Estrogen Receptor (ER) and ER Ligand Treatment," P Natl Acad Sci USA, 104(37): 14813-14818 (2007).

(Continued)

*Primary Examiner* — Christina M Borgeest
(74) *Attorney, Agent, or Firm* — Foley Hoag LLP; David P. Halstead; Alexander J. Chatterley

(57) ABSTRACT

The present invention relates to treatment of neurological diseases such as multiple sclerosis (MS) and Alzheimer's disease, using an estrogen receptor beta (ERβ) ligand.

20 Claims, 26 Drawing Sheets

(56) References Cited

OTHER PUBLICATIONS

Wisdom et al., "Estrogen Receptor-beta Ligand Treatment After Disease Onset is Neuroprotective in the Multiple Sclerosis Model," J Neurosci Res, 91(7): 901-908 (2013).

Extended European Search Report issued by the European Patent Office in corresponding Application No. 15837267.2, dated Feb. 8, 2018.

George et al., "Nonsteroidal selective androgen receptor modulators and selective estrogen receptor β agonists moderate cognitive deficits and amyloid-β levels in a mouse model of Alzheimer's disease," ACS Chem Neurosci, 4(12):1537-1548 (2013).

McFarland et al., "AC-186, a selective nonsteroidal estrogen receptor β agonist, shows gender specific neuroprotection in a Parkinson's disease rat model," ACS Chem Neurosci, 4(9):1249-1255 (2013).

Hart el al., "Modelling of multiple sclerosis: lessons learned in a non-human primate," The Lancet Neurology, 3(10):588-597 (2004).

Itoh et al., "Bedside to bench to bedside research: Estrogen receptor beta ligand as a candidate neuroprotective treatment for multiple sclerosis," Journal of Neuroimmunology, 304:63-71 (2017).

Lund et al., "Novel actions of estrogen receptor-β on anxiety-related behaviors," Endocrinology, 146:797-807 (2005).

Wekerle et al., "Animal models of multiple sclerosis," Drug Discovery Today: Disease Models, 3(4):359-367 (2006).

Chard et al., "What lies beneath grey matter atrophy in multiple sclerosis?" Brain: J Neurol 139(1):7-10 (2016).

Croxford et al., "Mouse models for multiple sclerosis: Historical facts and future implications," Biochimica Biophysica Acta, 1812:177-83 (2011).

Elloso et al., "Suppression of experimental autoimmune encephalomyelitis using estrogen receptor-selective ligands," J Endocrinol, 185:243-52 (2005).

Gold et al., "Understanding pathogenesis and therapy of multiple sclerosis via animal models: 70 years of merits and culprits in experimental autoimmune ecephalomyelitis research," Brain, 129:1953-1971 (2006).

Karim et al., "Increase in chemokine CXCL1 by Erβ ligand treatment is a key mediator in promoting axon myelination," PNAS, 115(24):6291-6296 (2018).

Ranshohoff, "Animal models of multiple sclerosis: the good, the bad and the bottom line," Nature Neuroscience, 15(8):1074-1077 (2012).

Singhal et al., "The Effect of Glatiramer Acetate on Spinal Cord Volume in Relapsing-Remitting Multiple Sclerosis," J Neuroimaging 27(1):33-36 (2017).

* cited by examiner

Top panel: cerebral gray matter neuropathology

Bottom panel: cerebellar gray matter neuropathology

ESTROGEN RECEPTOR LIGAND TREATMENT FOR NEURODEGENERATIVE DISEASES

PRIORITY CLAIM

This application is a § 371 national-stage application based on PCT Application PCT/US15/047909, filed Sep. 1, 2015, which claims priority to U.S. Provisional Patent Application No. 62/044,679, filed on Sep. 2, 2014, and U.S. Provisional Patent Application No. 62/047,285, filed on Sep. 8, 2014, each of which is hereby incorporated by reference in its entirety.

BACKGROUND

This invention relates generally to a novel treatment to prevent neurodegeneration in the central nervous system due to diseases such as multiple sclerosis (MS), Alzheimer's disease, Parkinson's disease, spinal cord injury, stroke, etc. More specifically, some embodiments of the present invention relates to a treatment comprising a combination of an estrogen receptor ligand with a secondary agent, such as an immunotherapeutic compound.

GENERAL BACKGROUND

There are no neuroprotective drugs that can be taken for long durations of time without significant side effects. Estrogens, as well as the use of estrogen receptor (ER) alpha ligand treatments, have been studied in disease and injury models and in humans. Estrogen, and estrogen receptor alpha ligand treatments, are effective in some disease and injury models. For example, they are both anti-inflammatory and neuroprotective in experimental autoimmune encephalomyelitis (EAE), the animal model for multiple sclerosis (MS) and there is a dose response whereby higher levels are more protective. However, in humans, treatment with estrogens or ER alpha ligands may not be tolerable due to the induction of breast cancer and uterine cancer, which are mediated by estrogen receptor alpha in the breast and uterus, respectively. One must always consider the risk:benefit ratio of any estrogen treatment when considering its use in neurodegenerative diseases. Estrogens in the form of hormone replacement therapy have been associated with side effects and therefore are controversial with respect to whether they are recommended for use in a subset of healthy menopausal women, depending on their menopausal symptoms and other disease risk factors. While the risk:benefit ratio in debilitating neurodegenerative diseases is clearly different than the risk:benefit ratio in healthy individuals, optimizing efficacy and minimizing toxicity, remains the goal. Hence, determining which estrogen receptor mediates the neuroprotective effect of estrogen treatment is of central importance.

In contrast, estrogen receptor beta (ERβ) is not associated with breast or uterine cancer. Thus, estrogen receptor beta ligands may be used for long durations and/or for patients with some risk factors for breast and uterine cancer who could not otherwise tolerate estrogen or estrogen receptor alpha ligand treatment.

One estrogen, estradiol, and estrogen receptor alpha ligands agonist have been shown to be both anti-inflammatory and neuroprotective in the EAE model. They ameliorate EAE symptomology immediately after the disease is induced. In contrast, estrogen receptor beta ligand treatment is not anti-inflammatory, but has been shown for the first time to be neuroprotective. This mechanism is thought to explain why ER beta ligand treatment does not work at EAE onset, but does work later to promote recovery or delay EAE progression.

There are currently no purely neuroprotective treatments for MS. Thus, for diseases such as MS, which have both an inflammatory and a neurodegenerative component, estrogen receptor beta ligands may be useful. For diseases that do not appear to have an inflammatory component, but only a neurodegenerative component, then the estrogen receptor beta ligand treatment may also be useful. Notably, Alzheimer's disease, Parkinson's disease, brain or spinal cord injury and stroke are primarily purely neurodegenerative diseases or injuries, but there may be a minor inflammatory component. To date, for Alzheimer's disease, for example, there are only treatments that can be used in short term duration. Hence, the identification of an alternative neuroprotective agent represents an important advance in preclinical drug development in MS and other chronic neurodegenerative diseases or injuries.

SUMMARY

The present invention is directed to a treatment for neurodegeneration in the central nervous system due to diseases such as MS, Parkinson's disease, cerebellar ataxia, Down's Syndrome, epilepsy, strokes, Alzheimer's disease, as well as brain and/or spinal cord (CNS) injury.

In accordance with some embodiments of the present invention, a method for treating the symptoms of a neurodegenerative disease or CNS injury in a mammal is provided, the method comprising the steps of administering to the mammal a primary agent being an estrogen receptor ligand, and optionally, a secondary agent, such as an immunotherapeutic compound. In one embodiment, the estrogen receptor ligand may be an ERβ ligand, such as AC-186 (Compound I) or a compound substantially similar in chemical structure and/or activity thereto (such as those compounds disclosed in PCT Patent Publication WO 2013/017619 A1, incorporated by reference herein).

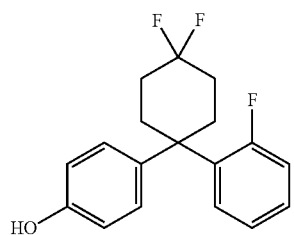

I

In some embodiments, the estrogen receptor beta ligand is a compound selected from the compounds disclosed in U.S. Patent Application Publications 2012/0202861 A1 or 2013/0131061 A1 (incorporated herein by reference). In some embodiments, the estrogen receptor beta ligand is KBRV1 or KBRV2 (Karo Bio, Huddinge, Sweden).

In accordance with other embodiments of the present invention, the invention comprises the use of a primary agent comprising an estrogen receptor beta ligand for a neuroprotective effect. In certain embodiments an ERβ ligand may be used to prevent and/or delay the onset or progression of disease or injury after the acute phase and/or ameliorate clinical symptoms of neurodegenerative diseases or injury, including multiple sclerosis. In one embodiment, a secondary agent, including an immunotherapeutic or anti-inflammatory compound could be used. In certain embodiments, the secondary agent is an immunotherapeutic agent, and the amount of the immunotherapeutic agent administered in combination with the estrogen receptor beta ligand is less than a therapeutically effective amount when the immunotherapeutic agent is administered alone.

In accordance with some embodiments the present invention relates to use of at least one primary therapeutically active agent, the primary therapeutically active agent being an estrogen receptor beta ligand, optionally in combination with a secondary active agent for the manufacture of a medicament for the therapeutic treatment of a neurodegenerative disease in a mammal.

The above described and many other features and attendant advantages of the present invention will become apparent from a consideration of the following detailed description when considered in conjunction with the accompanying drawings.

BRIEF DESCRIPTION OF THE DRAWINGS

FIG. 8 EAE scores in a different chronic progressive EAE model in NOD females. EAE scores for NOD females under various treatment conditions. Animals receiving an estrogen receptor β ligand (either AC-186 at 30 mg/kg, AC-186 at 10 mg/kg, or DPN) in a miglyol vehicle each displayed better EAE scores than animals receiving vehicle alone. In contrast, no protection was observed using the sesame oil carrier, even with a high dose AC-186 treatment.

FIG. 14 consists of two panels, labeled panels (A) and (B). (Panel A, top row) Representative 10× captures of spinal cord sections at the dorsal column of matched healthy control (left), vehicle-treated EAE (2nd from left), AC-186 10 mg/kg post-treated EAE (3rd from left), and AC-186 30 mg/kg post-treated EAE (right). EAE mice were sacrificed at EAE day 60. Axons and myelin were stained with NF200 and MBP, respectively (Panel A, top three rows). Representative 10× confocal images of spinal cord sections were stained for axonal damage using beta-APP (A, bottom row). (Panel B) Quantification of axonal densities (left), beta-APP expression (middle), and myelin staining intensity (right). Vehicle treated EAE (Veh) as compared to matched healthy controls (Cont) showed significantly reduced axon numbers (left), increased beta-APP (middle) and reduced myelin (right). AC-186 10 mg/kg, and 30 mg/kg treated EAE groups each showed significantly more axon numbers compared with the Vehicle treated EAE group (p<0.03, Veh vs AC-186 10 mg/kg and Veh vs AC-186 30 mg/kg). The beta-APP staining showed that the AC-186 30 mg/kg treatment group had significantly less expression of beta-APP compared with the Vehicle treated EAE group (p=0.0296, Veh vs AC-186 30 mg/kg). The AC-186 10 mg/kg treatment group showed a trend of less beta-APP staining compared with the Vehicle treated EAE group, but the difference with this dose did not reach significance. MBP staining showed that both AC-186 treatment groups had a trend for somewhat higher MBP staining intensity as compared to vehicle but this did not reach statistical significance. Four mice in each treatment group were examined for each treatment group. p-values were determined by one-way ANOVA.

FIG. 15 consists of two panels, labeled panels (A) and (B). (Panel A, top row) Representative 10× captures of spinal cord sections at the dorsal column of matched healthy controls (left), vehicle-treated EAE (2nd from left), AC-186 10 mg/kg post-treated EAE (3rd from left), and AC-186 30 mg/kg post-treated EAE (right). EAE mice were sacrificed at EAE day 60. Immune cells in the CNS were stained with pan-leucocyte marker CD45. The tissues were counterstained by DAPI. (Panel A, middle row) Representative 10× confocal images of spinal cord sections stained with Iba-1. (Panel A, bottom row) Representative 10× confocal images of spinal cord sections stained with CD3. (Panel B) Quantification of CD45 immunoreactivity (left), Iba-1 globoid cells to quantify macrophage like cells (middle), and CD3 to quantify T lymphocytes (right) as shown in (Panel A). Vehicle treated EAE (Veh) as compared to matched healthy controls (Cont) showed significantly increased CD45 staining (left), increased Iba-1 globoid cells (middle), and increased CD3 cells (right). AC-186 10 mg/kg and 30 mg/kg post-treatment EAE groups each showed a reduction of CD45 expression compared with the Vehicle treated EAE group (p=0.001, Veh vs AC-186 10 mg/kg, p=0.005, Veh vs AC-186 30 mg/kg). Each of the AC-186 treatment groups also showed a significant reduction in the number of Iba-1 stained cells with globoid morphology as compared with the Vehicle treated EAE group (p<0.0001, Veh vs AC-186 10 mg/kg, p=0.0001, Veh vs AC-186 30 mg/kg). There were no differences in the number of CD3 stained cells between either of the AC-186 treatment groups as compared to the Vehicle EAE treatment group. Four mice in each treatment group (or three mice for Veh and AC-186 10 mg/kg groups in CD45 staining) were examined for each treatment group. p-values were determined by one-way ANOVA.

FIG. 17 consists of three panels, labeled panels (A), (B), and (C). (Panel A) A graph of the mean whole brain volume in healthy controls ("X"), AC-186-treated mice with EAE ("O"), and vehicle-treated mice with EAE ("■") at d0, d30 and d60. AC-186-treated EAE mice exhibit less brain atrophy than vehicle-treated EAE mice as early as d30. (Panel B) A graph of the mean cerebral cortex volume in healthy controls, AC-186-treated mice with EAE and vehicle-treated mice with EAE at d0, d30 and d60. AC-186-treated EAE mice exhibit less atrophy in the cerebral cortex than vehicle-treated EAE mice by d60. (Panel C) A graph of the mean cerebellar volume in healthy controls, AC-186-treated mice with EAE and vehicle-treated mice with EAE at d0, d30 and d60. AC-186-treated EAE mice exhibit less cerebellar atrophy than vehicle-treated EAE mice by d60.

DETAILED DESCRIPTION

Figure 1:
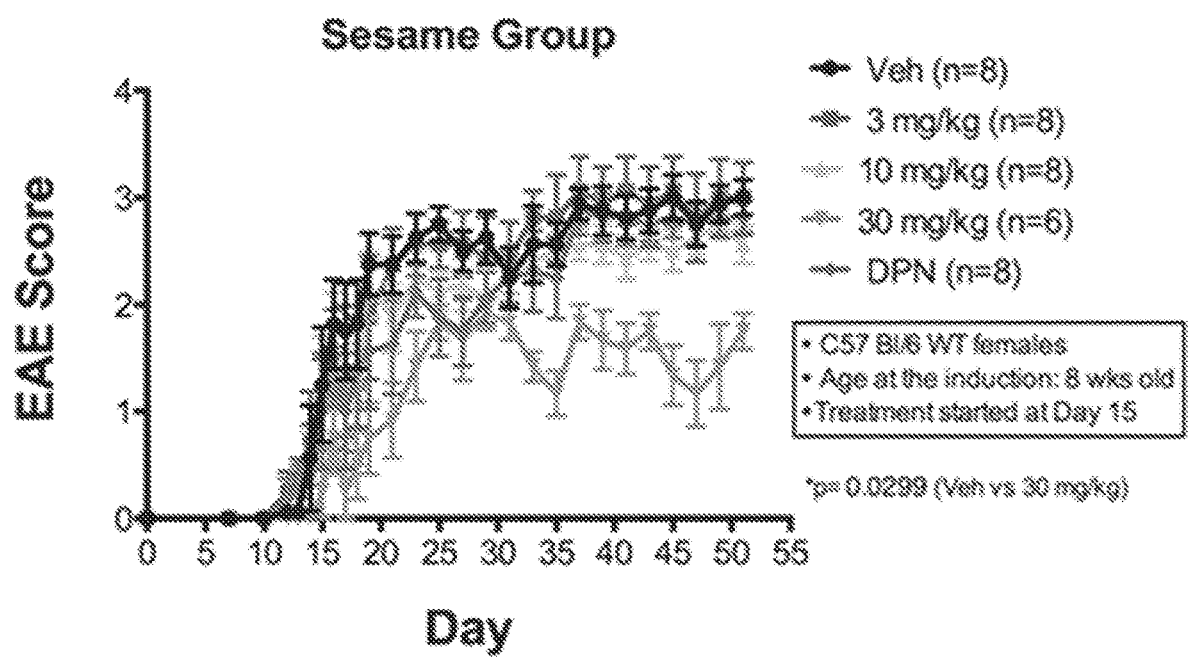
FIG. 1. EAE scores versus time for all treatment groups in female C57BL/6 mice. The group receiving 30 mg/kg of AC-186 ("▼") displayed the best EAE score. Treatment with DPN was not effective when sesame oil was the carrier. This loss of effect of DPN with sesame oil as the carrier suggests that the carrier is important since previous work had shown that DPN ameliorated EAE when provided in a different carrier (Miglyol). Despite using the sesame carrier, some effectiveness was observed for AC-186 at the highest dose (30 mg/kg).

This description is not to be taken in a limiting sense, but is made merely for the purpose of illustrating the general principles of the invention. The section titles and overall organization of the present detailed description are for the purpose of convenience only and are not intended to limit the present invention.

Definitions

As used herein the specification, "a" or "an" may mean one or more. As used herein in the claim(s), when used in conjunction with the word "comprising", the words "a" or "an" may mean one or more than one. As used herein "another" may mean at least a second or more.

The term "preventing" is art-recognized, and when used in relation to a condition, such as a neurodegenerative disease, is well understood in the art, and includes administration of a composition which reduces the frequency or severity of the symptoms of a medical condition in a subject relative to a subject who does not receive the composition. Thus, the prevention of neurodegenerative disease progression includes, for example, reducing the average amount of gray matter loss in a population of patients receiving an estrogen receptor beta ligand relative to a control population that did not receive the estrogen receptor beta ligand e.g., by a statistically and/or clinically significant amount. Similarly, the prevention of neurodegenerative disease progression includes reducing the likelihood that a patient receiving an estrogen receptor beta ligand will develop as much gray matter loss as the patient would develop if the patient did not receive the estrogen receptor beta ligand. Similarly, the prevention of neurodegenerative disease progression includes reducing the likelihood that a patient receiving an estrogen receptor beta ligand will develop a disability, such as cognitive decline, learning disability, and/or memory loss, as much as the patient would develop if the patient did not receive the estrogen receptor beta ligand.

The term "subject" as used herein refers to a living mammal and may be interchangeably used with the term "patient". In certain embodiments, the subject is a rodent, such as a mouse, or a primate, such as a human. The subject may be a male or female. In some embodiments, the subject is a female.

The terms "substantial brain gray matter atrophy" and "substantial loss of brain gray matter volume" as used herein, refers to a patient having greater than about 0.5% brain gray matter loss per annum (e.g., about 0.5%, or about 0.6%, or about 0.7%, or about 0.8%, or about 0.9%, or about 1.0%, or about 1.1%, or about 1.2%, or about 1.3%, or about 1.4%, or about 1.5%, or about 2.0% brain gray matter loss per annum). For example, "substantial brain gray matter atrophy" and "substantial loss of brain gray matter volume" may refer to a patient having a loss of brain gray matter of greater than about 0.3% in a period of at least about 6 months (e.g., about 0.4%, or about 0.5%, or about 0.6%, or about 0.7%, or about 0.8%, or about 0.9%, or about 1.0%, or about 1.1%, or about 1.2%, or about 1.3%, or about 1.4%, or about 1.5%, or about 2.0 in a period of about 6 months, or about 12 months, or about 18 months, or about 24 months). The amount of gray matter loss may be determined, for example, by using an imaging technique or surrogate marker.

As used herein, the term "treating" or "treatment" includes reducing, arresting, or reversing the symptoms, clinical signs, or underlying pathology of a condition in a manner to stabilize or improve a subject's condition or to prevent the likelihood that the subject's condition will worsened as much as if the subject did not receive the treatment.

Generally, the invention involves a method of treating a mammal exhibiting neurodegeneration, such as clinical symptoms of an autoimmune or neurodegenerative disease, comprising administering a primary agent being an estrogen receptor ligand. In one embodiment, the estrogen receptor ligand is an ERβ ligand. Optionally, a secondary agent may be used to treat neurodegeneration, preferably in a lower dose than if not used in combination with an estrogen receptor ligand. The treatment is aimed at providing a protective effect after the acute phase, reducing the number and/or degree of signs and symptomology and/or progression of a neurodegenerative disease.

The beneficial effect of treatment can be evidenced by a protective effect on the progression of disease symptomology after the acute phase, a reduction in the number and/or severity of some or all of the clinical signs and/or symptoms, or an improvement in the overall health.

For example, patients who have clinical symptoms of a neurodegenerative disease often suffer from some or all of the following symptoms: worsening of pre-existing symptoms (memory loss in Alzheimer's disease), the appearance of new symptoms (e.g., balance problems in Parkinson's disease) or increased generalized weakness and fatigue. MS patients in particular suffer from the following symptoms: weakness, numbness, tingling, loss of vision, memory difficulty, learning disability, and extreme fatigue. Thus, an amelioration of disease in MS would include a reduction in the frequency or severity of onset of weakness, numbness, tingling, loss of vision, memory difficulty, learning disability, and extreme fatigue. On imaging of the brain (MRI) amelioration or reduced progression of disease would be evidenced by a slowing in the rate of cerebral, cerebellar or spinal cord atrophy formation or a stabilization or slowing of the accumulation of T2 lesions.

Patients may also express criteria indicating they are at risk for developing neurodegenerative diseases. These patients may be preventatively treated to delay the onset of clinical signs and/or symptomology. More specifically, patients who present initially with clinically isolated syndromes (CIS) may be treated using the treatment paradigm outlined in this invention. These patients have had at least one clinical event consistent with MS, but have not met full criteria for MS diagnosis since the definite diagnosis requires more than one clinical event at another time. Treatment of the present invention would be advantageous at least in providing a protective effect after the acute phase of clinically definite MS.

PRIMARY AGENT. The primary agents useful in this invention are estrogen receptor β agonists. These agonists may be steroidal or non-steroidal agents which bind to and/or cause a change in activity or binding of the estrogen receptor β. In certain preferred embodiments, the estrogen receptor β agonist agonizes estrogen receptor β with an $EC_{50}$ at least 10 times lower than its $EC_{50}$ for agonizing estrogen receptor α, preferably at least 100 times lower.

One agent useful in this invention alone or in combination is an ERβ ligand, known as AC-186 or compounds substantially similar in structure and function thereto (see the compounds disclosed in PCT Patent Publication WO 2013/017619 A1, incorporated herein by reference), as evidenced at least by treating in the EAE models described below.

SECONDARY ACTIVE AGENTS. Any one or a combination of secondary active agents may be included in combination with the primary agent. Alternatively, any one or a combination of secondary active agents may be administered independently of the primary agent, but concurrent in time for exposure to at least two agents for the treatment of the neurodegenerative disease. Alternatively, the primary and secondary agents may be used in an alternating fashion to prevent or treat neurodegeneration.

The secondary agents are preferably immunotherapeutic agents, which act synergistically with the primary agent to diminish the symptomology of the neurodegenerative disease. Secondary active agents may be selected to enhance the effect of the primary agent, or affect a different system than that affected by the primary agent.

The secondary agent may be selected from the group comprising β-interferon compounds. Examples include as β-interferon (e.g., Avonex® (interferon-beta 1a), Rebif® (by Serono); Extavia®, Betaseron® (interferon-beta 1b; Berlex, Schering), PLEGRIDY™ (peginterferon beta-1a; Biogen)). Optionally, the following agents may be used: dimethyl fumarate (Tecfidera®; BG-12), fingolimod (Gilenya®), glatiramer acetate (Copaxone®), interferon beta-1a (e.g., Avonex® or Rebif®), pegylated interferon-beta-1a (PLEGRIDY™; Biogen) mitoxantrone (Novantrone®; Lederle Labs), natalizumab (Tysabri®), anti-LINGO-1 antibody (BIIB033, Biogen-Idec), Antegren® (Elan Corp.), teriflunomide (Aubagio®), mycophenolate mofetil (CellCept® Hoffman-LaRoche Inc.), paclitaxel (Taxol®; Bristol-Meyers Oncology), cyclosporine (such as cyclosporin A), corticosteroids (e.g., prednisone, methylprednisolone), azathioprine, cyclophosphamide, methotrexate, cladribine, 4-aminopyridine, and tizanidine.

Surprisingly, the estrogen receptor beta ligand of formula I (AC-186) reduces macrophage activity in the brain and spinal cord; thus, the estrogen receptor beta ligand of formula I and other compounds of similar activity may be used as an immunotherapeutic or anti-inflammatory agent. Accordingly, the dose of a secondary agent with immunotherapeutic or anti-inflammatory activity may be reduced when administered in combination with the estrogen receptor beta ligand of formula I, for example, to reduce the occurrence or severity of unwanted side effects associated with the secondary agent. Similarly, the additional agent may be administered at a lower dose due to the synergistic effect with the combination of the first and second agents. Examples include a glucocorticoid, precursor, analog or glucocorticoid receptor agonist or antagonist. For example, prednisone may be administered, most preferably in the dosage range of about 5-60 milligrams per day. Also, methyl prednisone (Solu-Medrol) may be administered, most preferably in the dosage range of about 1-2 milligrams per day. Glucocorticoids are currently used to treat relapse episodes in MS patients within this dosage range.

The dose of the disease-modifying therapeutic may be decreased when used in combination with the estrogen receptor beta ligand. For example, a current standard dose for glatiramer acetate (Copaxone®) is 40 mg subcutaneously (s.c.) three times a week, or 20 mg s.c. daily. In conjunction with the estrogen receptor beta ligand in accordance with the invention, the dose for glatiramer acetate (Copaxone®) may be reduced by up to 10 percent, by up to 15 percent, by up to 20 percent, by up to 25 percent, by up to 30 percent, by up to 35 percent, by up to 40 percent, by up to 45 percent, by up to 50 percent or more, e.g., to 20 mg s.c. six times a week, five times a week, four times a week, or three times a week.

As another example, a current standard dose for fingolimod (Gilenya®) is 0.5 mg by mouth (p.o.) daily. In conjunction with the estrogen receptor beta ligand in accordance with the invention, the dose for fingolimod (Gilenya®) may be reduced by up to 10 percent, by up to 15 percent, by up to 20 percent, by up to 25 percent, by up to 30 percent, by up to 35 percent, by up to 40 percent, by up to 45 percent, by up to 50 percent or more, e.g., to 0.45, 0.40, 0.35, 0.30, or 0.25 mg p.o. daily.

As another example, a current standard dose for dimethyl fumarate (Tecfidera®) is 240 mg p.o. daily. In conjunction with the estrogen receptor beta ligand in accordance with the invention, the dose for dimethyl fumarate (Tecfidera®) may be reduced by up to 10 percent, by up to 15 percent, by up to 20 percent, by up to 25 percent, by up to 30 percent, by up to 35 percent, by up to 40 percent, by up to 45 percent, by up to 50 percent or more, e.g., to 220 mg p.o. daily, 200 mg p.o. daily, 180 mg p.o. daily, 160 mg p.o. daily, 150 mg p.o. daily, 140 mg p.o. daily, or 120 mg p.o. daily.

As yet another example, a current standard dose for interferon beta-1a (Avonex® or Rebif®) is 30 μg intramuscularly (i.m.) weekly (Avonex®) or 44 prg s.c. three days a week (Rebif®). In conjunction with the estrogen receptor beta ligand in accordance with the invention, the dose for Avonex® may be reduced to 27, 26, 25, 24, 23, 22, 21, 20, 19, 18, 17, 16, or 15 μg i.m. weekly, or 30 μg intramuscularly (i.m.) every 8, 9, 10 or 11 days, and the dose for Rebif® may be reduced to 40, 39, 38, 37, 36, 35, 34, 33, 32, 31, 30, 29, 28, 27, 26, 25, 24, 23, or 22 μg s.c. three days a week, or 44 μg s.c. two days a week.

As yet another example, a current standard dose for interferon beta-1b (Betaseron® or Extavia®) is 0.25 mg s.c. every other day (Betaseron® or Extavia®). In conjunction with the estrogen receptor beta ligand in accordance with the invention, the dose for interferon beta-1b (Betaseron® or Extavia®) may be reduced to 0.225, 0.200, 0.180, 0.175, 0.170, 0.160, 0.150, 0.140, 0.130, or 0.125 mg s.c. every other day, or 0.25 mg s.c. every third day.

THERAPEUTICALLY EFFECTIVE DOSAGE OF THE PRIMARY AGENT. A therapeutically effective dose of the primary agent is one sufficient to raise the serum concentration above basal levels, and preferably to produce a biological effect in the central nervous system, with no off target binding effects on breast or uterus.

In certain embodiments where the primary agent is AC-186, the dose may be about 1-100 mg/kg/day, but can be titrated by one of skill in the art to achieve the desired benefits while reducing the risks including side effects of this therapy. In some embodiments, the primary agent is AC-186, and the compound is administered at a dose sufficient to achieve a mean blood concentration of the compound between 1 ng/ml and 1000 ng/ml. In other embodiments, the compound is administered at a dose sufficient to achieve a mean blood concentration of the compound between 100 ng/ml and 200 ng/ml.

The dosage of the primary agent may be selected for an individual patient depending upon the route of administration, severity of disease, age and weight of the patient, other medications the patient is taking and other factors normally considered by the attending physician, when determining the individual regimen and dosage level as the most appropriate for a particular patient.

The use of this group of primary agents is advantageous in at least that other known or experimental treatments for MS are chemotherapeutic immunosuppressants which have significant risks and side effects to patients, including decreasing the ability of the patient to fight infections, inducing liver or heart toxicity which are not caused by estrogen treatment. Other agents used in MS do not cause these side effects, but are associated with flu-like symptoms or chest tightness. Further, these previously used agents are associated with local skin reactions since they entail injections at frequencies ranging from daily to once per week.

DOSAGE FORM. The therapeutically effective dose of the primary agent included in the dosage form is selected at least by considering the primary agent selected and the mode of administration, preferably oral. The dosage form may include the active primary agent in combination with other inert ingredients, including adjutants and pharmaceutically acceptable carriers for the facilitation of dosage to the patient as known to those skilled in the pharmaceutical arts. The dosage form may be any form suitable to cause the primary agent to enter into the tissues of the patient.

In certain embodiments, the primary agent is formulated for buccal or sublingual administration. For example, the dosage form of the primary agent may be a tablet, drop, spray, film, thin-film, or lozenge.

In one embodiment, the dosage form of the primary agent is an oral preparation (liquid, tablet, capsule, caplet or the like) which when consumed results in elevated levels of the primary agent in blood serum. The oral preparation may comprise conventional carriers including diluents, binders, time release agents, lubricants and disintegrants.

Possible oral administration forms are all the forms known from the prior art such as, tablets, dragees, pills or capsules, which are produced using conventional adjuvants and carrier substances. In the case of oral administration it has provided appropriate to place the daily units, which in case comprise a combination of the primary and secondary agents, in a spatially separated and individually removable manner in a packaging unit, so that it is easy to check whether the typically daily taken, oral administration form has in fact been taken as it is important to ensure that there are no taking-free days.

In other embodiments of the invention, the dosage form may be provided in a topical preparation (lotion, creme, ointment, patch or the like) for transdermal application. Alternatively, the dosage form may be provided in a suppository or the like for intravaginal or transrectal application. Alternatively, the agents may be provided in a form for injection or for implantation.

In the transdermal administration of the combination according to the invention, the agents may be applied to a plaster or also can be applied by transdermal, therapeutic systems and are consequently supplied to the organism. For example, an already prepared combination of the agents or the latter individually can be introduced into such a system, which is based on ionotherapy or diffusion or optionally a combination of these effects.

That the agents can be delivered via these dosage forms is advantageous in that currently available therapies, for MS for example, many are injectables, which are inconvenient for the user and lead to decreased patient compliance with the treatment. Non-injectable dosage forms are further advantageous over current injectable treatments which often cause side effects in patients including flu-like symptoms (particularly, β interferon) and injection site reactions which may lead to lipotrophy (particularly, glatiramer acetate copolymer-1). Currently available oral treatments for MS, however, consist of only anti-inflammatory agents, which display only a modest effect on disability and are only effective in the early stages of the disease.

However, in additional embodiment, the dosage form may also allow for preparations to be applied subcutaneously, intravenously, intramuscularly or via the respiratory system. DOSE. By way of example, which is consistent with the current therapeutic uses for these treatments, Avonex® in a dosage of about 0 to about 30 mcg may be injected intramuscularly once a week. Betaseron® in a dosage of about 0 to about 0.25 mg may be injected subcutaneously every other day. Copaxone®@ in a dosage of about 0 to about 20 mg may be injected subcutaneously every day. Finally, Rebif® may be injected at a therapeutic dose and at an interval to be determined based on clinical trial data. One objective would be to select the minimal effective dose of β-interferon given the side effects, injection site reactions and compliance issues associated with its use. Thus, the second agent may be administered at a reduced dose or with reduced frequency due to synergistic effects with the primary agent. However, dosages and method of administration may be altered to maximize the effect of these therapies in conjunction with estrogen β receptor ligand treatment. Dosages may be altered using criteria that are known to those skilled in the art of diagnosing and treating autoimmune diseases.

In certain aspects, the invention relates to methods of slowing or halting gray matter atrophy in a neurodegenerative disease patient, comprising administering to the patient an estrogen receptor beta ligand.

In certain embodiments, the invention relates to methods of reversing gray matter atrophy in a neurodegenerative disease patient, comprising administering to the patient an estrogen receptor beta ligand.

In certain embodiments, the invention relates to methods of slowing or halting progression of disability in a neurodegenerative disease patient, comprising administering to the patient an estrogen receptor beta ligand.

In certain embodiments, the invention relates to methods of reversing progression of disability in a neurodegenerative disease patient, comprising administering to the patient an estrogen receptor beta ligand.

In certain embodiments, the invention relates to methods of preventing the progression of a neurodegenerative disease, comprising administering to a patient presenting with cognitive disability an effective amount of an estrogen receptor beta ligand.

In certain embodiments, the invention relates to methods of treating neurodegenerative disease in a patient having cognitive disability, comprising administering to the patient an effective amount of an estrogen receptor beta ligand.

In certain embodiments, the invention relates to methods of treating and/or slowing the progression of a neurodegenerative disease, comprising evaluating a patient's cognitive ability, and administering an effective amount of an estrogen receptor beta ligand to a patient suffering from cognitive disability.

In certain embodiments, the invention relates to methods of slowing or halting the progression of memory loss in a neurodegenerative disease patient, comprising administering to the patient an estrogen receptor beta ligand.

In certain embodiments, the invention relates to methods of reversing the progression of memory loss in a neurodegenerative disease patient, comprising administering to the patient an estrogen receptor beta ligand.

In certain embodiments, the invention relates to methods of preventing the progression of a neurodegenerative disease, comprising administering to a patient presenting with memory loss an effective amount of an estrogen receptor beta ligand.

In certain embodiments, the invention relates to methods of treating neurodegenerative disease in a patient having substantial memory loss, comprising administering to the patient an effective amount of an estrogen receptor beta ligand.

In certain embodiments, the invention relates to methods of treating and/or slowing the progression of a neurodegenerative disease, comprising evaluating a patient's memory, and administering an effective amount of an estrogen receptor beta ligand to a patient suffering from memory loss.

In certain embodiments, the invention relates to methods of slowing or halting the progression of a learning disability in a neurodegenerative disease patient, comprising administering to the patient an estrogen receptor beta ligand.

In certain embodiments, the invention relates to methods of reversing the progression of a learning disability in a neurodegenerative disease patient, comprising administering to the patient an estrogen receptor beta ligand.

In certain embodiments, the invention relates to methods of preventing the progression of a neurodegenerative disease, comprising administering to a patient presenting with a learning disability an effective amount of an estrogen receptor beta ligand.

In certain embodiments, the invention relates to methods of treating neurodegenerative disease in a patient having a learning disability, comprising administering to the patient an effective amount of an estrogen receptor beta ligand.

In certain embodiments, the invention relates to methods of treating and/or slowing the progression of a neurodegenerative disease, comprising evaluating a patient's learning ability, and administering an effective amount of an estrogen receptor beta ligand to a patient suffering from learning disability.

In certain embodiments, the invention relates to methods of preventing the progression of a neurodegenerative disease, comprising administering to a patient presenting with brain gray matter atrophy an effective amount of an estrogen receptor beta ligand.

In certain embodiments, the invention relates to methods of treating neurodegenerative disease in a patient having substantial brain gray matter atrophy, comprising administering to the patient an effective amount of an estrogen receptor beta ligand.

In certain embodiments, the invention relates to methods of treating and/or slowing the progression of a neurodegenerative disease, comprising evaluating a patient's brain gray matter, and administering an effective amount of an estrogen receptor beta ligand to a patient suffering from brain gray matter atrophy.

In certain embodiments, the invention relates to methods of treating or preventing a neurodegenerative disease in a patient having greater than about 0.1% brain gray matter loss per annum, comprising administering to the patient an effective amount of an estrogen receptor beta ligand. In certain embodiments, the invention relates to methods of treating or preventing a neurodegenerative disease in a patient having greater than about 0.5% brain gray matter loss per annum, comprising administering to the patient an effective amount of an estrogen receptor beta ligand.

In certain embodiments, the invention relates to methods of treating a neurodegenerative disease in a patient having a loss of brain gray matter of greater than about 0.3% in a period of at least about 6 months, comprising administering to the patient an effective amount of an estrogen receptor beta ligand.

In certain embodiments, the invention relates to methods of treating a neurodegenerative disease in a patient who is non-responsive to treatment with a multiple sclerosis therapy, comprising administering to the patient an effective amount of an estrogen receptor beta ligand, wherein the patient is classified as non-responsive based on a substantial loss of brain gray matter volume during treatment with the first multiple sclerosis treatment agent.

In some embodiments, the brain gray matter loss per annum is about 0.2%, or about 0.3%, or about 0.4%, or about 0.5%, or about 0.6%, or about 0.7%, or about 0.8%, or about 0.9%, or about 1.0%, or about 1.1%, or about 1.2%, or about 1.3%, or about 1.4%, or about 1.5%, or about 2.0%. In some embodiments, the loss of brain gray matter is about 0.4%, or about 0.5%, or about 0.6%, or about 0.7%, or about 0.8%, or about 0.9%, or about 1.0%, or about 1.1%, or about 1.2%, or about 1.3%, or about 1.4%, or about 1.5%, or about 2.0 in a period of about 6 months, or about 12 months, or about 18 months, or about 24 months. The gray matter loss may be located in one or more of total brain, cerebral cortex, cerebellum, thalamus, caudate nucleus, and putamen.

The gray matter loss may be measured using an imaging technique or surrogate marker. In some embodiments, the gray matter loss is measured using an imaging technique selected from magnetic resonance imaging (MRI), fast fluid-attenuated inversion recovery (FLAIR), double inversion recovery (DIR), phase-sensitive inversion recovery (PSIR), ultra high-field MRI, magnetization transfer imaging (MTI), T1-relaxometry, diffusion tensor imaging (DTI), proton magnetic resonance spectroscopy (MRS)), and related techniques and combinations thereof. The gray matter loss may be measured using a surrogate marker selected from one or more of nogo receptor, kallikrein-6 (neurosin), cerebellin-1, ceruloplasmin, dickkopf-3 (rig-like 7-1), amyloid beta precursor-like protein 1, activated leukocyte cell adhesion molecule (CD166), neural cell adhesion molecule 2, neural epidermal growth factor like 2/cerebral protein-12, clusterin (apolipoprotein j, complement lysis inhibitor), brevican, neuronal cadherin, chitinase-3-like 1 protein, neogenin, multifunctional protein MFP (collagen alpha-1 (XVIII) chain; endostatin), dystroglycan 1, contactin 2, ephrin type a receptor 4, neural cell adhesion molecule L1 like protein, and contactin 1.

In some embodiments, the treatment comprises one or more of preventing disease progression, slowing of disease progression, reducing the number of disease relapses or clinical exacerbations, and slowing the accumulation of physical disability.

In some embodiments, the patient has one or more of: experienced a first clinical episode, MRI features consistent with multiple sclerosis, an inadequate response to an alternate MS therapy, and an inability to tolerate an alternate MS therapy.

In certain embodiments, the method is a method for slowing, halting, or reversing progression of a cognitive or physical disability in a subject with a neurodegenerative disease, comprising identifying a subject who has experienced progression of a cognitive or physical disability and initiating treatment of the subject by a method as described herein. In certain embodiments, the method further comprises testing the severity of the subject's cognitive or physical disability to determine a score representative of the state of the subject's cognitive or physical disability after receiving the treatment for at least about six months, and, optionally, comparing the score to a score determined for the subject prior to or at about the time of initiating the treatment.

In certain embodiments, the method is a method for slowing, halting, or reversing the progression of memory loss in a subject with a neurodegenerative disease, comprising identifying a subject who has experienced progression of memory loss and initiating treatment of the subject by a method as described herein. In certain embodiments, the method further comprises testing the severity of the subject's memory loss to determine a score representative of the state of the subject's memory after receiving the treatment for at least about six months, and, optionally, comparing the score to a score determined for the subject prior to or at about the time of initiating the treatment.

In certain embodiments, the method is a method for slowing, halting, or reversing the progression of a learning disability in a subject with a neurodegenerative disease, comprising identifying a subject who has experienced progression of a learning disability and initiating treatment of the subject by a method as described herein. In certain embodiments, the method further comprises testing the severity of the subject's learning disability to determine a score representative of the state of the subject's learning ability after receiving the treatment for at least about six months, and, optionally, comparing the score to a score determined for the subject prior to or at about the time of initiating the treatment.

The various methods disclosed herein can be methods for improving walking, vision, balance, cognition, learning, memory, or other symptoms in a subject, such as a subject with multiple sclerosis, and/or methods for improving multiple sclerosis functional composite (MSFC), EDSS, 7/24 test, or MSSS scores in a subject, such as a subject with multiple sclerosis. Thus, in certain embodiments, the methods of treatment disclosed herein include methods for stabilizing or improving disability in a patient, whereby the patient's disability score (as measured by either of these tests or another suitable test) after six months, one year, or two years of therapy is at least about 10%, at least about 25%, at least about 40%, at least about 50%, or even at least about 60% higher relative to a control patient not receiving the estrogen receptor beta ligand (but otherwise receiving the same treatment as the patient). Alternatively, the patient's disability score (as measured by either of these tests or another suitable test) after six months, one year, or two years of therapy is within about 2% or within about 5% of an earlier assessment, or at least about 2%, at least about 5%, at least about at least about 10%, at least about 25%, at least about 40%, at least about 50%, or even at least about 60% higher than the earlier assessment.

For example, progression of a walking disability can be tested using a walking test, e.g., assessing the subject's performance on a 25-foot walk test at different points in time, such as at 0 months (baseline), 6 months, 1 year, and 2 years. In certain embodiments, if there is documented worsening in walking (takes more seconds) by 20 percent as compared to baseline (optionally if this worsening is confirmed on a subsequent walk test (e.g., 3 months later)), then the subject is deemed to have progressive worsening in walking. For such a patient not already receiving an estrogen receptor beta ligand therapy, the subject demonstrating the progressive walking disability commences treatment with an estrogen receptor beta ligand. The walking test may be repeated (e.g., at 1 year and/or 2 years from the start of an estrogen receptor beta ligand treatment) to assess whether the treatment slowed or halted any further worsening in walking performance, e.g., as measured by the walking test.

Improvements in cognition outcomes associated with MS therapy, whether slowing of cognitive decline, stabilization of cognitive decline, or improvement of cognitive function, can be assessed using the PASAT (e.g., PASAT 2 or PASAT 3) or SDMT test, or alternatively the MS-COG test (see Erlanger et al., *J Neuro Sci* 340: 123-129 (2014)). Thus, in certain embodiments, the methods of treatment disclosed herein include methods for stabilizing or improving cognition in a patient, whereby the patient's cognition outcome after one year of therapy is at least about 2%, at least about 5%, at least about 10%, at least about 25%, at least about 40%, at least about 50%, or even at least about 60% higher relative to a control patient not receiving the estrogen receptor beta ligand therapy (but otherwise receiving the same treatment as the estrogen receptor beta ligand patient), e.g., as measured by any of the preceding tests. Alternatively, the patient's cognition outcome after six months, one year, or two years of therapy may be within about 2% or within about 5% of an earlier assessment, or at least about 2%, at least about 5%, at least about 10%, at least about 25%, at least about 40%, at least about 50%, or even at least about 60% higher than the earlier assessment, e.g., as measured by any of the preceding tests at different times.

Improvements in memory associated with MS therapy, whether slowing of memory loss, stabilization of memory loss, or improvement of memory, can be assessed using, for example, the 7/24 Spatial Recall Test. Thus, in certain embodiments, the methods of treatment disclosed herein include methods for stabilizing memory loss or improving memory in a patient, whereby the patient's memory after one year of therapy is at least about 10%, at least about 25%, at least about 30%, at least about 40%, at least about 45%, at least about 50%, or even at least about 60% higher relative to a control patient not receiving the estrogen/progestogen therapy (but otherwise receiving the same treatment as the estrogen-treated patient), e.g., as measured by the 7/24 Spatial Recall Test.

In some embodiments, substantial loss of memory refers to less than perfect performance or worsening performance on the 7/24 Spatial Recall Test or Delayed Recall Test. For example, a subject who scores less than 7 on the Spatial Recall Test or Delayed Recall Test has substantial memory loss. Additionally, a subject who scores a 7 on the 7/24 Spatial Recall Test or Delayed Recall Test on a first date followed by a score of 6 or less on a subsequent date has substantial loss of memory over the period of time defined by the first date and the subsequent date.

For example, a subject who scores below 50 on PASAT (and optionally if such low score is verified upon a second subsequent test, such as within one week to one month of the first) may be deemed to have cognitive disability. For such a patient not already receiving treatment, the subject demonstrating the cognitive disability may commence treatment with an estrogen receptor beta ligand. In certain embodiments, the cognitive test may be repeated (e.g., at about six months from the start of treatment) to assess whether the treatment slowed or halted any further worsening in cognitive performance, e.g., as measured by the PASAT test. In certain such embodiments, the patient's score may increase by at least 3 points over the course of six to twelve months of the estrogen receptor beta ligand therapy.

The estrogen receptor beta ligand may be a compound having the structure of formula I:

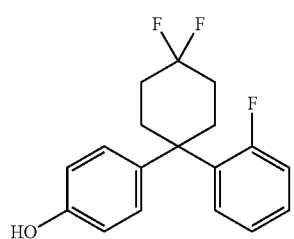

The compound of formula I is called AC-186. In some embodiments, the estrogen receptor beta ligand is a compound that is substantially similar in structure and function to AC-186, such as one of the compounds disclosed in U.S. Patent Application Publication Nos. 2009/0131510 and 2014/0275284, and PCT Patent Application Publication Nos. WO 2013/017619 and WO 2014/125121 (hereby incorporated by reference, especially for the molecules disclosed therein).

In some embodiments, the ERβ ligand is a compound selected from the compounds disclosed in U.S. Patent Application Publication Nos. 2012/0128435, 2012/0202853, 2012/0202861, 2013/0131061, or 2014/0323518 and PCT Patent Application Publication Nos. WO 2012/022776 and 2012/136772 (hereby incorporated by reference, especially for the molecules disclosed therein). In some embodiments, the ERβ ligand is KBRV1 or KBRV2 (Karo Bio, Huddinge, Sweden).

The ERβ ligand may be any one of the following compounds:
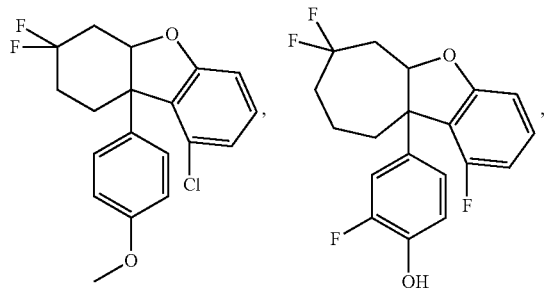
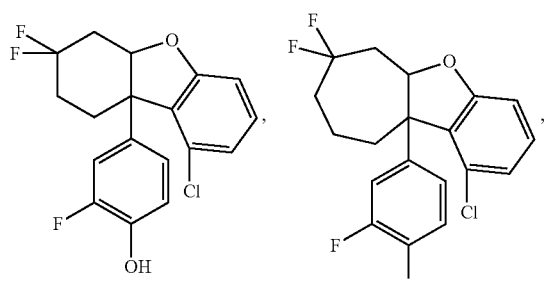
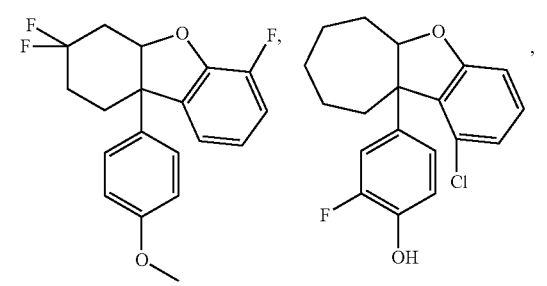
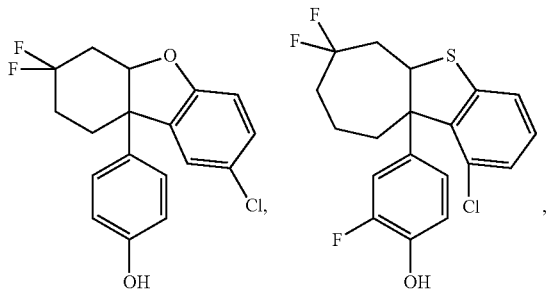
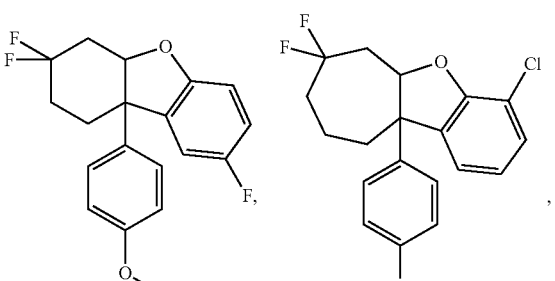
-continued
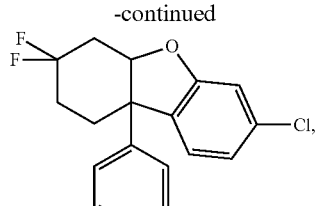
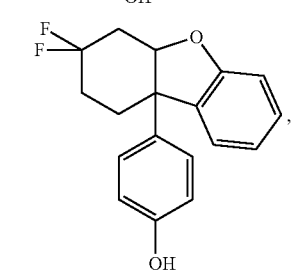
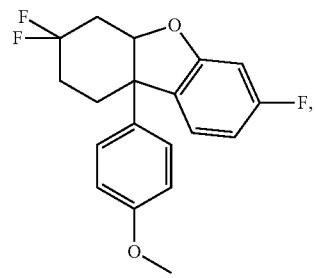
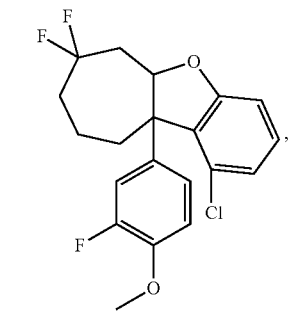
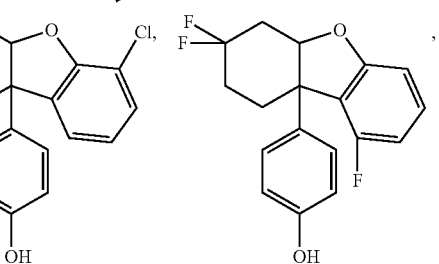
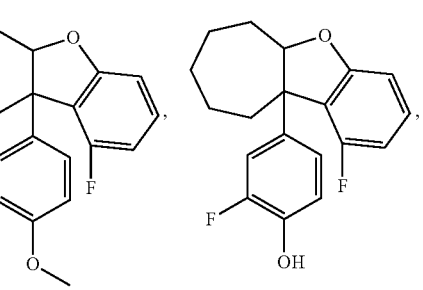

-continued
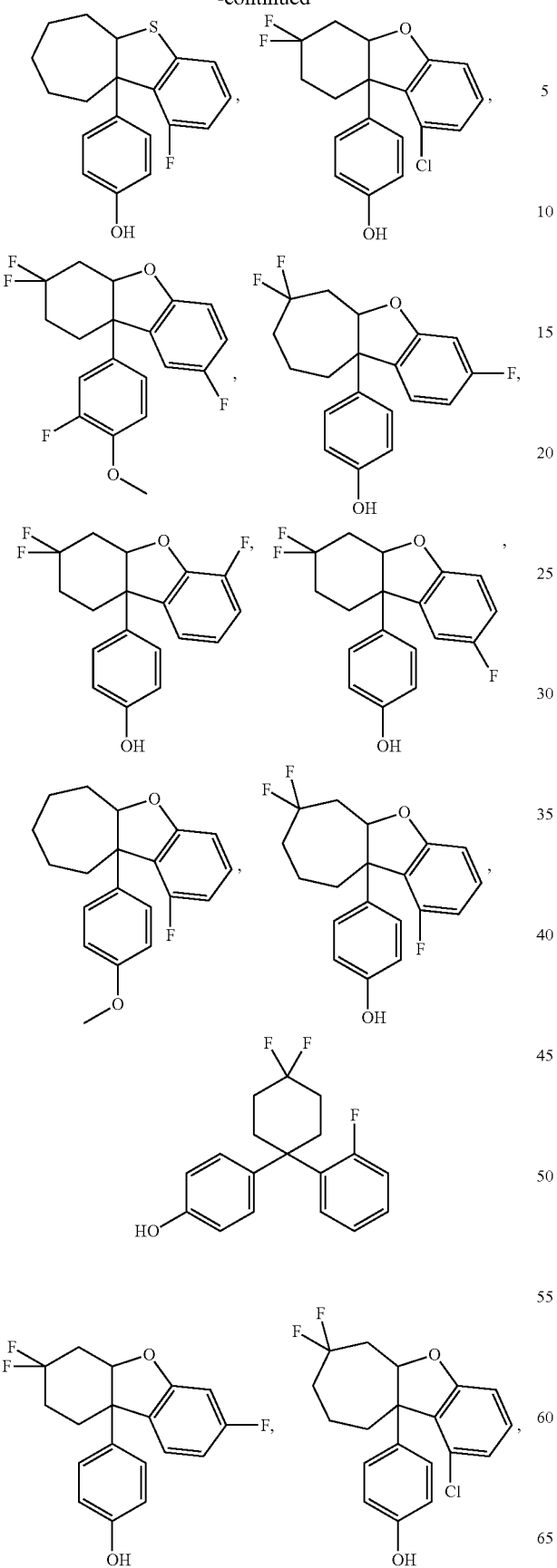
-continued
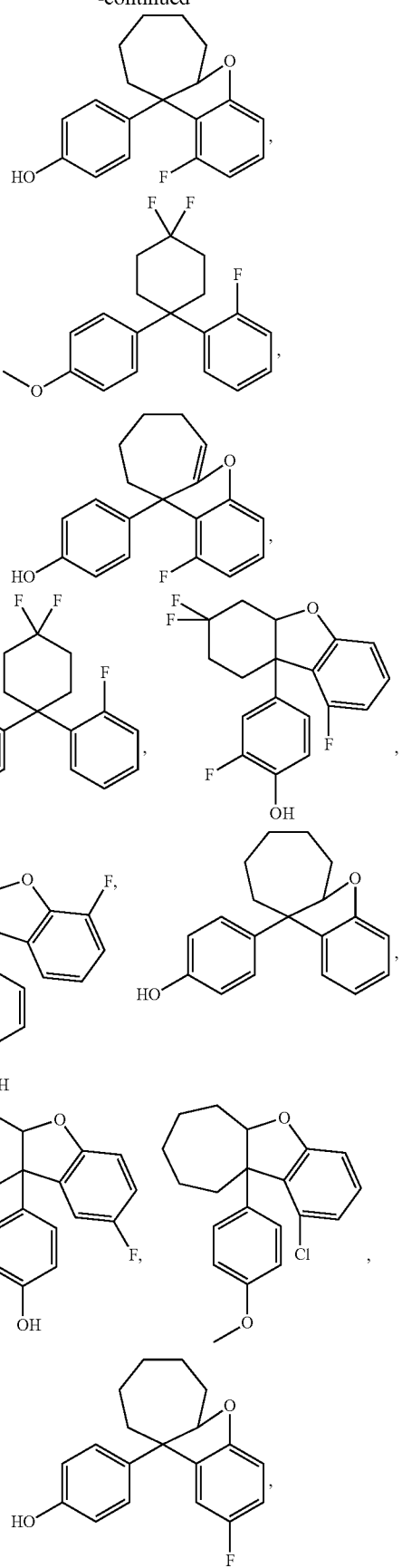

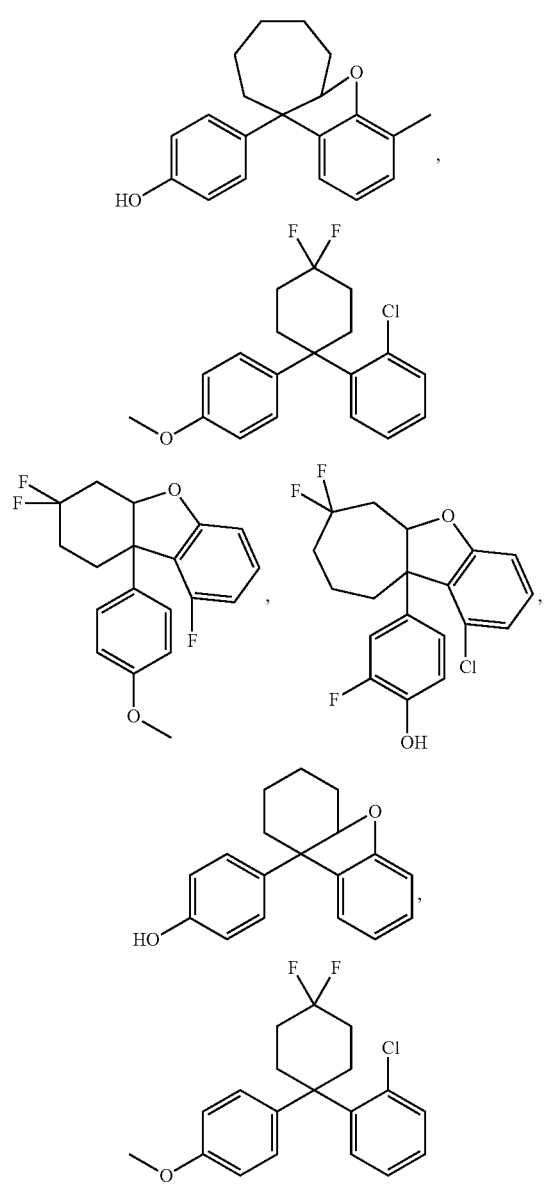

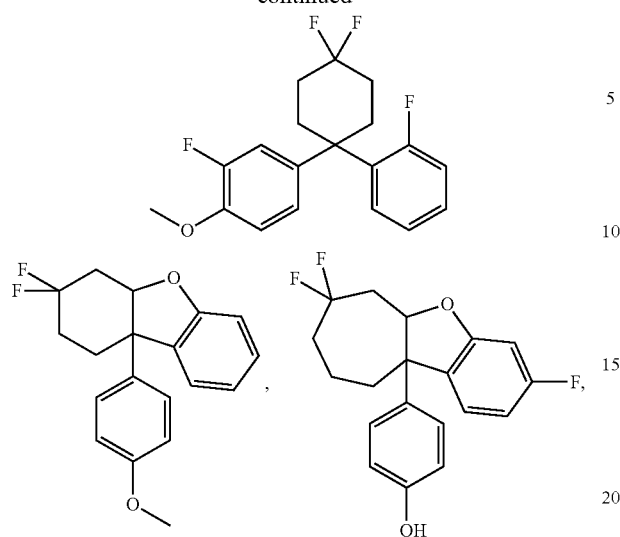

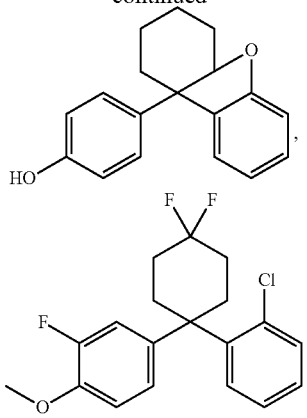

In some embodiments, the ERβ ligand is Compound II, III, or IV.

II

III

IV

The ERβ ligand may be 5-(3,5-dimethylisoxazol-4-yl)-N'-hydroxy-1-(4-hydroxyphenyl)-3-methyl-1H-pyrazole-4-carboximidamide; 5-(3,5-dimethylisoxazol-4-yl)-1-(4-hydroxyphenyl)-3-methyl-1H-pyrazole-4-carboxamide; 5-(3,5-dimethylisoxazol-4-yl)-1-(4-hydroxyphenyl)-3-methyl-1H-pyrazole-4-carbaldehyde oxime; 5-(3,5-dimethylisoxazol-4-yl)-1-(4-hydroxyphenyl)-3-propyl-1H-pyrazole-4-carbaldehyde oxime; 5-(3,5-dimethylisoxazol-4- yl)-N'-hydroxy-1-(4-hydroxyphenyl)-3-propyl-1H-pyrazole-4-carboximidamide; 5-(2,5-dimethyl-1H-pyrrol-1-yl)-1-(2-fluoro-4-hydroxyphenyl)-N'-hydroxy-3-methyl-1H-pyrazole-4-carboximidamide; 5-(diethylamino)-3-ethyl-N'-hydroxy-1-(4-hydroxyphenyl)-1H-pyrazole-4-carboximidamide; 5-(1,3-dimethyl-1H-pyrrol-2-yl)-1-(2-fluoro-4-hydroxyphenyl)-N'-hydroxy-3-methyl-1H-pyrazole-4-carboximidamide; 5-(5-bromo-1,3-dimethyl-1H-pyrrol-2-yl)-1-(2-fluoro-4-hydroxyphenyl)-N'-hydroxy-3-methyl-1H-pyrazole-4-carboximidamide; 3-ethyl-N'-hydroxy-1-(4-hydroxyphenyl)-5-(3-methylfuran-2-yl)-1H-pyrazole-4-carboximidamide; 4-(4-(3,5-dimethylisoxazol-4-yl)-5-(hydroxymethyl)-1-methyl-1H-pyrazol-3-yl)phenol; 4-(3,5-dimethylisoxazol-4-yl)-3-(4-hydroxyphenyl)-1-methyl-1H-pyrazole-5-carbaldehyde oxime; 4-(3,5-dimethylisoxazol-4-yl)-N'-hydroxy-3-(4-hydroxyphenyl)-1-methyl-1H-pyrazole-5-carboximidamide; 4-(3,5-dimethylisoxazol-4-yl)-3-(4-hydroxyphenyl)-1-methyl-1H-pyrazole-5-carboxamide; 4-(4-(3,5-dimethylisoxazol-4-yl)-5-(2-hydroxyethyl)-1-methyl-1H-pyrazol-3-yl)phenol; 4-(2,6-difluorophenyl)-N'-hydroxy-3-(4-hydroxyphenyl)-1-methyl-1H-pyrazole-5-carboximidamide; 5-(3,5-dimethylisoxazol-4-yl)-1-(4-hydroxyphenyl)-3-methyl-1H-pyrazole-4-carbonitrile; 5-(3,5-dimethylisoxazol-4-yl)-1-(4-hydroxyphenyl)-3-isopropyl-1H-pyrazole-4-carbaldehyde oxime; 5-(3,5-dimethylisoxazol-4-yl)-3-ethyl-1-(4-hydroxyphenyl)-1H-pyrazole-4-carbaldehyde oxime; 5-(3,5-dimethylisoxazol-4-yl)-3-ethyl-N'-hydroxy-1-(4-hydroxyphenyl)-1H-pyrazole-4-carboximidamide; 1-(3,5-difluoro-4-hydroxyphenyl)-5-(3,5-dimethylisoxazol-4-yl)-3-ethyl-N'-hydroxy-1H-pyrazole-4-carboximidamide; 5-(3,5-dimethylisoxazol-4-yl)-3-ethyl-1-(3-fluoro-4-hydroxyphenyl)-N'-hydroxy-1H-pyrazole-4-carboximidamide; 1-(2,3-difluoro-4-hydroxyphenyl)-5-(3,5-dimethylisoxazol-4-yl)-3-ethyl-N'-hydroxy-1H-pyrazole-4-carboximidamide; 5-(3,5-dimethylisoxazol-4-yl)-3-ethyl-1-(2-fluoro-4-hydroxyphenyl)-N'-hydroxy-1H-pyrazole-4-carboximidamide; 1-(2,3-difluoro-4-hydroxyphenyl)-5-(3,5-dimethylisoxazol-4-yl)-3-ethyl-1H-pyrazole-4-carbaldehyde oxime (isomer A); 1-(2,3-difluoro-4-hydroxyphenyl)-5-(3,5-dimethylisoxazol-4-yl)-3-ethyl-1H-pyrazole-4-carbaldehyde oxime (isomer B); 5-(3,5-dimethylisoxazol-4-yl)-3-ethyl-1-(2-fluoro-4-hydroxyphenyl)-1H-pyrazole-4-carbaldehyde oxime; 1-(3,5-difluoro-4-hydroxyphenyl)-5-(3,5-dimethylisoxazol-4-yl)-3-ethyl-1H-pyrazole-4-carbaldehyde oxime; 1-(2,5-difluoro-4-hydroxyphenyl)-5-(3,5-dimethylisoxazol-4-yl)-3-ethyl-N'-hydroxy-1H-pyrazole-4-carboximidamide; 1-(2,5-difluoro-4-hydroxyphenyl)-5-(3,5-dimethylisoxazol-4-yl)-3-ethyl-1H-pyrazole-4-carbaldehyde oxime; 5-(3,5-dimethylisoxazol-4-yl)-1-(2-fluoro-4-hydroxyphenyl)-N'-hydroxy-3-methyl-1H-pyrazole-4-carboximidamide; 5-(3,5-dimethylisoxazol-4-yl)-1-(2-fluoro-4-hydroxyphenyl)-N'-hydroxy-3-propyl-1H-pyrazole-4-carboximidamide; 5-(3,5-dimethylisoxazol-4-yl)-1-(2-fluoro-4-hydroxyphenyl)-3-methyl-1H-pyrazole-4-carbaldehyde oxime; 1-(2,3-difluoro-4-hydroxyphenyl)-3-ethyl-5-(1-methyl-1H-pyrrol-2-yl)-1H-pyrazole-4-carbaldehyde oxime; 2-(2-fluoro-4-hydroxyphenyl)-2',4',5-trimethyl-2H,2'H-3,3'-bipyrazole-4-carbaldehyde oxime; 2-(2-fluoro-4-hydroxyphenyl)-N'-hydroxy-2',4',5-trimethyl-2H,2'H-3,3'-bipyrazole-4-carboximidamide; 5-(2,6-dimethylphenyl)-1-(2-fluoro-4-hydroxyphenyl)-N'-hydroxy-3-methyl-1H-pyrazole-4-carboximidamide; 5-(2,5-dimethyl-1H-pyrrol-1-yl)-3-ethyl-N'-hydroxy-1-(4-hydroxyphenyl)-1H-pyrazole-4-carboximidamide; 5-(2,6-dimethylphenyl)-1-(2-fluoro-4-hydroxyphenyl)-3-methyl-1H-pyrazole-4-carbaldehyde oxime; 5-(2,5-dimethyl-1H-pyrrol-1-yl)-1-(3-fluoro-4-hydroxyphenyl)-N'-hydroxy-3-methyl-1H-pyrazole-4-carboximidamide; 1-(2,3-difluoro-4-hydroxyphenyl)-5-(2,5-dimethyl-1H-pyrrol-1-yl)-N'-hydroxy-3-methyl-1H-pyrazole-4-carboximidamide; 1-(3,5-di fluoro-4-hydroxyphenyl)-5-(2,5-dimethyl-1H-pyrrol-1-yl)-N'-hydroxy-3-methyl-1H-pyrazole-4-carboximidamide; 3-(3-chloro-4-hydroxyphenyl)-4-(3,5-dimethylisoxazol-4-yl)-1-methyl-1H-pyrazole-5-carboxamide; 4-(2,6-difluorophenyl)-3-(4-hydroxyphenyl)-1-methyl-1H-pyrazole-5-carbaldehyde oxime; 4-(2,6-dichlorophenyl)-3-(4-hydroxyphenyl)-1-methyl-1H-pyrazole-5-carbaldehyde oxime; 4-(2,6-dichlorophenyl)-3-(4-hydroxyphenyl)-1-methyl-1H-pyrazole-5-carboxamide; 4-(2,6-dichlorophenyl)-N'-hydroxy-3-(4-hydroxyphenyl)-1-methyl-1H-pyrazole-5-carboximidamide; 4-(3,5-dimethylisoxazol-4-yl)-3-(2-fluoro-4-hydroxyphenyl)-1-methyl-1H-pyrazole-5-carbaldehyde oxime; 4-(3,5-dimethylisoxazol-4-yl)-3-(2-fluoro-4-hydroxyphenyl)-1-methyl-1H-pyrazole-5-carboxamide; 4-(3,5-dimethylisoxazol-4-yl)-3-(2-fluoro-4-hydroxyphenyl)-N'-hydroxy-1-methyl-1H-pyrazole-5-carboximidamide; 5-((Z)-but-2-en-2-yl)-1-(2-fluoro-4-hydroxyphenyl)-N'-hydroxy-3-methyl-1H-pyrazole-4-carboximidamide; 5-(2,4-dimethylthiophen-3-yl)-1-(2-fluoro-4-hydroxyphenyl)-N'-hydroxy-3-methyl-1H-pyrazole-4-carboximidamide; 5-(3,5-dimethylpyridin-4-yl)-1-(2-fluoro-4-hydroxyphenyl)-N'-hydroxy-3-methyl-1H-pyrazole-4-carboximidamide; 5-(3,5-dimethylisoxazol-4-yl)-N'-hydroxy-1-(4-hydroxy-2-methylphenyl)-3-methyl-1H-pyrazole-4-carboximidamide; 5-(3,5-dimethylisoxazol-4-yl)-3-ethyl-N'-hydroxy-1-(4-hydroxy-2-methylphenyl)-1H-pyrazole-4-carboximidamide; 5-(2,5-dimethyl-1H-pyrrol-1-yl)-N'-hydroxy-1-(4-hydroxy-2-methylphenyl)-3-methyl-1H-pyrazole-4-carboximidamide; N'-hydroxy-1-(4-hydroxy-2-methylphenyl)-3-methyl-5-(2-methyl-5-propyl-1H-pyrrol-1-yl)-1H-pyrazole-4-carboximidamide; 4-(2,4-dimethylthiophen-3-yl)-3-(2-fluoro-4-hydroxyphenyl)-N'-hydroxy-1-methyl-1H-pyrazole-5-carboximidamide; 4-(3,5-dimethylisoxazol-4-yl)-3-(3-fluoro-4-hydroxyphenyl)-1-methyl-1H-pyrazole-5-carbaldehyde oxime; 4-(3,5-dimethylisoxazol-4-yl)-3-(3-fluoro-4-hydroxyphenyl)-1-methyl-1H-pyrazole-5-carboxamide; 4-(3,5-dimethylisoxazol-4-yl)-3-(3-fluoro-4-hydroxyphenyl)-N'-hydroxy-1-methyl-1H-pyrazole-5-carboximidamide; (Z)-4-(3,5-dimethylisoxazol-4-yl)-3-(4-hydroxy-2-methylphenyl)-1-methyl-1H-pyrazole-5-carbaldehyde oxime; (E)-4-(3,5-dimethylisoxazol-4-yl)-3-(4-hydroxy-2-methylphenyl)-1-methyl-1H-pyrazole-5-carbaldehyde oxime; 4-(3,5-dimethylisoxazol-4-yl)-N'-hydroxy-3-(4-hydroxy-2-methylphenyl)-1-methyl-1H-pyrazole-5-carboximidamide; 4-(3,5-dimethylisoxazol-4-yl)-3-(4-hydroxy-2-methylphenyl)-1-methyl-1H-pyrazole-5-carboxamide; 4-(2,4-dimethylthiophen-3-yl)-N'-hydroxy-3-(4-hydroxy-2-methylphenyl)-1-methyl-1H-pyrazole-5-carboximidamide; 4-(3,5-dimethylisothiazol-4-yl)-3-(2-fluoro-4-hydroxyphenyl)-N'-hydroxy-1-methyl-1H-pyrazole-5-carboximidamide; 4-(2,6-dimethylphenyl)-3-(2-fluoro-4-hydroxyphenyl)-N'-hydroxy-1-methyl-1H-pyrazole-5-carboximidamide; 4-(2,4-dimethylfuran-3-yl)-3-(4-hydroxyphenyl)-1-methyl-1H-pyrazole-5-carbaldehyde oxime; 4-(3,5-dimethylisothiazol-4-yl)-3-(4-hydroxyphenyl)-1-methyl-1H-pyrazole-5-carbaldehyde oxime; or 4-(3,5-dimethylisothiazol-4-yl)-N'-hydroxy-3-(4-hydroxyphenyl)-1-methyl-1H-pyrazole-5-carboximidamide.

The ERβ ligand may be 2-(3,5-dimethylisoxazol-4-yl)-3-(4-hydroxyphenyl)-1H-indole-1-carbonitrile; 2-(3,5-dimethylisoxazol-4-yl)-N'-hydroxy-3-(4-hydroxyphenyl)-1H- indole-1-carboximidamide; 2-(3,5-dimethylisoxazol-4-yl)-3-(4-hydroxyphenyl)-1H-indole-1-carboxamide; 2-(3,5-dimethylisoxazol-4-yl)-3-(4-hydroxyphenyl)-N,N-dimethyl-1H-indole-1-sulfonamide; 2-(3,5-dimethylisoxazol-4-yl)-3-(4-hydroxyphenyl)-1H-indole-1-carbaldehyde oxime; 4-(2-(3,5-dimethylisoxazol-4-yl)-1-(methylsulfonyl)-1H-indol-3-yl)phenol; 2-((Z)-but-2-en-2-yl)-N'-hydroxy-3-(4-hydroxyphenyl)-1H-indole-1-carboximidamide; 2-(3,5-dimethylisoxazol-4-yl)-N-ethyl-3-(4-hydroxyphenyl)-1H-indole-1-carboxamide; 2-(3,5-dimethylisoxazol-4-yl)-3-(4-hydroxyphenyl)-N-methyl-1H-indole-1-carboxamide; 2-(2,4-dimethylthiophen-3-yl)-N'-hydroxy-3-(4-hydroxyphenyl)-1H-indole-1-carboximidamide; 2-(1,4-dimethylthiophen-3-yl)-3-(4-hydroxyphenyl)-1H-indole-1-carboxamide; 2-(2,6-dimethylphenyl)-N'-hydroxy-3-(4-hydroxyphenyl)-1H-indole-1-carboxamide; 2-(3,5-dimethylisoxazol-4-yl)-3-(4-hydroxyphenyl)-N-isopropyl-1H-indole-1-carboxamide; 2-(3,5-dimethylisoxazol-4-yl)-3-(4-hydroxyphenyl)-N-pentyl-1H-indole-1-carboxamide; 2-(2,4-dimethylthiophen-3-yl)-N-ethyl-3-(4-hydroxyphenyl)-1H-indole-1-carboxamide; 3-(3,5-difluoro-4-hydroxyphenyl)-2-(3,5-dimethylisoxazol-4-yl)-N'-hydroxy-1H-indole-1-carboximidamide; 3-(2,3-difluoro-4-hydroxyphenyl)-2-(3,5-dimethylisoxazol-4-yl)-N'-hydroxy-1H-indole-1-carboximidamide; 2-(3,5-dimethylisoxazol-4-yl)-3-(2-fluoro-4-hydroxyphenyl)-N'-hydroxy-1H-indole-1-carboximidamide; 3-(2,5-difluoro-4-hydroxyphenyl)-2-(3,5-dimethyl isoxazol-4-yl)-N'-hydroxy-1H-indole-1-carboximidamide; 2-(3,5-dimethylisoxazol-4-yl)-3-(3-fluoro-4-hydroxyphenyl)-N'-hydroxy-1H-indole-1-carboximidamide; 5-chloro-2-(3,5-dimethylisoxazol-4-yl)-N'-hydroxy-3-(4-hydroxyphenyl)-1H-indole-1-carboximidamide; 2-(2,4-dimethylfuran-3-yl)-N'-hydroxy-3-(4-hydroxyphenyl)-1H-indole-1-carboximidamide; 2-(3,5-dimethylisothiazol-4-yl)-N'-hydroxy-3-(4-hydroxyphenyl)-1H-indole-1-carboximidamide; 2-(3,5-dimethylisothiazol-4-yl)-3-(4-hydroxyphenyl)-1H-indole-1-carboxamide; 5-chloro-2-(3,5-dimethylisoxazol-4-yl)-N'-hydroxy-3-(4-hydroxyphenyl)-1H-indole-1-carboximidamide; 2-(2,4-dimethylfuran-3-yl)-N'-hydroxy-3-(4-hydroxyphenyl)-1H-indole-1-carboximidamide; 2-(3,5-dimethylisothiazol-4-yl)-N'-hydroxy-3-(4-hydroxyphenyl)-1H-indole-1-carboximidamide; or 2-(3,5-dimethylisothiazol-4-yl)-3-(4-hydroxyphenyl)-1H-indole-1-carboxamide The ERβ ligand may be 2-(3,5-dimethylisoxazol-4-yl)-N'-hydroxy-3-(4-hydroxyphenyl)-2,4,5,6-tetrahydrocyclopenta[c]pyrrole-1-carboximidamide; 2-(3,5-dimethylisoxazol-4-yl)-3-(2-fluoro-4-hydroxyphenyl)-N'-hydroxy-5,6-dihydrocyclopenta[b]pyrrole-1 (4H)-carboximidamide; 3-(2,6-difluoro-4-hydroxyphenyl)-2-(3,5-dimethylisoxazol-4-yl)-N'-hydroxy-5,6-dihydrocyclopenta[b]pyrrole-1 (4H)-carboximidamide; 3-(2,5-difluoro-4-hydroxyphenyl)-2-(3,5-dimethyl isoxazol-4-yl)-N'-hydroxy-5,6-dihydrocyclopenta[b]pyrrole-1 (4H)-carboximidamide; 3-(2-chloro-4-hydroxyphenyl)-2-(3,5-dimethylisoxazol-4-yl)-N'-hydroxy-5,6-dihydrocyclopenta[b]pyrrole-1 (4H)-carboximidamide; 3-(2-chloro-6-fluoro-4-hydroxyphenyl)-2-(3,5-dimethylisoxazol-4-yl)-N'-hydroxy-5,6-dihydrocyclopenta[b]pyrrole-1 (4H)-carboximidamide; 3-(2,3-difluoro-4-hydroxyphenyl)-2-(3,5-dimethylisoxazol-4-yl)-N'-hydroxy-5,6-dihydrocyclopenta[b]pyrrole-1(4H)-carboximidamide; 3-(3,5-difluoro-4-hydroxyphenyl)-2-(3,5-dimethylisoxazol-4-yl)-N'-hydroxy-5,6-dihydrocyclopenta[b]pyrrole-1 (4H)-carboximidamide; 2-(3,5-dimethylisoxazol-4-yl)-N'-hydroxy-3-(4-hydroxyphenyl)-4,5,67-tetrahydro-1H-indole-1-carboximidamide; 2-(3,5-dimethylisoxazol-4-yl)-3-(2-fluoro-4-hydroxyphenyl)-N'-hydroxy-4,5,6,7-tetrahydro-1H-indole-1-carboximidamide; 3-(2,6-difluoro-4-hydroxyphenyl)-2-(3,5-dimethylisoxazol-4-yl)-N'-hydroxy-4,5,6,7-tetrahydro-1H-indole-1-carboximidamide; 3-(2,5-difluoro-4-hydroxyphenyl)-2-(3,5-dimethyl isoxazol-4-yl)-N'-hydroxy-4,5,6,7-tetrahydro-1H-indole-1-carboximidamide; 3-(2-chloro-4-hydroxyphenyl)-2-(3,5-dimethylisoxazol-4-yl)-N'-hydroxy-4,5,6,7-tetrahydro-1H-indole-1-carboximidamide; 3-(2,3-difluoro-4-hydroxyphenyl)-2-(3,5-dimethylisoxazol-4-yl)-N'-hydroxy-4,5,6,7-tetrahydro-1H-indole-1-carboximidamide; or 3-(3,5-difluoro-4-hydroxyphenyl)-2-(3,5-dimethylisoxazol-4-yl)-N'-hydroxy-4,5,6,7-tetrahydro-1H-indole-1-carboximidamide.

The ERβ ligand may be N',4'-dihydroxy-2-(3-methylthiophen-2-yl)-5-propyl-[1,1'-biphenyl]-3-carboximidamide; 2-(3,5-dimethylisoxazol-4-yl)-N',4'-dihydroxy-5-methyl-[1,1'-biphenyl]-3-carboximidamide; 2-(3,5-dimethyl isoxazol-4-yl)-N',4'-dihydroxy-5-propyl-[1,1'-biphenyl]-3-carboximidamide; 2-(3,5-dimethylisoxazol-4-yl)-4'-hydroxy-5-propyl-[1,1'-biphenyl]-3-carboxamide; 2-(3,5-dimethylisoxazol-4-yl)-4'-hydroxy-5-propyl-[1,1'-biphenyl]-3-carbonitrile; N',4'-dihydroxy-5-methyl-2-(3-methylthiophen-2-yl)-[1,1'-biphenyl]-3-carboximidamide; 3',5'-difluoro-N',4-dihydroxy-2-(3-methylthiophen-2-yl)-5-propyl-[1,1'-biphenyl]-3-carboximidamide; 2-bromo-3',5'-difluoro-N',4'-dihydroxy-5-propyl-[1,1'-biphenyl]-3-carboximidamide; 2-(3,5-dimethylisoxazol-4-yl)-3',5'-difluoro-N',4'-dihydroxy-5-propyl-[1,1'-biphenyl]-3-carboximidamide; 5-bromo-N',4-dihydroxy-2-(3-methylthiophen-2-yl)-[1,1'-biphenyl]-3-carboximidamide; 5-bromo-N',4'-dihydroxy-2-iodo-[1,1'-biphenyl]-3-carboximidamide; 5'-bromo-N',4-dihydroxy-[1,1':2',1''-terphenyl]-3'-carboximidamide; 5''-fluoro-N',4-dihydroxy-2'',5'-dimethyl-[1,1':2',1''-terphenyl]-3'-carboximidamide; 5''-fluoro-4-hydroxy-2'',5'-dimethyl-[1,1':2',1''-terphenyl]-3'-carboxamide; 5-chloro-2-(3,5-dimethylisoxazol-4-yl)-N',4'-dihydroxy-[1,1'-biphenyl]-3-carboximidamide; 5-chloro-2-(3,5-dimethylisoxazol-4-yl)-4'-hydroxy-[1,1'-biphenyl]-3-carboxamide; 2-(3,5-dimethylisoxazol-4-yl)-3'-fluoro-N',4'-dihydroxy-5-propyl-[1,1'-biphenyl]-3-carboximidamide; 2-(2,4-dimethylfuran-3-yl)-4'-hydroxy-5-propyl-[1,1'-biphenyl]-3-carbonitrile; 2-(2,4-dimethylfuran-3-yl)-N',4'-dihydroxy-5-propyl-[1,1'-biphenyl]-3-carboximidamide; 2-(2,4-dimethylfuran-3-yl)-4'-hydroxy-5-propyl-[1,1'-biphenyl]-3-carboxamide; N',4'-dihydroxy-2-iodo-5-propyl-[1,1'-biphenyl]-3-carboximidamide; N',4'-dihydroxy-2-(4-methylthiophen-3-yl)-5-propyl-[1,1'-biphenyl]-3-carboximidamide; N',4-dihydroxy-5'-propyl-2''-(trifluoromethoxy)-[1,1':2',1''-terphenyl]-3'-carboximidamide; 2-(2,4-dimethylthiophen-3-yl)-N',4'-dihydroxy-5-propyl-[1,1'-biphenyl]-3-carboximidamide; N',4-dihydroxy-5'-propyl-[1,1':2',1''-terphenyl]-3'-carboximidamide; 2-((E)-2-cyclopropylvinyl)-N',4'-dihydroxy-5-propyl-[1,1'-biphenyl]-3-carboximidamide; N',4'-dihydroxy-2-(3-methylbut-2-en-2-yl)-5-propyl-[1,1'-biphenyl]-3-carboximidamide; N',4-dihydroxy-3''-methyl-5'-propyl-[1,1':2',1''-terphenyl]-3'-carboximidamide; 5''-fluoro-N',4-dihydroxy-2''-methyl-5'-propyl-[1,1':2',1''-terphenyl]-3'-carboximidamide; 2''-ethyl-N',4-dihydroxy-5'-propyl-[1,1':2',1''-terphenyl]-3'-carboximidamide; N',4'-dihydroxy-5-propyl-2-(thiophen-2-yl)-[1,1'-biphenyl]-3-carboximidamide; N',4'-dihydroxy-5-propyl-2-(quinolin-5-yl)-[1,1'-biphenyl]-3-carboximidamide; 3''-chloro-N',4-dihydroxy-5'-propyl-[1,1':2',1''-terphenyl]-3'-carboximidamide; N',4'-dihydroxy-5-propyl-2-(pyridin-3- yl)-[1,1'-biphenyl]-3-carboximidamide; 2-(benzofuran-5-yl)-N',4'-dihydroxy-5-propyl-[1,1'-biphenyl]-3-carboximidamide; 4"-chloro-N',4-dihydroxy-5'-propyl-[1,1':2',1"-terphenyl]-3'-carboximidamide; N',4'-dihydroxy-5-propyl-2-(pyridin-4-yl)-[1,1'-biphenyl]-3-carboximidamide; N',4'-dihydroxy-2-(1-phenylvinyl)-5-propyl-[1,1'-biphenyl]-3-carboximidamide; 2-(5-chlorothiophen-2-yl)-N',4'-dihydroxy-5-propyl-[1,1'-biphenyl]-3-carboximidamide; 5"-fluoro-N',4-dihydroxy-2"-methoxy-5'-propyl-[1,1':2',1"-terphenyl]-3'-carboximidamide; N',4'-dihydroxy-2-(isoquinolin-6-yl)-5-propyl-[1,1'-biphenyl]-3-carboximidamide; 2-(benzofuran-3-yl)-N',4'-dihydroxy-5-propyl-[1,1'-biphenyl]-3-carboximidamide; 5"-fluoro-N',4-dihydroxy-2"-methoxy-5'-(trifluoromethyl)-[,1':2',1"-terphenyl]-3'-carboximidamide; 5"-fluoro-N',4-dihydroxy-2"-methyl-5'-(trifluoromethyl)-[1,1':2',1"-terphenyl]-3'-carboximidamide; N',4-dihydroxy-2"-methyl-5'-(trifluoromethyl)-[1,1':2',1"-terphenyl]-3'-carboximidamide; N',4-dihydroxy-5'-(trifluoromethyl)-[1,1':2',1"-terphenyl]-3'-carboximidamide; N',4'-dihydroxy-2-(4-methylthiophen-3-yl)-5-(trifluoromethyl)-[1,1'-biphenyl]-3-carboximidamide; 2-(2,4-dimethylthiophen-3-yl)-N',4'-dihydroxy-5-(trifluoromethyl)-[1,1'-biphenyl]-3-carboximidamide; N',4'-dihydroxy-2-iodo-5-(trifluoromethyl)-[1,1'-biphenyl]-3-carboximidamide; 2",5"-difluoro-N',4-dihydroxy-5'-propyl-[1,1':2',1"-terphenyl]-3'-carboximidamide; 2-(1,3-dimethyl-1H-pyrrol-2-yl)-N',4'-dihydroxy-5-propyl-[1,1'-biphenyl]-3-carboximidamide; 3",5"-di fluoro-N',4-dihydroxy-5'-propyl-[1,1':2',1'-terphenyl]-3'-carboximidamide; 2-(2,4-dimethylfuran-3-yl)-N',4'-dihydroxy-5-(trifluoromethyl)-[1,1'-biphenyl]-3-carboximidamide; 3'-chloro-5'-fluoro-N',4'-dihydroxy-2-(3-methylthiophen-2-yl)-5-propyl-[1,1'-biphenyl]-3-carboximidamide; N'-hydroxy-3-(1H-indazol-5-yl)-2-(3-methylthiophen-2-yl)-5-propylbenzimidamide; 3'-fluoro-N',4'-dihydroxy-2-(3-methylthiophen-2-yl)-5-propyl-[1,1'-biphenyl]-3-carboximidamide; 3'-chloro-N',4'-dihydroxy-2-(3-methylthiophen-2-yl)-5-propyl-[1,1'-biphenyl]-3-carboximidamide; 3',5'-dichloro-N',4'-dihydroxy-2-(3-methylthiophen-2-yl)-5-propyl-[1,1'-biphenyl]-3-carboximidamide; N',4'-dihydroxy-3'-methyl-2-(3-methylthiophen-2-yl)-5-propyl-[1,1'-biphenyl]-3-carboximidamide; 2'-fluoro-N',4'-dihydroxy-2-(3-methylthiophen-2-yl)-5-propyl-[1,1'-biphenyl]-3-carboximidamide; 2',3'-difluoro-N',4'-dihydroxy-2-(3-methylthiophen-2-yl)-5-propyl-[1,1'-biphenyl]-3-carboximidamide; 2',5'-difluoro-N',4'-dihydroxy-2-(3-methylthiophen-2-yl)-5-propyl-[1,1'-biphenyl]-3-carboximidamide; N',4'-dihydroxy-2-(2-methylallyl)-5-propyl-[1,1'-biphenyl]-3-carboximidamide; 2-allyl-N',4'-dihydroxy-5-propyl-[1,1'-biphenyl]-3-carboximidamide; N',4'-dihydroxy-5-propyl-2-vinyl-[1,1'-biphenyl]-3-carboximidamide; 5-bromo-N',4'-dihydroxy-2-(1-methyl-1H-imidazol-5-yl)-[1,1'-biphenyl]-3-carboximidamide; N',4'-dihydroxy-5-propyl-2-(pyridin-2-yl)-[1,1'-biphenyl]-3-carboximidamide; N',4'-dihydroxy-2-(2-methoxythiazol-4-yl)-5-propyl-[1,1'-biphenyl]-3-carboximidamide; N',4'-dihydroxy-5-propyl-2-(thiazol-5-yl)-[1,1'-biphenyl]-3-carboximidamide; N',4'-dihydroxy-5-propyl-2-(thiazol-2-yl)-[1,1'-biphenyl]-3-carboximidamide; 5'-ethyl-N',4-dihydroxy-[1,1':2',1"-terphenyl]-3'-carboximidamide; N',4-dihydroxy-5'-isobutyl-[1,1':2',1"-terphenyl]-3'-carboximidamide; N',4-dihydroxy-5'-((E)-prop-1-en-1-yl)-[1,1':2',1"-terphenyl]-3'-carboximidamide; 5'-allyl-N',4-dihydroxy-[1,1':2',1"-terphenyl]-3'-carboximidamide; 5'-butyl-N',4-dihydroxy-[1,1':2',1"-terphenyl]-3'-carboximidamide; 2-(2,5-dimethyl-1H-pyrrol-1-yl)-N',4'-dihydroxy-5-(trifluoromethyl)-[1,1'-biphenyl]-3-carboximidamide; 4-hydroxy-5'-propyl-[1,1':2',1"-terphenyl]-3'-carbaldehyde oxime 5'-propyl-3'-(1H-pyrazol-4-yl)-[1,1':2',1"-terphenyl]-4-ol; 5-chloro-2-(3,5-dimethylisoxazol-4-yl)-N',4'-dihydroxy-3'-nitro-[1,1'-biphenyl]-3-carboximidamide; 5'-chloro-5"-fluoro-N',4-dihydroxy-2"-methyl-[1,1':2',1"-terphenyl]-3'-carboximidamide; 5'-chloro-5"-fluoro-N',4-dihydroxy-2"-methoxy-[1,1':2',1"-terphenyl]-3'-carboximidamide; 5-chloro-N',4'-dihydroxy-2-(4-methylthiophen-3-yl)-[1,1'-biphenyl]-3-carboximidamide; 5'-chloro-N',4-dihydroxy-2"-methyl-[1,1':2',1"-terphenyl]-3'-carboximidamide; 2-(2,4-dimethylthiophen-3-yl)-N',4'-dihydroxy-[1,1'-biphenyl]-3-carboximidamide; 5-chloro-2-(2,4-dimethylthiophen-3-yl)-N',4'-dihydroxy-[1,1'-biphenyl]-3-carboximidamide; 2"-chloro-5"-fluoro-N',4-dihydroxy-5'-propyl-[1,1':2',1"-terphenyl]-3'-carboximidamide; 6'-chloro-N',4-dihydroxy-5'-propyl-[1,1':2',1"-terphenyl]-3'-carboximidamide; N',4-dihydroxy-5',6'-dipropyl-[1,1':2',1"-terphenyl]-3'-carboximidamide; N',4'-dihydroxy-2-(3-methylthiophen-2-yl)-[1,1'-biphenyl]-3-carboximidamide; 5'-bromo-6'-chloro-N',4-dihydroxy-[1,1':2',1"-terphenyl]-3'-carboximidamide; 6'-chloro-N',4-dihydroxy-5'-phenyl-[1,1':2',1"-terphenyl]-3'-carboximidamide; 6'-chloro-N',4-dihydroxy-[1,1':2',1"-terphenyl]-3'-carboximidamide; N',4-dihydroxy-6'-methyl-5'-propyl-[1,1':2',1"-terphenyl]-3'-carboximidamide; 5",6'-difluoro-N',4-dihydroxy-2"-methyl-5'-propyl-[1,1':2',1"-terphenyl]-3'-carboximidamide; 5",6'-difluoro-4-hydroxy-2"-methyl-5'-propyl-[1,1':2',1"-terphenyl]-3'-carboxamide; 4-hydroxy-6'-methyl-5'-propyl-[1,1':2',1"-terphenyl]-3'-carbaldehyde oxime 5",6'-difluoro-N',4-dihydroxy-2"-methoxy-5'-propyl-[1,1':2',1"-terphenyl]-3'-carboximidamide; 5",6'-difluoro-4-hydroxy-2"-methoxy-5'-propyl-[1,1':2',1"-terphenyl]-3'-carboxamide; 6'-fluoro-4-hydroxy-5'-propyl-[1,1':2',1"-terphenyl]-3'-carboxamide; 6'-fluoro-N',4-dihydroxy-2"-methyl-5'-propyl-[1,1':2',1"-terphenyl]-3'-carboximidamide; 6-fluoro-N',4'-dihydroxy-2-(4-methylthiophen-3-yl)-5-propyl-[1,1'-biphienyl]-3-carboximidamide; 6'-fluoro-4-hydroxy-2"-methyl-5'-propyl-[1,1':2',1"-terphenyl]-3'-carboxamide; 6-fluoro-4'-hydroxy-2-(4-methylthiophen-3-yl)-5-propyl-[1,1'-biphenyl]-3-carboxamide; 2-(2,4-dimethylthiophen-3-yl)-6-fluoro-N',4'-dihydroxy-5-propyl-[1,1'-biphenyl]-3-carboxamide; 5'-chloro-5"-fluoro-4-hydroxy-2"-methoxy-[1,1':2',1"-terphenyl]-3'-carboxamide; 6'-fluoro-N',4-dihydroxy-5'-propyl-[1,1':2',1"-terphenyl]-3'-carboximidamide; 5"-fluoro-N',4-dihydroxy-2"-methoxy-[1,1':2',1"-terphenyl]-3'-carboximidamide; N',4-dihydroxy-[1,1':2',1"-terphenyl]-3'-carboximidamide; 5"-fluoro-N',4-di hydroxy-2"-methyl-[1,1':2',1"-terphenyl]-3'-carboximidamide; N',4-dihydroxy-5'-(trifluoromethyl)-2"-vinyl-[1,1':2',1"-terphenyl]-3'-carboximidamide; 2"-ethyl-N',4-dihydroxy-5'-(trifluoromethyl)-[1,1':2',1"-terphenyl]-3'-carboximidamide; 3"-fluoro-N',4-dihydroxy-2"-methyl-5'-(trifluoromethyl)-[1,1':2',1"-terphenyl]-3'-carboximidamide; 3"-fluoro-N',4-dihydroxy-2"-methoxy-5'-(trifluoromethyl)-[1,1'2.1"-terphenyl]-3'-carboximidamide; 5',6'-dichloro-5"-fluoro-N',4-dihydroxy-2"-methyl-[1,1':2',1"-terphenyl]-3'-carboximidamide; 3",5"-di fluoro-N',4-dihydroxy-5'-(trifluoromethyl)-[1,1':2',1"-terphenyl]-3'-carboximidamide; 5"-chloro-N',4-dihydroxy-2"-methoxy-5'-trifluoromethyl)-[1,1':2',1"-terphenyl]-3-carboximidamide; 2"-ethynyl-N',4-dihydroxy-5'-(trifluoromethyl)-[1,1':2',1"-terphenyl]-3'-carboximidamide; 3"-chloro-5"-fluoro-N',4-dihydroxy-5'-(trifluoromethyl)-[1,1':2',1"-terphenyl]-3'-carboximidamide; 5"-fluoro-N',4-dihydroxy-2",5'-bis(trifluoromethyl)-[1,1':2',1"-terphenyl]-3'-carboximidamide; 3",5"-difluoro-N',4-dihydroxy-2"-methoxy-5'-(trifluoromethyl)-[1,1':2',1"-terphenyl]-3'-carboximidamide; 5'-methyl-3'-(1H-pyrazol-4-yl)-[1,1':2',1"-terphenyl]-4-ol; 3",5'-difluoro-5'-propyl-3'-(1H-pyrazol-4-yl)-[1,1':2',1"-terphenyl]-4-ol; N',4-dihydroxy-5'-phenyl-[1,1':2',1"-terphenyl]-3'-carboximidamide; 5'-benzyl-N',4-dihydroxy-[1,1':2',1"-terphenyl]-3'-carboximidamide; N',4-dihydroxy-5'-phenethyl-[1,1':2',1"-terphenyl]-3'-carboximidamide; 2,5"-difluoro-N',4-dihydroxy-2"-methyl-5'-(trifluoromethyl)-[1,1':2',1"-terphenyl]-3'-carboximidamide; 2,5"-difluoro-N',4-dihydroxy-2"-methoxy-5'-(trifluoromethyl)-[1,1':2',1"-terphenyl]-3'-carboximidamide; 2-fluoro-N',4-dihydroxy-2"-methyl-5'-(trifluoromethyl)-[1,1':2',1"-terphenyl]-3'-carboximidamide; 2-fluoro-N',4-dihydroxy-5'-(trifluoromethyl)-[1,1':2',1"-terphenyl]-3'-carboximidamide; 5"-chloro-2-fluoro-N',4-dihydroxy-2"-methoxy-5'-(trifluoromethyl)-[1,1':2',1"-terphenyl]-3'-carboximidamide; 2,3"-difluoro-N',4-dihydroxy-2"-methoxy-5'-(trifluoromethyl)-[1,1':2',1"-terphenyl]-3'-carboximidamide; 2,3",5"-trifluoro-N',4-dihydroxy-5'-(trifluoromethyl)-[1,1':2',1"-terphenyl]-3'-carboximidamide; 2-fluoro-N',4-dihydroxy-5'-(trifluoromethyl)-2"-vinyl-[1,1':2',1"-terphenyl]-3'-carboximidamide; 5"-chloro-2-fluoro-4-hydroxy-2"-methoxy-5'-(trifluoromethyl)-[1,1':2',1"-terphenyl]-3'-carboxamide; 2-fluoro-4-hydroxy-5'-(trifluoromethyl)-2"-vinyl-[1,1':2',1"-terphenyl]-3'-carboxamide; 3"-chloro-2,5"-difluoro-N',4-dihydroxy-5'-(trifluoromethyl)-)-[1,1':2',1"-terphenyl]-3'-carboximidamide; 3"-chloro-2,5"-difluoro-4-hydroxy-5'-(trifluoromethyl)-[1,1':2',1"-terphenyl]-3'-carboxamide; 2"-ethynyl-2-fluoro-N',4-dihydroxy-5'-(trifluoromethyl)-[1,1'2.1"-terphenyl]-3'-carboximidamide; 5'-chloro-3",5"-difluoro-N',4-dihydroxy-[1,1':2',1"-terphenyl]-3'-carboximidamide; 5'-chloro-3"-fluoro-N',4-dihydroxy-2"-methoxy-[1,1':2',1"-terphenyl]-3'-carboximidamide; 5',5"-dichloro-N',4-dihydroxy-2"-methoxy-[1,1':2',1"-terphenyl]-3'-carboximidamide; 3"-chloro-2-fluoro-N',4-dihydroxy-2"-methyl-5'-(trifluoromethyl)-[1,1':2',1"-terphenyl]-3'-carboximidamide; 3"-chloro-2-fluoro-4-hydroxy-2"-methyl-5'-(trifluoromethyl)-[1,1':2',1"-terphenyl]-3'-carboxamide; N',4-dihydroxy-5'-methyl-2"-vinyl-[1,1':2',1"-terphenyl]-3'-carboximidamide; 3",5"-difluoro-N',4-dihydroxy-2"-methoxy-5'-methyl-[1,1'2,1"-terphenyl]-3'-carboximidamide; 3"-fluoro-N',4-dihydroxy-2"-methoxy-5'-methyl-[1,1':2',1"-terphenyl]-3'-carboximidamide; 5"-fluoro-N',4-dihydroxy-2"-methoxy-5'-methyl-[1,1':2',1"-terphenyl]-3'-carboximidamide; 3"-chloro-5"-fluoro-N',4-dihydroxy-5'-methyl-[1,1':2',1"-terphenyl]-3'-carboximidamide; 5"-chloro-N',4-dihydroxy-2",5'-dimethyl-[1,1':2',1"-terphenyl]-3'-carboximidamide; 5"-chloro-N',4-dihydroxy-2"-methyl-5'-(trifluoromethyl)-[1,1':2',1"-terphenyl]-3'-carboximidamide; 3"-chloro-N',4-dihydroxy-2"-methyl-5'-(trifluoromethyl)-[1,1':2',1"-terphenyl]-3'-carboximidamide; 5"-chloro-N',4-dihydroxy-2"-methoxy-5'-methyl-[1,1':2',1"-terphenyl]-3'-carboximidamide; 2"-chloro-5"-fluoro-N',4-dihydroxy-5'-methyl-[1,1':2',1"-terphenyl]-3'-carboximidamide; N',4-dihydroxy-5'-methyl-[1,1':2',1"-terphenyl]-3'-carboximidamide; N',4-dihydroxy-3",5'-dimethyl-[1,1':2',1'-terphenyl]-3'-carboximidamide; 3"-chloro-N',4-di hydroxy-5'-methyl-[1,1':2',1"-terphenyl]-3'-carboximidamide; N',4-dihydroxy-3"-methoxy-5'-methyl-[1,1':2',1"-terphenyl]-3'-carboximidamide; 4"-fluoro-N',4-dihydroxy-5'-(trifluoromethyl)-[1,1':2',1"-terphenyl]-3'-carboximidamide; 4"-chloro-N',4-dihydroxy-5'-(trifluoromethyl)-[1,1':2',1"-terphenyl]-3'-carboximidamide; N',4-dihydroxy-2"-methoxy-5'-(trifluoromethyl)-[1,1':2',1"-terphenyl]-3'-carboximidamide; 4"-fluoro-N',4-dihydroxy-2"-methoxy-5'-(trifluoromethyl)-[1,1':2',1"-terphenyl]-3'-carboximidamide; N',4-dihydroxy-2"-isopropyl-5'-(trifluoromethyl)-[1,1':2',1"-terphenyl]-3'-carboximidamide; 2-(3,5-dimethylisoxazol-4-yl)-N',4'-dihydroxy-5-(trifluoromethyl)-[1,1'-biphenyl]-3-carboximidamide; 2-(3,5-dimethylisoxazol-4-yl)-4'-hydroxy-5-(trifluoromethyl)-[1,1'-biphenyl]-3-carboxamide; 3"-chloro-4-hydroxy-2"-methyl-5'-(trifluoromethyl)-[1,1':2',1"-terphenyl]-3'-carboxamide; N',4-dihydroxy-2",5"-dimethyl-5'-(trifluoromethyl)-[1,1':2',1"-terphenyl]-3'-carboximidamide; N',4-dihydroxy-2"-methoxy-5"-methyl-5'-(trifluoromethyl)-[1,1':2',1"-terphenyl]-3'-carboximidamide; 2"-chloro-N',4-dihydroxy-5"-methyl-5'-(trifluoromethyl)-[1,1':2',1"-terphenyl]-3'-carboximidamide; 5'-fluoro-N',4-dihydroxy-[1,1':2',1"-terphenyl]-3'-carboximidamide; 5"-chloro-5'-fluoro-N',4-dihydroxy-2"-methoxy-[1,1':2',1"-terphenyl]-3'-carboximidamide; 3",5'-difluoro-N',4-dihydroxy-2"-methoxy-[1,1':2',1"-terphenyl]-3'-carboximidamide; 3",5',5"-trifluoro-N',4-dihydroxy-[1,1':2',1"-terphenyl]-3'-carboximidamide; 3"-chloro-5',5"-difluoro-N',4-dihydroxy-[1,1':2',1"-terphenyl]-3'-carboximidamide; 5'-fluoro-N',4-dihydroxy-2"-vinyl-[1,1':2',1"-terphenyl]-3'-carboximidamide; 5'-chloro-N',4-dihydroxy-2",5"-dimethyl-[1,1':2',1"-terphenyl]-3'-carboximidamide; N',4-dihydroxy-2",5"-dimethyl-[1,1':2',1"-terphenyl]-3'-carboximidamide; 2"-chloro-4-hydroxy-5"-methyl-5'-(trifluoromethyl)-[1,1':2',1"-terphenyl]-3'-carboxamide; 3"-chloro-N',4-dihydroxy-5"-methyl-5'-(trifluoromethyl)-[1,1':2',1"-terphenyl]-3'-carboximidamide; 2",5"-dichloro-N',4-dihydroxy-5'-(trifluoromethyl)-[1,1':2',1"-terphenyl]-3'-carboximidamide; 5"-chloro-N',4-dihydroxy-2"-methyl-[1,1':2',1"-terphenyl]-3'-carboximidamide; 5"-chloro-N',4-dihydroxy-2"-methoxy-[1,1':2',1"-terphenyl]-3'-carboximidamide; 3",5'-di fluoro-N',4-dihydroxy-5'-methyl-[1,1':2',1"-terphenyl]-3'-carboximidamide; 3",5"-difluoro-4-hydroxy-5'-methyl-[1,1':2',1"-terphenyl]-3'-carboxamide; 3"-chloro-4-hydroxy-5"-methyl-5'-(trifluoromethyl)-[1,1':2',1"-terphenyl]-3'-carboxamide; 2",5"-dichloro-4-hydroxy-5'-(trifluoromethyl)-[1,1':2',1"-terphenyl]-3'-carboxamide; 3",5"-dichloro-N',4-dihydroxy-5'-(trifluoromethyl)-[1,1':2',1"-terphenyl]-3'-carboximidamide; 3",5"-dichloro-N',4-dihydroxy-5'-methyl-[1,1':2',1"-terphenyl]-3'-carboximidamide; 2-(3,5-dimethylisoxazol-4-yl)-2'-fluoro-N',4'-dihydroxy-5-(trifluoromethyl)-[1,1'-biphenyl]-3-carboximidamide; 2-(3,5-dimethylisoxazol-4-yl)-2'-fluoro-4'-hydroxy-5-(trifluoromethyl)-[1,1'-biphenyl]-3-carboxamide; 3",5"-difluoro-N',4-dihydroxy-[1,1':2',1"-terphenyl]-3'-carboximidamide; 3",5"-difluoro-4-hydroxy-[1,1':2',1"-terphenyl]-3'-carboxamide; 3"-fluoro-N',4-dihydroxy-2"-methoxy-[1,1':2',1"-terphenyl]-3'-carboximidamide; 3"-fluoro-4-hydroxy-2"-methoxy-[1,1':2',1"-terphenyl]-3'-carboxamide; 2"-ethyl-N',4-dihydroxy-[1,1':2',1"-terphenyl]-3'-carboximidamide; 4"-chloro-2"-fluoro-N',4-dihydroxy-5'-methyl-[1,1':2',1"-terphenyl]-3'-carboximidamide; 4"-chloro-3"-fluoro-N',4-dihydroxy-5'-methyl-[1,1':2',1"-terphenyl]-3'-carboximidamide; N',4-dihydroxy-2"-methoxy-[1,1':2',1"-terphenyl]-3'-carboximidamide; 5'-chloro-N',4-dihydroxy-2"-methoxy-[1,1':2',1"-terphenyl]-3'-carboximidamide; 4"-fluoro-N',4-dihydroxy-2"-methoxy-[1,1':2',1"-terphenyl]-3'-carboximidamide; 5'-chloro-4"-fluoro-N',4-dihydroxy-2"-methoxy-[1,1':2',1"-terphenyl]-3'-carboximidamide; 3"-chloro-N',4-dihydroxy-5',5"-dimethyl-[1,1':2',1"-terphenyl]-3'-carboximidamide; 2",5"-dichloro-N',4-dihydroxy-5'-methyl-[1,1':2',1"-terphenyl]-3'-carboximidamide; 3",5"-difluoro-4-hydroxy-5'-(trifluoromethyl)-[1,1':2',1"-terphenyl]-3'-carboxamide; N',4-dihydroxy-4",5'-dimethyl-[1,1':2',1"-terphenyl]-3'-carboximidamide; N',4-dihydroxy-2",4",5'-trimethyl-[1,1':2',1"-terphenyl]-3'- carboximidamide; 4"-fluoro-N',4-di hydroxy-5'-methyl-[1,1':2',1"-terphenyl]-3'-carboximidamide; 2",4"-difluoro-N',4-dihydroxy-5'-methyl-[1,1':2',1"-terphenyl]-3'-carboximidamide; 5"-chloro-5'-fluoro-N',4-dihydroxy-2"-methyl-[1,1':2'.1'-terphenyl]-3'-carboximidamide; 5',5"-difluoro-N',4-dihydroxy-2"-methoxy-[1,1':2',1"-terphenyl]-3'-carboximidamide; 2"-chloro-5'-fluoro-N',4-dihydroxy-5"-methyl-[1,1':2',1"-terphenyl]-3'-carboximidamide; 2",5"-dichloro-5'-fluoro-N',4-dihydroxy-[1,1':2',1"-terphenyl]-3'-carboximidamide; 5'-fluoro-N',4-dihydroxy-2"-methoxy-[1,1':2',1"-terphenyl]-3'-carboximidamide; 4",5'-difluoro-N',4-dihydroxy-2"-methoxy-[1,1':2',1"-terphenyl]-3'-carboximidamide; 5'-fluoro-N',4-dihydroxy-2",5"-dimethyl-[1,1':2',1"-terphenyl]-3'-carboximidamide; 5'-fluoro-N',4-dihydroxy-2"-methoxy-5"-methyl-[1,1':2' 1"-terphenyl]-3'-carboximidamide; N',4-dihydroxy-2"-methoxy-5"-methyl-[1,1':2',1"-terphenyl]-3'-carboximidamide; N',4-dihydroxy-2"-methoxy-5',5"-dimethyl-[1,1':2',1'-terphenyl]-3'-carboximidamide; 4"-fluoro-N',4-dihydroxy-2"-methoxy-5'-methyl-[1,1':2',1"-terphenyl]-3'-carboximidamide; 2"-chloro-N',4-dihydroxy-5',5'-dimethyl-[1,1':2',1"-terphenyl]-3'-carboximidamide; N',4-dihydroxy-5'-methyl-2"-(trifluoromethoxyl)-[1,1':2',1"-terphenyl]-3'-carboximidamide; N',4-dihydroxy-2"-methoxy-5'-methyl-[1,1':2',1"-terphenyl]-3'-carboximidamide; 3",5"-difluoro-N',4-dihydroxy-5'-methoxy-[1,1':2',1"-terphenyl]-3'-carboximidamide; 5"-fluoro-N',4-dihydroxy-2",5'-dimethoxy-[1.1':2',1"-terphenyl]-3'-carboximidamide; 2-(5-fluoro-2-methoxypyridin-3-yl)-N',4-dihydroxy-5-methyl-[1,1'-biphenyl]-3-carboximidamide; N',4-dihydroxy-5-methyl-2-(2-methylpyridin-3-yl)-[1,1'-biphenyl]-3-carboximidamide; N',4-dihydroxy-2-(2-methoxypyridin-3-yl)-5-methyl-[1,1'-biphenyl]-3-carboximidamide; 2-(3,5-dimethylisothiazol-4-yl)-N',4-dihydroxy-5-methyl-[1,1'-biphenyl]-3-carboximidamide; N',4-dihydroxy-5'-methoxy-[1,1':2',1"-terphenyl]-3'-carboximidamide; 2-(3,5-dimethylisothiazol-4-yl)-4'-hydroxy-5-methyl-[1,1'-biphenyl]-3-carboxamide; 5-chloro-2-(5-fluoro-2-methoxypyridin-3-yl)-N',4'-di hydroxy-[1,1'-biphenyl]-3-carboximidamide; 2-(5-fluoro-2-methoxypyridin-3-yl)-4'-hydroxy-5-methyl-[1,1'-biphenyl]-3-carboxamide; 2-(3,5-dimethylisothiazol-4-yl)-N',4'-dihydroxy-5-(trifluoromethyl)-[1,1'-biphenyl]-3-carboximidamide; 5-chloro-2-(3,5-dimethylisothiazol-4-yl)-N',4'-dihydroxy-[1,1'-biphenyl]-3-carboximidamide; 4"-fluoro-N',4-dihydroxy-2"-methyl-5'-(trifluoromethyl)-[1,1':2',1"-terphenyl]-3'-carboximidamide; 2",4"-difluoro-N',4-dihydroxy-5'-(trifluoromethyl)-[1,1':2',1"-terphenyl]-3'-carboximidamide; N',4-dihydroxy-2-(4-methylpyridin-3-yl)-5-(trifluoromethyl)-[1,1'-biphenyl]-3-carboximidamide; 2-(2,5-dimethylpyridin-3-yl)-N',4-dihydroxy-5-(trifluormethyl)-[1,1'-biphenyl]-3-carboximidamide; 2"-chloro-4"-fluoro-N',4-dihydroxy-5'-(trifluoromethyl)-[1,1':2',1"-terphenyl]-3'-carboximidamide; 4",5'-difluoro-N',4-dihydroxy-2"-methyl-5'-(trifluoromethyl)-)-[1,1':2',1"-terphenyl]-3'-carboximidamide; 2",5"-difluoro-N',4-dihydroxy-5'-(trifluoromethyl)-[1,1':2',1"-terphenyl]-3'-carboximidamide; N',4-dihydroxy-2-(pyridin-3-yl)-5-(trifluormethyl)-[1,1'-biphenyl]-3-carboximidamide; 2-(2,3-dihydrobenzofuran-7-yl)-N',4-dihydroxy-5-(trifluoromethyl)-[1,1'-biphenyl]-3-carboximidamide; 2-(benzofuran-7-yl)-N',4-dihydroxy-5-(trifluoromethyl)-[1,1'-biphenyl]-3-carboximidamide; N',4-dihydroxy-2-(1-methyl-1H-indol-7-yl)-5-(trifluoromethyl)-[1,1'-biphenyl]-3-carboximidamide; 2"-chloro-5"-fluoro-N',4-dihydroxy-5'-(trifluoromethyl)-[1,1':2',1"-terphenyl]-3'-carboximidamide; 5"-chloro-2"-fluoro-N',4-dihydroxy-5'-(trifluromethyl)-[1,1':2',1"-terphenyl]-3'-carboximidamide; 2-(4-fluorobenzofuran-7-yl)-N',4-dihydroxy-5-(trifluoromethyl)-[1,1'-biphenyl]-3-carboximidamide; 3",4"-difluoro-N',4-dihydroxy-5'-(trifluoromethyl)-[1,1':2',1"-terphenyl]-3'-carboximidamide; 5'-chloro-2",4"-difluoro-N',4-dihydroxy-[1,1':2',1"-terphenyl]-3'-carboximidamide; 5'-chloro-2",5"-difluoro-N',4-dihydroxy-[1,1':2',1"-terphenyl]-3'-carboximidamide; 2-(benzo[d][1,3]dioxol-4-yl)-N',4'-dihydroxy-5-(trifluoromethyl)-[1,1'-biphenyl]-3-carboximidamide; 3",4",5"-trifluoro-N',4-dihydroxy-5'-(trifluoromethyl)-[1,1':2',1"-terphenyl]-3'-carboximidamide; 5'-chloro-3",4"-difluoro-N',4-dihydroxy-[1,1':2',1"-terphenyl]-3'-carboximidamide; 5'-chloro-3",4",5"-trifluoro-N',4-dihydroxy-[1,1':2',1"-terphenyl]-3'-carboximidamide; 5-chloro-N',4'-dihydroxy-2-(4-methylpyridin-3-yl)-[1,1'-biphenyl]-3-carboximidamide; 5',5"-dichloro-2"-fluoro-N',4-dihydroxy-[1,1':2',1"-terphenyl]-3'-carboximidamide; 2",5'-dichloro-5"-fluoro-N',4-dihydroxy-[1,1':2',1"-terphenyl]-3'-carboximidamide; 5'-chloro-2"-fluoro-N',4-dihydroxy-5"-methyl-[1,1':2',1"-terphenyl]-3'-carboximidamide; 5'-chloro-2"-fluoro-N',4-dihydroxy-4"-methyl-[1,1':2',1"-terphenyl]-3'-carboximidamide; 2-(5-fluoro-2-methoxypyridin-3-yl)-N',4'-dihydroxy-5-(trifluoromethyl)-[1,1'-biphenyl]-3-carboximidamide; 5'-chloro-N',4-dihydroxy-2",4"-dimethoxy-[1,1':2',1"-terphenyl]-3'-carboximidamide; 5'-chloro-4-hydroxy-2",4"-dimethoxy-[1,1':2',1"-terphenyl]-3'-carbonitrile; 5-chloro-2-(5-chloro-2-methoxypyridin-3-yl)-N',4'-dihydroxy-[1,1'-biphenyl]-3-carboximidamide; 5-chloro-2-(5-chloro-2-methoxypyridin-3-yl)-4'-hydroxy-[1,1'-biphenyl]-3-carboxamide; 5-chloro-2-(2,5-dimethylpyridin-3-yl)-N',4'-dihydroxy-[1,1'-biphenyl]-3-carboximidamide; 5-chloro-2-(2,5-dimethylpyridin-3-yl)-4'-hydroxy-[1,1'-biphenyl]-3-carboxamide; 2-(benzo[d][1,3]dioxol-4-yl)-5-chloro-N',4'-dihydroxy-[1,1'-biphenyl]-3-carboximidamide; 5-chloro-N',4'-dihydroxy-2-(naphthalen-2-yl)-[1,1'-biphenyl]-3-carboximidamide; 5-chloro-N',4'-dihydroxy-2-(isoquinolin-6-yl)-[1,1'-biphenyl]-3-carboximidamide; 5-chloro-N',4'-dihydroxy-2-(quinolin-6-yl)-[1,1'-biphenyl]-3-carboximidamide; 5-chloro-N',4'-dihydroxy-2-(1-methyl-1H-benzo[d]imidazol-5-yl)-[1,1'-biphenyl]-3-carboximidamide; 5-chloro-4'-hydroxy-2-(1-methyl-1H-benzo[d]imidazol-5-yl)-[1,1'-biphenyl]-3-carboxamide; 2-(5-chloro-2-methoxypyridin-3-yl)-N',4'-dihydroxy-5-(trifluoromethyl)-[1,1'-biphenyl]-3-carboximidamide; 2"-fluoro-N',4-dihydroxy-5"-methyl-5'-(trifluoromethyl)-[1,1':2',1"-terphenyl]-3'-carboximidamide; 5-chloro-2-(6-chloro-2-methoxypyridin-3-yl)-N',4'-dihydroxy-[1,1'-biphenyl]-3-carboximidamide; 5-chloro-N',4'-dihydroxy-2-(2-methoxy-5-methylpyridin-3-yl)-[1,1'-biphenyl]-3-carboximidamide; 5-chloro-2-(cyclopent-1-en-1-yl)-N',4'-dihydroxy-[1,1'-biphenyl]-3-carboximidamide; 5-chloro-2-(cyclopent-1-en-1-yl)-4'-hydroxy-[1,1'-biphenyl]-3-carboxamide; 2-(cyclopent-1-en-1-yl)-N',4'-dihydroxy-5-(trifluoromethyl)-[1,1'-biphenyl]-3-carboximidamide; 2-(cyclopent-1-en-1-yl)-4'-hydroxy-5-(trifluoromethyl)-[1,1'-biphenyl]-3-carboxamide; 5'-bromo-5"-fluoro-N',4-dihydroxy-2"-methoxy-[1,1':2',1'-terphenyl]-3'-carboximidamide; 5'-bromo-5"-fluoro-N',4-dihydroxy-2"-methyl-[1,1':2',1"-terphenyl]-3'-carboximidamide; 5'-bromo-3"-fluoro-N',4-dihydroxy-2"-methoxy-[1,1':2',1"-terphenyl]-3'-carboximidamide; 5'-bromo-N',4-dihydroxy-2",5"-dimethyl-[1,1':2',1"-terphenyl]-3'-carboximidamide; 5'-bromo-N',4-dihydroxy-5"-methoxy-2"-methyl-[1,1':2',1"-terphenyl]-3'-carboximidamide; 5'-bromo-N',4-dihydroxy-2"-methoxy-[1,1':2',1"-terphenyl]-3'-carboximidamide; 5'-bromo-4"-fluoro-N',4-dihydroxy-2"-methoxy-[1,1':2',1"-terphenyl]-3'-carboximidamide; 5"-fluoro-N',4-dihydroxy-5'-(trifluoromethyl)-2"-vinyl-[1,1':2',1"-terphenyl]-3'-carboximidamide; 2,5"-difluoro-N',4- dihydroxy-5'-(trifluoromethyl)-2"-vinyl-[1,1':2',1"-terphenyl]-3'-carboximidamide; 5"-chloro-N',4-dihydroxy-5'-(trifluoromethyl)-2"-vinyl-[1,1':2',1"-terphenyl]-3'-carboximidamide; 2"-ethynyl-5"-fluoro-N',4-dihydroxy-5'-(trifluoromethyl)-[1,1':2',1"-terphenyl]-3'-carboximidamide; 4-hydroxy-2"-methoxy-5"-methyl-5'-(trifluoromethyl)-[1,1':2',1"-terphenyl]-3'-carboxamide; 5'-bromo-5"-chloro-N',4-dihydroxy-2"-methyl-[1,1':2',1"-terphenyl]-3'-carboximidamide; 5'-bromo-3",5"-difluoro-N',4-dihydroxy-[1,1':2',1"-terphenyl]-3'-carboximidamide; 5'-bromo-3"-chloro-5"-fluoro-N',4-dihydroxy-[1,1':2',1"-terphenyl]-3'-carboximidamide; 5'-bromo-2"-chloro-5"-fluoro-N',4-dihydroxy-[1,1':2',1"-terphenyl]-3'-carboximidamide; 5'-bromo-4"-chloro-N',4-dihydroxy-[1,1':2',1"-terphenyl]-3'-carboximidamide; 5'-bromo-2",5"-dichloro-N',4-dihydroxy-[1,1':2',1"-terphenyl]-3'-carboximidamide; 5'-bromo-2"-chloro-N',4-dihydroxy-5"-methyl-[1,1':2',1"-terphenyl]-3'-carboximidamide; 5-bromo-2-(3,5-dimethylisoxazol-4-yl)-N',4'-dihydroxy-[1,1'-biphenyl]-3-carboximidamide; 3-chloro-5-fluoro-N',4-dihydroxy-5'-(trifluoromethyl)-[1,1':2',1"-terphenyl]-3'-carboximidamide; 3-chloro-5-fluoro-4-hydroxy-5'-(trifluoromethyl)-[1,1':2',1"-terphenyl]-3'-carboxamide; 3,5'-dichloro-3",5,5"-trifluoro-N',4-dihydroxy-[1,1':2',1"-terphenyl]-3'-carboximidamide; 3'-chloro-2-(3,5-dimethylisoxazol-4-yl)-5'-fluoro-N',4'-dihydroxy-5-(trifluoromethyl)-[1,1'-biphenyl]-3-carboximidamide; 3-chloro-3",5,5"-trifluoro-N',4-dihydroxy-5'-(trifluoromethyl)-[1,1':2',1"-terphenyl]-3'-carboximidamide; 3-chloro-5,5"-difluoro-N',4-dihydroxy-2"-methoxy-5'-(trifluoromethyl)-[1,1':2',1"-terphenyl]-3'-carboximidamide; 3-chloro-5-fluoro-N',4-di hydroxy-2"-methoxy-5'-(trifluoromethyl)-[1':2',1"-terphenyl]-3'-carboximidamide; 5'-chloro-3",5"-difluoro-N'-hydroxy-4-methoxy-3-methylyl-[1,1':2',1"-terphenyl]-3'-carboximidamide; 5'-chloro-3",5"-di fluoro-N',4-dihydroxy-3-methyl-[1,1':2',1"-terphenyl]-3'-carboximidamide; 5-chloro-2-(3,5-dimethylisoxazol-4-yl)-N',4'-dihydroxy-3'-methyl-[1,1'-biphenyl]-3-carboximidamide; 5'-chloro-N',4-dihydroxy-2",3-dimethyl-[1,1':2',1"-terphenyl]-3'-carboximidamide; 5'-chloro-5"-fluoro-N',4-dihydroxy-2"-methoxy-3-methyl-[1,1':2',1"-terphenyl]-3'-carboximidamide; 5'-chloro-5"-fluoro-4-hydroxy-2"-methoxy-3-methyl-[1,1':2',1"-terphenyl]-3'-carboxamide; 5'-chloro-3",5"-difluoro-N',4-dihydroxy-3-isopropyl-[1,1':2',1"-terphenyl]-3'-carboximidamide; 2'-(3,5-dimethylisoxazol-4-yl)-3'-(1H-1,2,3-triazol-4-yl)-5'-(trifluoromethyl)-[1,1'-biphenyl]-4-ol; N',4-dihydroxy-5'-(trifluoromethoxyl)-[1,1':2',1"-terphenyl]-3'-carboximidamide; 3",5"-difluoro-N',4-dihydroxy-5'-(trifluoromethoxyl)-[1,1':2',1"-terphenyl]-3'-carboximidamide; 5"-chloro-N',4-dihydroxy-2"-methoxy-5'-(trifluoromethoxyl)-[1,1':2',1"-terphenyl]-3'-carboximidamide; 4-hydroxy-5'-(trifluoromethoxyl)-[1,1':2',1"-terphenyl]-3'-carboxamide; 3",5"-difluoro-4-hydroxy-5'-(trifluoromethoxyl)-[1,1':2',1"-terphenyl]-3'-carboxamide; N',4-dihydroxy-5'-isopropyl-[1,1':2',1"-terphenyl]-3'-carboximidamide; 3",5"-difluoro-N',4-dihydroxy-5'-isopropyl-[1,1':2',1"-terphenyl]-3'-carboximidamide; 5"-chloro-N',4-dihydroxy-5'-isopropyl-2"-methoxy-[1,1':2',1"-terphenyl]-3'-carboximidamide; 4-amino-5'-isopropyl-[1,1':2',1"-terphenyl]1-3'-carboxamide; 3",5"-difluoro-4-hydroxy-5'-isopropyl-[1,1':2',1"-terphenyl]-3'-carboxamide; 2-(3-cyanofuran-2-yl)-N',4'-dihydroxy-5-(trifluoromethyl)-[1,1'-biphenyl]-3-carboximidamide; 2-(4-cyano-1-methyl-1H-pyrazol-5-yl)-N',4'-dihydroxy-5-(trifluoromethyl)-[1,1'-biphenyl]-3-carboximidamide; 2"-cyano-N',4-dihydroxy-5'-(trifluoromethyl)-[1,1':2',1"-terphenyl]-3'-carboximidamide; 2-(3-cyano-1-methyl-1H-pyrrol-2-yl)-N',4'-dihydroxy-5-(trifluoromethyl)-[1,1'-biphenyl]-3-carboximidamide; 2'-(3,5-dimethylisoxazol-4-yl)-3'-(hydroxymethyl)-5'-(trifluoromethyl)-[1,1'-biphenyl]-4-ol; 5'-cyano-3",5"-difluoro-N',4-dihydroxy-[1,1':2',1"-terphenyl]-3'-carboximidamide; N',4'-dihydroxy-2-(pyrrolidin-1-yl)-5-(trifluoromethyl)-[1,1'-biphenyl]-3-carboximidamide; 4-chloro-3',5'-difluoro-N'-hydroxy-6-(1H-indazol-5-yl)-[1,1'-biphenyl]-2-carboximidamide; 6-(1H-benzo[d]imidazol-5-yl)-4-chloro-N'-hydroxy-[1,1'-biphenyl]-2-carboximidamide; 4-chloro-3',5'-difluoro-N'-hydroxy-6-(1H-indol-5-yl)-[1,1'-biphenyl]-2-carboximidamide; 4-chloro-3',5'-difluoro-6-(1H-indol-5-yl)-[1,1'-biphenyl]-2-carboxamide; 4-chloro-3',5'-difluoro-6-(1H-indazol-5-yl)-[1,1'-biphenyl]-2-carboxamide; 6-(1H-benzo[d]imidazol-5-yl)-4-chloro-3',5'-difluoro-[1,1'-biphenyl]-2-carboxamide; 3',5'-difluoro-N'-hydroxy-6-(1H-indol-5-yl)-4-methyl-[1,1'-biphenyl]-2-carboximidamide; 3',5'-difluoro-N'-hydroxy-6-(1H-indol-6-yl)-4-methyl-[1,1'-biphenyl]-2-carboximidamide; 3',5'-difluoro-N'-hydroxy-6-(1H-indazol-5-yl)-4-methyl-[1,1'-biphenyl]-2-carboximidamide; 3',5'-difluoro-N'-hydroxy-6-(1H-indazol-5-yl)-4-propyl-[1,1'-biphenyl]-2-carboximidamide; 3',5'-difluoro-N'-hydroxy-6-(1H-indol-5-yl)-4-propyl-[1,1'-biphenyl]-2-carboximidamide; 3',5'-difluoro-N'-hydroxy-6-(1H-indazol-5-yl)-4-(trifluoromethyl)-[1,1'-biphenyl]-2-carboximidamide; 3',5'-difluoro-N'-hydroxy-6-(1H-indol-6-yl)-4-(trifluoromethyl)-[1,1'-biphenyl]-2-carboximidamide; 3',5'-difluoro-N'-hydroxy-6-(1H-indazol-6-yl)-4-(trifluoromethyl)-[1,1'-biphenyl]-2-carboximidamide; 3',5'-difluoro-N'-hydroxy-6-(1H-indol-5-yl)-4-(trifluoromethyl)-[1,1'-biphenyl]-2-carboximidamide; 3',5'-difluoro-6-(1H-indol-5-yl)-4-(trifluoromethyl)-[1,1'-biphenyl]-2-carboxamide; 3',5'-difluoro-N'-hydroxy-6-(1H-indazol-6-yl)-4-propyl-[1,1'-biphenyl]-2-carboximidamide; N'-hydroxy-6-(1H-indazol-5-yl)-2'-methoxy-5'-methyl-4-(trifluoromethyl)-[1,1'-biphenyl]-2-carboximidamide; 5'-chloro-N'-hydroxy-6-(1H-indol-5-yl)-2'-methoxy-4-(trifluoromethyl)-[1,1'-biphenyl]-2-carboximidamide; 5'-chloro-N'-hydroxy-6-(1H-indazol-5-yl)-2'-methoxy-4-(trifluoromethyl)-[1,1'-biphenyl]-2-carboximidamide; 2',5'-difluoro-N'-hydroxy-6-(1H-indazol-5-yl)-4-(trifluoromethyl)-[1,1'-biphenyl]-2-carboximidamide; 3',5'-difluoro-6-(6-fluoro-1H-indol-5-yl)-N'-hydroxy-4-(trifluoromethyl)-[1,1'-biphenyl]-2-carboximidamide; N'-hydroxy-3-(1H-indazol-5-yl)-2-(naphthalen-1-yl)-5-(trifluoromethyl)benzimidamide; 2-(benzo[d][1,3]dioxol-4-yl)-N'-hydroxy-3-(1H-indazol-5-yl)-5-(trifluoromethyl)benzimidamide; 4'-fluoro-N'-hydroxy-6-(1H-indazol-5-yl)-2'-methoxy-4-(trifluoromethyl)-[1,1'-biphenyl]-2-carboximidamide; N'-hydroxy-6-(1H-indazol-5-yl)-3'-methyl-4-(trifluoromethyl)-[1,1'-biphenyl]-2-carboximidamide; 3',4',5'-trifluoro-N'-hydroxy-6-(1H-indazol-5-yl)-4-(trifluoromethyl)-[1,1'-biphenyl]-2-carboximidamide; 3',4'-difluoro-N'-hydroxy-6-(1H-indazol-5-yl)-4-(trifluoromethyl)-[1,1'-biphenyl]-2-carboximidamide; N'-hydroxy-3-(1H-indazol-5-yl)-2-(2-methoxypyridin-3-yl)-5-(trifluoromethyl)benzimidamide; 2-(cyclopent-1-en-1-yl)-N'-hydroxy-3-(1H-indazol-5-yl)-5-(trifluoromethyl)benzimidamide; 2-(3,5-dimethylisoxazol-4-yl)-N'-hydroxy-3-(1H-indazol-5-yl)-5-(trifluoromethyl)benzimidamide; or 2',4'-difluoro-N'-hydroxy-6-(1H-indazol-5-yl)-4-(trifluoromethyl)-[1,1'-biphenyl]-2-carboximidamide.

The ERβ ligand may be 2-Bromo-1-(4-hydroxy-phenyl)-1H-indole-3-carbonitrile; 1-(4-Hydroxy-phenyl)-2-thiophen-3-yl-1H-indole-3-carbonitrile; 2-(3-Cyano-furan-2-yl)-1-(4-hydroxy-phenyl)-1H-indole-3-carbonitrile; 1-(4-Hydroxy-phenyl)-2-pyrrol-1-yl-1H-indole-3-carbonitrile;

2-Dimethylamino-1-(4-hydroxy-phenyl)-1H-indole-3-carbonitrile; 1-(4-Hydroxy-phenyl)-2-isopropyl-1H-indole-3-carbonitrile; 2-Acetyl-1-(4-hydroxy-phenyl)-1H-indole-3-carbonitrile; 2-(3,5-Dimethyl-isoxazol-4-yl)-1-(4-hydroxyphenyl)-1H-indole-3-carboxylic acid; 1-[1-(4-Hydroxy-phenyl)-2-phenyl-1H-indol-3-yl]-ethanone; 1-(4-Hydroxy-phenyl)-2-phenyl-H-indole-3-carboxylic acid, amide; (Z)-2-(3,5-dimethyl isoxazol-4-yl)-N'-hydroxy-1-(4-hydroxyphenyl)-1H-indole-3-carboximidamide; [2-(3,5-Dimethyl-isoxazol-4-yl)-1-(4-hydroxy-phenyl)-1H-indol-3-yl]-carbamic acid tert-butyl ester; 4-[3-Amino-2-(3,5-dimethyl-isoxazol-4-yl)-indol-1-yl]-phenol; (Z)-2-(3,5-dimethylisoxazol-4-yl)-7-fluoro-N'-hydroxy-1-(4-hydroxyphenyl)-1H-indole-3-carboximidamide; (Z)-2-(5-chlorothiophen-2-yl)-N'-hydroxy-1-(4-hydroxyphenyl)-1H-indole-3-carboximidamide; 1-(2,3-Difluoro-4-hydroxy-phenyl)-2-(3,5-dimethyl-isoxazol-4-yl)-1H-indole-3-carbonitrile; 2-(3,5-dimethylisoxazol-4-yl)-1-(4-hydroxyphenyl)-1H-indole-3-carbohydrazonamide; 4-(2-(3,5-dimethylisoxazol-4-yl)-3-(1,2,4-oxadiazol-3-yl)-1H-indol-1-yl)phenol; 2-(3,5-Dimethyl-isoxazol-4-yl)-1-(4-hydroxy-phenyl)-1H-indole-3-carboxylic acid, methyl ester; 2-(3,5-Dimethyl-isoxazol-4-yl)-1-(4-hydroxy-phenyl)-1H-indole-3-carboxylic acid, hydroxyamide; 4-[2-(3,5-Dimethyl-isoxazol-4-yl)-3-methanesulfonyl-indol-1-yl]-phenol; 1-[2-(3,5-Dimethyl-isoxazol-4-yl)-1-(4-hydroxy-phenyl)-1H-indol-3-yl]-2,2,2-trifluoro-ethanone; 4-(3-bromo-2-(3,5-dimethylisoxazol-4-yl)-1H-indol-1-yl)phenol; 2-Bromo-5-fluoro-1-(4-hydroxy-phenyl)-1H-indole-3-carbonitrile; (Z)-2-(4-fluorophenoxyl)-N'-hydroxy-1-(4-hydroxyphenyl)-1H-indole-3-carboximidamide; 4-(2-(3,5-dimethylisoxazol-4-yl)-3-nitro-1H-indol-1-yl)phenol; 4-(3-(dihydroxyamino)-2-(3,5-dimethylisoxazol-4-yl)-1H-indol-1-yl)phenol; N-(2-(3,5-dimethylisoxazol-4-yl)-1-(4-hydroxyphenyl)-1H-indol-3-yl)acetamide N-(2-(3,5-dimethylisoxazol-4-yl)-1-(4-hydroxyphenyl)-1H-indol-3-yl)methanesulfonamide; 1-(2-(3,5-dimethylisoxazol-4-yl)-1-(4-hydroxyphenyl)-1H-indol-3-yl)urea; 4-(2-(3,5-dimethylisoxazol-4-yl)-3-thiocyanato-1H-indol-1-yl)phenol; (E)-2-(3,5-dimethylisoxazol-4-yl)-1-(4-hydroxyphenyl)-1H-indol-3-yl N'-hydroxycarbamimidothioate; 4-(3-benzyl-2-phenyl-1H-indol-1-yl)phenol; 2-(2-(3,5-dimethylisoxazol-4-yl)-1-(4-hydroxyphenyl)-1H-indol-3-yl)-2-oxoacetamide; (Z)-2-(2-(3,5-dimethylisoxazol-4-yl)-1-(4-hydroxyphenyl)-1H-indol-3-yl)-2-(hydroxyimino)acetamide; 2-(3,5-dimethylisoxazol-4-yl)-1-(4-hydroxyphenyl)-1H-indol-3-yl)-2-hydroxyacetamide; 2-(2-(3,5-dimethylisoxazol-4-yl)-1-(4-hydroxyphenyl)-1H-indol-3-yl)acetamide; 2-((Z)-But-1-enyl)-1-(4-hydroxy-phenyl)-1H-indole-3-carbonitrile; 1-(4-Hydroxy-phenyl)-2-(2-methyl-prop-1-enyl)-1H-indole-3-carbonitrile; 1-(2,3-Difluoro-4-hydroxy-phenyl)-2-(2-methyl-allyl)-1H-indole-3-carbonitrile; (Z)-2-(5-ethyl-3-methylisoxazol-4-yl)-N'-hydroxy-1-(4-hydroxyphenyl)-1H-indole-3-carboximidamide; 4-(2-(3,5-dimethylisoxazol-4-yl)-3-phenyl-1H-indol-1-yl)phenol; 4-(3-chloro-2-(3,5-dimethylisoxazol-4-yl)-1H-indol-1-yl)phenol; 2-(3,5-dimethylisoxazol-4-yl)-1-(4-hydroxyphenyl)-1H-indole-3-sulfonamide; 2-(3,5-dimethylisoxazol-4-yl)-1-(2-fluoro-4-hydroxyphenyl)-1H-indole-3-carboximidamide; 1-(4-Hydroxy-phenyl)-2-phenyl-1H-indole-3-carbonitrile; 1-(4-Hydroxy-phenyl)-2-methyl-1H-indole-3-carbonitrile; 2-(3-cyano-thiophen-2-yl)-1-(4-hydroxy-phenyl)-1H-indole-3-carbonitrile; 1-(4-Hydroxy-phenyl)-2-((E)-propenyl)-1H-indole-3-carbonitrile; 1-(4-Hydroxy-phenyl)-2-thiophen-2-yl-1H-indole-3-carbonitrile; 2-(3,5-Dimethyl-isoxazol-4-yl)-1-(4-hydroxy-phenyl)-1H-indole-3-carbonitrile; 1-(4-Hydroxy-phenyl)-2-pyridin-4-yl-1H-indole-3-carbonitrile; 1-(4-Hydroxy-phenyl)-2-(1-methyl-1H-pyrrol-2-yl)-1H-indole-3-carbonitrile; 1-(4-Hydroxy-phenyl)-2-(3-methyl-thiophen-2-yl)-1H-indole-3-carbonitrile; 1-(4-Hydroxy-phenyl)-2-isopropylamino-1H-indole-3-carbonitrile; 2-Ethylamino-1-(4-hydroxy-phenyl)-1H-indole-3-carbonitrile; 2-Butylamino-1-(4-hydroxy-phenyl)-1H-indole-3-carbonitrile; 1-(4-Hydroxy-phenyl)-2-piperidin-1-yl-1H-indole-3-carbonitrile; 1-(4-Hydroxy-phenyl)-2-pyrrolidin-1-yl-1H-indole-3-carbonitrile; 1-(4-Hydroxy-phenyl)-2-morpholin-4-yl-1H-indole-3-carbonitrile; 2-Diethylamino-1-(4-hydroxy-phenyl)-1H-indole-3-carbonitrile; 2-Ethynyl-1-(4-hydroxy-phenyl)-1H-indole-3-carbonitrile; 1-(4-Hydroxy-phenyl)-2-vinyl-1H-indole-3-carbonitrile; 1-(4-Hydroxy-phenyl)-1H-indole-2,3-dicarbonitrile; 1-(4-Hydroxy-phenyl)-2-prop-1-ynyl-1H-indole-3-carbonitrile; 1-(4-Hydroxy-phenyl)-2-pyridin-2-yl-1H-indole-3-carbonitrile; 1-(4-Hydroxy-phenyl)-2-(2-methyl-allyl)-1H-indole-3-carbonitrile; 1-(4-Hydroxy-phenyl)-2-((Z)-propenyl)-1H-indole-3-carbonitrile; 2-(Butyl-methyl-amino)-1-(4-hydroxy-phenyl)-1H-indole-3-carbonitrile; 1-(4-Hydroxy-phenyl)-2-((Z)-1-methyl-propenyl)-1H-indole-3-carbonitrile; 1-(4-Hydroxy-phenyl)-2-imidazol-1-yl-1H-indole-3-carbonitrile; 1-(4-Hydroxy-phenyl)-2-[1,2,4]triazol-1-yl-1H-indole-3-carbonitrile; 2-(3,5-Dimethyl-pyrazol-1-yl)-1-(4-hydroxy-phenyl)-1H-indole-3-carbonitrile; 1-(4-Hydroxy-phenyl)-2-pyrazol-1-yl-1H-indole-3-carbonitrile; 1-(4-Hydroxy-phenyl)-2-(5-methyl-imidazol-1-yl)-1H-indole-3-carbonitrile; 1-(4-Hydroxy-phenyl)-2-(5-methyl-pyrazol-1-yl)-1H-indole-3-carbonitrile; 1-(4-Hydroxy-phenyl)-2-(3-methyl-pyrazol-1-yl)-1H-indole-3-carbonitrile; 1-(4-Hydroxy-phenyl)-2-thiazol-2-yl-1H-indole-3-carbonitrile; 1-(4-Hydroxy-phenyl)-2-(2-methoxy-thiazol-4-yl)-1H-indole-3-carbonitrile; 1-(4-Hydroxy-phenyl)-2-thiazol-4-yl-1H-indole-3-carbonitrile; 1-(4-Hydroxy-phenyl)-2-(3-methyl-but-2-enyl)-1H-indole-3-carbonitrile; 2-((E)-But-1-enyl)-1-(4-hydroxy-phenyl)-1H-indole-3-carbonitrile; 1-(4-Hydroxy-phenyl)-2-(5-methyl-thiophen-2-yl)-1H-indole-3-carbonitrile; 2-(5-Acetyl-thiophen-2-yl)-1-(4-hydroxy-phenyl)-1H-indole-3-carbonitrile; 1-(4-Hydroxy-phenyl)-2-(1-methyl-1H-pyrazol-4-yl)-1H-indole-3-carbonitrile; 2-(5-Chloro-thiophen-2-yl)-1-(4-hydroxy-phenyl)-1H-indole-3-carbonitrile; 1-(4-Hydroxy-phenyl)-2-(4-methyl-thiophen-3-yl)-1H-indole-3-carbonitrile; 1-(4-Hydroxy-phenyl)-2-(4-methyl-thiophen-2-yl)-1H-indole-3-carbonitrile; 2-(4-Cyano-thiophen-3-yl)-1-(4-hydroxy-phenyl)-1H-indole-3-carbonitrile; 1-(4-Hydroxy-phenyl)-2-(2-methyl-2H-pyrazol-3-yl)-1H-indole-3-carbonitrile; 1-(4-Hydroxy-phenyl)-2-(1,3,5-trimethyl-1H-pyrazol-4-yl)-1H-indole-3-carbonitrile; 2-(2-Acetyl-pyrrol-1-yl)-1-(4-hydroxy-phenyl)-1H-indole-3-carbonitrile; 2-(2-Ethyl-pyrrol-1-yl)-1-(4-hydroxy-phenyl)-1H-indole-3-carbonitrile; 2-(2-Cyano-pyrrol-1-yl)-1-(4-hydroxy-phenyl)-1H-indole-3-carbonitrile; 1-(4-Hydroxy-phenyl)-2-(2-methyl-pyrrol-1-yl)-1H-indole-3-carbonitrile; 1-(3-Chloro-5-fluoro-4-hydroxy-phenyl)-2-phenyl-1H-indole-3-carbonitrile; 1-(3-Chloro-5-fluoro-4-hydroxy-phenyl)-2-(3-cyano-thiophen-2-yl)-1H-indole-3-carbonitrile; 1-(3-Chloro-5-fluoro-4-hydroxy-phenyl)-2-(3-cyano-furan-2-yl)-1H-indole-3-carbonitrile; 2-Bromo-1-(3-chloro-5-fluoro-4-hydroxy-phenyl)-1H-indole-3-carbonitrile; 2-Bromo-1-(2-fluoro-4-hydroxy-phenyl)-1H-indole-3-carbonitrile; 1-(2-Fluoro-4-hydroxy-phenyl)-2-phenyl-1H-indole-3-carbonitrile; 2-Bromo-1-(3-fluoro-4-hydroxy-phenyl)-1H-indole-3-carbonitrile; 2-Bromo-1-(2,3-difluoro-4-hydroxy-phenyl)-1H-indole-3-carbonitrile; 2-Bromo-1-(2,5-difluoro-4-hydroxyphenyl)-1H-indole-3-carbonitrile; 2-Bromo-1-(3-chloro-4-hydroxy-phenyl)-1H-indole-3-carbonitrile; 2-Bromo-1-(3,5-difluoro-4-hydroxy-phenyl)-1H-indole-3-carbonitrile; 1-(3-Fluoro-4-hydroxy-phenyl)-2-phenyl-1H-indole-3-carbonitrile; 1-(3,5-Difluoro-4-hydroxy-phenyl)-2-phenyl-1H-indole-3-carbonitrile; 1-(3-Chloro-4-hydroxy-phenyl)-2-phenyl-1H-indole-3-carbonitrile; 1-(2,3-Difluoro-4-hydroxy-phenyl)-2-phenyl-1H-indole-3-carbonitrile; 1-(2,5-Difluoro-4-hydroxy-phenyl)-2-phenyl-1H-indole-3-carbonitrile; 1-(3,5-Difluoro-4-hydroxy-phenyl)-2-thiophen-3-yl-1H-indole-3-carbonitrile; 1-(3,5-Difluoro-4-hydroxy-phenyl)-2-thiophen-2-yl-1H-indole-3-carbonitrile; 1-(3,5-Di fluoro-4-hydroxy-phenyl)-2-(3,5-dimethyl-isoxazol-4-yl)-1H-indole-3-carbonitrile; 1-(3,5-Difluoro-4-hydroxy-phenyl)-2-(1-methyl-1H-pyrrol-2-yl)-1H-indole-3-carbonitrile; 1-(3,5-Difluoro-4-hydroxy-phenyl)-2-(3-methyl-thiophen-2-yl)-1H-indole-3-carbonitrile; 1-(3,5-Difluoro-4-hydroxy-phenyl)-2-(1-methyl-1H-pyrazol-4-yl)-1H-indole-3-carbonitrile; 1-(3,5-Difluoro-4-hydroxy-phenyl)-2-pyridin-4-yl-1H-indole-3-carbonitrile; 1-(3-Chloro-4-hydroxy-phenyl)-2-thiophen-3-yl-1H-indole-3-carbonitrile; 1-(3-Chloro-4-hydroxy-phenyl)-2-thiophen-2-yl-1H-indole-3-carbonitrile; 1-(3-Chloro-4-hydroxy-phenyl)-2-(3,5-dimethyl-isoxazol-4-yl)-1H-indole-3-carbonitrile; 1-(3-Chloro-4-hydroxy-phenyl)-2-(1-methyl-1H-pyrrol-2-yl)-1H-indole-3-carbonitrile; 1-(3-Chloro-4-hydroxy-phenyl)-2-(3-methyl-thiophen-2-yl)-1H-indole-3-carbonitrile; 1-(3-Chloro-4-hydroxy-phenyl)-2-pyridin-4-yl-1H-indole-3-carbonitrile; 1-(3-Fluoro-4-hydroxy-phenyl)-2-thiophen-3-yl-1H-indole-3-carbonitrile; 1-(3-Fluoro-4-hydroxy-phenyl)-2-thiophen-2-yl-1H-indole-3-carbonitrile; 2-(3,5-Dimethyl-isoxazol-4-yl)-1-(3-fluoro-4-hydroxy-phenyl)-1H-indole-3-carbonitrile; 1-(3-Fluoro-4-hydroxy-phenyl)-2-(1-methyl-1H-pyrrol-2-yl)-1H-indole-3-carbonitrile; 1-(3-Fluoro-4-hydroxy-phenyl)-2-(3-methyl-thiophen-2-yl)-1H-indole-3-carbonitrile; 1-(3-Fluoro-4-hydroxy-phenyl)-2-(1-methyl-1H-pyrazol-4-yl)-1H-indole-3-carbonitrile; 1-(3-Fluoro-4-hydroxy-phenyl)-2-pyridin-4-yl-1H-indole-3-carbonitrile; 2-Dimethylamino-1-(2-fluoro-4-hydroxy-phenyl)-1H-indole-3-carbonitrile; 2-(3,5-Dimethyl-isoxazol-4-yl)-1-(2-fluoro-4-hydroxy-phenyl)-1H-indole-3-carbonitrile; 1-(3-Fluoro-4-hydroxy-phenyl)-2-((E)-propenyl)-1H-indole-3-carbonitrile; 1-(3-Fluoro-4-hydroxy-phenyl)-2-((Z)-propenyl)-1H-indole-3-carbonitrile; 1-(2,3-Difluoro-4-hydroxy-phenyl)-2-((Z)-propenyl)-1H-indole-3-carbonitrile; 1-(2,3-Difluoro-4-hydroxy-phenyl)-2-vinyl-1H-indole-3-carbonitrile; 1-(2,3-Difluoro-4-hydroxy-phenyl)-2-thiophen-3-yl-1H-indole-3-carbonitrile; 1-(2,3-Difluoro-4-hydroxy-phenyl)-2-thiophen-2-yl-1H-indole-3-carbonitrile; 1-(2,3-Di fluoro-4-hydroxy-phenyl)-2-(3-methyl-thiophen-2-yl)-1H-indo-3-carbonitrile; 1-(2,3-Difluoro-4-hydroxy-phenyl)-2-(1-methyl-1H-pyrrol-2-yl)-1H-indole-3-carbonitrile; 2-(2-Acetyl-pyrrol-1-yl)-1-(3-fluoro-4-hydroxy-phenyl)-1H-indole-3-carbonitrile; 1-(3-Fluoro-4-hydroxy-phenyl)-2-pyrrol-1-yl-1H-indole-3-carbonitrile; 1-(2,3-Difluoro-4-hydroxy-phenyl)-2-pyrrol-1-yl-1H-indole-3-carbonitrile; 1-(2,3-Difluoro-4-hydroxy-phenyl)-2-prop-1-ynyl-1H-indole-3-carbonitrile; 1-(3-Fluoro-4-hydroxy-phenyl)-2-(2-methyl-prop-1-enyl)-1H-indole-3-carbonitrile; 1-(2,3-Difluoro-4-hydroxy-phenyl)-2-(2-methyl-prop-1-enyl)-1H-indole-3-carbonitrile; 2-(2-Acetyl-pyrrol-1-yl)-1-(2,3-di fluoro-4-hydroxy-phenyl)-1H-indole-3-carbonitrile; 1-(3-Fluoro-4-hydroxy-phenyl)-2-pyrazol-1-yl-1H-indole-3-carbonitrile; 1-(2,3-Di fluoro-4-hydroxy-phenyl)-2-pyrazol-1-yl-1H-indole-3-carbonitrile; 2-(2,5-Dimethyl-pyrrol-1-yl)-1-(3-fluoro-4-hydroxy-phenyl)-1H-indole-3-carbonitrile; 2-(2-Ethyl-pyrrol-1-yl)-1-(3-fluoro-4-hydroxy-phenyl)-1H-indole-3-carbonitrile; 2-(2-Cyano-pyrrol-1-yl)-1-(3-fluoro-4-hydroxy-phenyl)-1H-indole-3-carbonitrile; 1-(3-Fluoro-4-hydroxy-phenyl)-2-(2-methyl-pyrrol-1-yl)-1H-indole-3-carbonitrile; 1-(2,3-Difluoro-4-hydroxy-phenyl)-2-(2-ethyl-pyrrol-1-yl)-1H-indole-3-carbonitrile; 2-(2-Cyano-pyrrol-1-yl)-1-(2,3-difluoro-4-hydroxy-phenyl)-1H-indole-3-carbonitrile; 1-(2,3-Difluoro-4-hydroxy-phenyl)-2-(2-methyl-pyrrol-1-yl)-1H-indole-3-carbonitrile; 1-(2-Fluoro-4-hydroxy-phenyl)-2-pyrrol-1-yl-1H-indole-3-carbonitrile; 1-(2,3-difluoro-4-hydroxyphenyl)-2-(3-methylbut-2-enyl)-1H-indole-3-carbonitrile; [1-(4-Hydroxy-phenyl)-2-phenyl-1H-indol-3-yl]-acetonitrile; [1-(4-Hydroxy-phenyl)-2-phenyl-1H-indol-3-yl]-acetic acid; 2-[1-(4-Hydroxy-phenyl)-2-phenyl-1H-indol-3-yl]-acetamide; 4-(3-Isopropenyl-2-phenyl-indol-1-yl)-phenol; 4-[3-(2-Methyl-2H-pyrazol-3-yl)-2-phenyl-indol-1-yl]-phenol; 4-(2-Phenyl-3-thiazol-4-yl-indol-1-yl)-phenol; 4-(2-Phenyl-3-prop-1-ynyl-indol-1-yl)-phenol; 1-(4-Hydroxy-phenyl)-2-((E)-propenyl)-1H-indole-3-carboxylic acid, amide; 1-(4-Hydroxy-phenyl)-2-(2-methyl-prop-1-enyl)-1H-indole-3-carboxylic acid, amide; 1-(4-Hydroxy-phenyl)-2-((Z)-1-methyl-propenyl)-1H-indole-3-carboxylicacid, amide; 4-(2-Phenyl-3-pyrazol-1-yl-indol-1-yl)-phenol; 4-(3-Imidazol-1-yl-2-phenyl-indol-1-yl)-phenol; 4-[3-(5-Methyl-pyrazol-1-yl)-2-phenyl-indol-1-yl]-phenol; 2-Bromo-1-(4-hydroxy-phenyl)-1H-indole-3-carboxylic acid, amide; 1-(4-Hydroxy-phenyl)-2-((Z)-3,3,3-trifluoro-propenyl)-1H-indole-3-carbonitrile; (Z)-2-bromo-N'-hydroxy-1-(4-hydroxyphenyl)-1H-indole-3-carboximidamide; (Z)—N'-hydroxy-1-(4-hydroxyphenyl)-2-(1H-pyrrol-1-yl)-1H-indole-3-carboximidamide; 2-(3,5-Dimethyl-isoxazol-4-yl)-1-(4-hydroxy-phenyl)-1H-indole-3-carboxylic acid, amide; (Z)—N'-hydroxy-1-(4-hydroxyphenyl)-2-(2-methylprop-1-enyl)-1H-indole-3-carboximidamide; 1-(4-Hydroxy-phenyl)-2-phenyl-1H-indole-3-carboxylic acid; hydroxyamide; (Z)—N'-hydroxy-1-(4-hydroxyphenyl)-2-phenyl-1H-indole-3-carboximidamide; 1-(4-Hydroxy-phenyl)-2-pyrrol-1-yl-1H-indole-3-carboxylic acid, amide; [1-(4-Hydroxy-phenyl)-2-pyrrol-1-yl-1H-indol-3-yl]-carbamic acid tert-butyl ester; 2-(3,5-Dimethyl-isoxazol-4-yl)-1-(4-hydroxy-phenyl)-N-methyl-1H-indole-3-carboxamidine; Methyl 2-(3,5-dimethylisoxazol-4-yl)-1-(4-hydroxyphenyl)-1H-indole-3-carboximidate; N-((2-(3,5-dimethylisoxazol-4-yl)-1-(4-hydroxyphenyl)-1H-indol-3-yl)(imino)methyl)acetamide; 2-(5-ethyl-3-methylisoxazol-4-yl)-1-(4-hydroxyphenyl)-1H-indole-3-carboxamide; (Z)-2-(2-ethyl-1H-pyrrol-1-yl)-N-hydroxy-1-(4-hydroxyphenyl)-1H-indole-3-carboximidamide; (Z)—N'-hydroxy-1-(4-hydroxyphenyl)-2-(2-methyl-1H-pyrrol-1-yl)-1H-indole-3-carboximidamide; 1-(4-hydroxyphenyl)-2-(2-methyl-1H-pyrrol-1-yl)-1H-indole-3-carboxamide; 4-(3-chloro-2-(3,5-dimethylisoxazol-4-yl)-1H-indol-1-yl)phenol; (Z)-2-((Z)-but-2-en-2-yl)-N'-hydroxy-1-(4-hydroxyphenyl)-1H-indole-3-carboximidamide; (Z)—N'-hydroxy-1-(4-hydroxyphenyl)-2-(5-methyl-1H-pyrazol-1-yl)-1H-indole-3-carboximidamide; (Z)—N'-hydroxy-1-(4-hydroxyphenyl)-2-(4-methylthiophen-3-yl)-1H-indole-3-carboximidamide; (Z)-2-(2,5-dimethyl-1H-pyrrol-1-yl)-1H-hydroxy-1-(4-hydroxyphenyl)-1H-indole-3-carboximidamide; (Z)—N'-hydroxy-1-(4-hydroxyphenyl)-2-phenoxy-1H-indole-3-carboximidamide; 1-(4-Hydroxy-phenyl)-2-phenyl-1H-indole-3-carboxylic acid; 2-(3,5-Dimethyl-isoxazol-4-yl)-1-(3-fluoro-4-hydroxy-phenyl)-1H-indole-3-carboxylic acid; 2-(3,5-Dimethyl-isoxazol-4-yl)-1-(2-fluoro-4-hydroxy-phenyl)-1H-indole-3-carboxylic acid; 1-(2,3-Difluoro-4-hydroxy-phenyl)-2-(3,5-dimethyl-isoxazol-4-yl)-1H-indole-3- carboxylic acid; 1-(4-Hydroxy-phenyl)-2-((Z)-propenyl)-1H-indole-3-carboxylic acid; 1-(4-Hydroxy-phenyl)-2-((E)-propenyl)-H-indole-3-carboxylic acid; 1-(4-Hydroxy-phenyl)-2-(2-methyl-prop-1-enyl)-1H-indole-3-carboxylic acid; 1-(4-Hydroxy-phenyl)-2-(2-methyl-allyl)-1H-indole-3-carboxylic acid; 1-(4-Hydroxy-phenyl)-2-((Z)-1-methyl-propenyl)-1H-indole-3-carboxylicacid; 1-(3-Fluoro-4-hydroxy-phenyl)-2-thiophen-3-yl-1H-indole-3-carboxylic acid; 1-(3-Fluoro-4-hydroxy-phenyl)-2-thiophen-2-yl-1H-indole-3-carboxylic acid; 1-(3-Fluoro-4-hydroxy-phenyl)-2-(1-methyl-1H-pyrrol-2-yl)-1H-indole-3-carboxylic acid; 1-(3-Fluoro-4-hydroxy-phenyl)-2-(3-methyl-thiophen-2-yl)-1H-indole-3-carboxylic acid; 2-Bromo-1-(4-hydroxy-phenyl)-1H-indole-3-carboxylic acid; 1-(4-Hydroxy-phenyl)-2-pyrrol-1-yl-1H-indole-3-carboxylic acid; 2,7-Dibromo-1-(2,5-difluoro-4-hydroxy-phenyl)-1H-indole-3-carbonitrile; 2-Bromo-4-fluoro-1-(4-hydroxy-phenyl)-1H-indole-3-carbonitrile; 4-Fluoro-1-(4-hydroxy-phenyl)-2-pyrrol-1-yl-1H-indole-3-carbonitrile; 4-Fluoro-1-(4-hydroxy-phenyl)-2-phenyl-1H-indole-3-carbonitrile; 2-(3,5-Dimethyl-isoxazol-4-yl)-4-fluoro-1-(4-hydroxy-phenyl)-1H-indole-3-carbonitrile; 4-Fluoro-1-(4-hydroxy-phenyl)-2-(2-methyl-prop-1-enyl)-1H-indole-3-carbonitrile; 5-Fluoro-1-(4-hydroxy-phenyl)-2-phenyl-1H-indole-3-carbonitrile; 2-(3,5-Dimethyl-isoxazol-4-yl)-5-fluoro-1-(4-hydroxy-phenyl)-1H-indole-3-carbonitrile; 5-Fluoro-1-(4-hydroxy-phenyl)-2-pyrrol-1-yl-1H-indole-3-carbonitrile; 5-Fluoro-1-(4-hydroxy-phenyl)-2-(2-methyl-prop-1-enyl)-1H-indole-3-carbonitrile; (Z)-2-(3,5-dimethylisoxazol-4-yl)-5-fluoro-N'-hydroxy-1-(4-hydroxyphenyl)-1H-indole-3-carboximidamide; (Z)-2-(3,5-dimethylisoxazol-4-yl)-4-fluoro-N'-hydroxy-1-(4-hydroxyphenyl)-1H-indole-3-carboximidamide; (Z)-5-fluoro-N'-hydroxy-1-(4-hydroxyphenyl)-2-(2-methylprop-1-enyl)-1H-indole-3-carboximidamide; 4-Chloro-2-(3,5-dimethyl-isoxazol-4-yl)-1-(4-hydroxy-phenyl)-1H-indole-3-carbonitrile; 2-(3,5-dimethylisoxazol-4-yl)-4,5-difluoro-1-(4-hydroxyphenyl)-1H-indole-3-carbonitrile; 2-(4-cyano-1-methyl-1H-pyrazol-5-yl)-4-fluoro-1-(4-hydroxyphenyl)-1H-indole-3-carbonitrile; 2-(3,5-dimethylisoxazol-4-yl)-5-fluoro-1-(4-hydroxyphenyl)-1H-indole-3-carboximidamide; 2-(3,5-dimethylisoxazol-4-yl)-5-fluoro-1-(4-hydroxyphenyl)-1H-indole-3-carboxamide; 2-Bromo-7-fluoro-1-(4-hydroxy-phenyl)-1H-indole-3-carbonitrile; 2-(3,5-Dimethyl-isoxazol-4-yl)-7-fluoro-1-(4-hydroxy-phenyl)-1H-indole-3-carbonitrile; 2-(3,5-Dimethyl-isoxazol-4-yl)-4,7-difluoro-1-(4-hydroxy-phenyl)-1H-indole-3-carbonitrile; (Z)-2-(3,5-dimethylisoxazol-4-yl)-4,7-difluoro-N'-hydroxy-1-(4-hydroxyphenyl)-1H-indole-3-carboximidamide; 1-(2,5-Difluoro-4-hydroxy-phenyl)-2-(3,5-dimethyl-isoxazol-4-yl)-1H-indole-3-carbonitrile; 1-(3-bromo-4-hydroxyphenyl)-2-(2-methylprop-1-enyl)-1H-indole-3-carboxamide; (Z)-2-(3,5-dimethylisoxazol-4-yl)-1-(2-fluoro-4-hydroxyphenyl)-N'-hydroxy-1H-indole-3-carboximidamide; (Z)-1-(2,5-difluoro-4-hydroxyphenyl)-2-(3,5-dimethyl isoxazol-4-yl)-N'-hydroxy-1H-indole-3-carboximidamide; (Z)-1-(3,5-difluoro-4-hydroxyphenyl)-2-(3,5-dimethylisoxazol-4-yl)-N'-hydroxy-1H-indole-3-carboximidamide; (Z)-2-(3,5-dimethylisoxazol-4-yl)-1-(3-fluoro-4-hydroxyphenyl)-N'-hydroxy-1H-indole-3-carboximidamide; (Z)-1-(3-chloro-4-hydroxyphenyl)-2-(3,5-dimethylisoxazol-4-yl)-N'-hydroxy-1H-indole-3-carboximidamide; 2-(3,5-dimethylisoxazol-4-yl)-1-(2-fluoro-4-hydroxyphenyl)-1H-indole-3-carboxamide; (Z)-1-(2,3-difluoro-4-hydroxyphenyl)-2-(3,5-dimethylisoxazol-4-yl)-N'-hydroxy-1H-indole-3-carboximidamide; 1-(2,3-difluoro-4-hydroxyphenyl)-2-(3,5-dimethylisoxazol-4-yl)-1H-indole-3-carboxamide; 1-(2-fluoro-4-hydroxyphenyl)-2-(3-methylthiophen-2-yl)-1H-indole-3-carbonitrile; 2-(3,5-dimethyl-1H-pyrazol-4-yl)-1-(2-fluoro-4-hydroxyphenyl)-1H-indole-3-carbonitrile; 1-(2-fluoro-4-hydroxyphenyl)-2-(1-methyl-1H-pyrazol-5-yl)-1H-indole-3-carbonitrile; 1-(2-fluoro-4-hydroxyphenyl)-2-(1,3,5-trimethyl-1H-pyrazol-4-yl)-1H-indole-3-carbonitrile; 1-(2-fluoro-4-hydroxyphenyl)-2-(3-(trifluoromethyl)-1H-pyrazol-4-yl)-1H-indole-3-carbonitrile; (Z)-1-(2-fluoro-4-hydroxyphenyl)-N'-hydroxy-2-(3-methylthiophen-2-yl)-1H-indole-3-carboximidamide; (Z)-1-(2-fluoro-4-hydroxyphenyl)-N'-hydroxy-2-(1-methyl-1H-pyrazol-5-yl)-1H-indole-3-carboximidamide; (Z)-1-(2-fluoro-4-hydroxyphenyl)-N'-hydroxy-2-(1,3,5-trimethyl-1H-pyrazol-4-yl)-1H-indole-3-carboximidamide; (Z)-4-fluoro-1-(2-fluoro-4-hydroxyphenyl)-N'-hydroxy-2-(1-methyl-1H-pyrazol-5-yl)-1H-indole-3-carboximidamide; (Z)-4-fluoro-1-(2-fluoro-4-hydroxyphenyl)-N'-hydroxy-2-(1,3,5-trimethyl-1H-pyrazol-4-yl)-1H-indole-3-carboximidamide; (Z)-2-(3,5-dimethyl-1H-pyrazol-4-yl)-4-fluoro-1-(2-fluoro-4-hydroxyphenyl)-N'-hydroxy-1H-indole-3-carboximidamide; (Z)-4-fluoro-1-(2-fluoro-4-hydroxyphenyl)-N'-hydroxy-2-(3-methylthiophen-2-yl)-1H-indole-3-carboximidamide; (Z)-2-(3,5-dimethyl is oxazol-4-yl)-4-fluoro-1-(2-fluoro-4-hydroxyphenyl)-N'-hydroxy-1H-indole-3-carboximidamide; (Z)-1-(2-fluoro-4-hydroxyphenyl)-N'-hydroxy-2-(3-methylthiophen-2-yl)-1H-indole-3-carboximidamide; (Z)-1-(2-fluoro-4-hydroxyphenyl)-N'-hydroxy-2-(1-methyl-1H-pyrazol-5-yl)-1H-indole-3-carboximidamide; (Z)-1-(2-fluoro-4-hydroxyphenyl)-N'-hydroxy-2-(1,3,5-trimethyl-1H-pyrazol-4-yl)-1H-indole-3-carboximidamide; (Z)-2-(3,5-dimethyl-1H-pyrazol-4-yl)-1-(2-fluoro-4-hydroxyphenyl)-N'-hydroxy-1H-indole-3-carboximidamide; methyl 2-(3,5-dimethylisoxazol-4-yl)-1-(2-fluoro-4-hydroxyphenyl)-1H-indole-3-carbimidate; 2-(3,5-dimethylisoxazol-4-yl)-1-(3-fluoro-4-hydroxyphenyl)-1H-indole-3-carboxamide; 1-(2,5-di fluoro-4-hydroxyphenyl)-2-(3,5-dimethylisoxazol-4-yl)-1H-indole-3-carboximidamide; 2-(3,5-dimethylisoxazol-4-yl)-1-(3-fluoro-4-hydroxyphenyl)-1H-indole-3-carboximidamide; (Z)-1-(3-fluoro-4-hydroxyphenyl)-N'-hydroxy-2-(1H-pyrrol-1-yl)-1H-indole-3-carboximidamide; 1-(3-fluoro-4-hydroxyphenyl)-2-(1H-pyrrol-1-yl)-1H-indole-3-carboxamide; (Z)-1-(2,3-difluoro-4-hydroxyphenyl)-N'-hydroxy-2-(1H-pyrrol-1-yl)-1H-indole-3-carboximidamide; 1-(2,3-difluoro-4-hydroxyphenyl)-2-(1H-pyrrol-1-yl)-1H-indole-3-carboxamide; (Z)-2-(2,5-dimethyl-1H-pyrrol-1-yl)-1-(3-fluoro-4-hydroxyphenyl)-N'-hydroxy-1H-indole-3-carboximidamide; (Z)-1-(3-fluoro-4-hydroxyphenyl)-N'-hydroxy-2-(2-methyl-1H-pyrrol-1-yl)-1H-indole-3-carboximidamide; 1-(3,5-difluoro-4-hydroxyphenyl)-2-(3,5-dimethyl isoxazol-4-yl)-1H-indole-3-carboxamide; or (Z)-2-(3,5-dimethylisoxazol-4-yl)-6-fluoro-N'-hydroxy-1-(4-hydroxyphenyl)-1H-indole-3-carboximidamide.

In some embodiments, the ERβ ligand is a compound selected from the ERβ ligands disclosed in U.S. Pat. No. 8,334,280, hereby incorporated by reference.

In some embodiments, the ERβ ligand is 2-(3-fluoro-4-hydroxyphenyl)-7-vinyl-1,3-benzoxazol-5-ol (ERB-041; Wyeth). The ERβ ligand may be a substituted benzoxazole, such as any of the compounds disclosed in U.S. Pat. No. 6,794,403 or U.S. Patent Application Publication No. 2011/0212923 (each of which is hereby incorporated by reference).

The ERβ ligand may be 2-(5-hydroxy-1,3-benzoxazol-2-yl) benzene-1,4-diol; 3-(5-hydroxy-1,3-benzoxazol-2-yl)

benzene-1,2-diol; 2-(3-fluoro-4-hydroxyphenyl)-1,3-benzoxazol-5-ol; 2-(3-chloro-4-hydroxyphenyl)-1,3-benzoxazol-5-ol; 2-(2-chloro-4-hydroxyphenyl)-1,3-benzoxazol-5-ol; 2-(3-fluoro-4-hydroxyphenyl)-1,3-benzoxazol-6-ol; 2-(3-tert-butyl-4-hydroxyphenyl)-1,3-benzoxazol-6-ol; 2-(6-hydroxy-1,3-benzoxazol-2-yl)benzene-1,4-diol; 3-(6-hydroxy-1,3-benzoxazol-2-yl)benzene-1,2-diol; 4-(6-hydroxy-1,3-benzoxazol-2-yl)benzene-1,2-diol; 2-(3-chloro-4-hydroxyphenyl)-1,3-benzoxazol-6-ol; 4-(5-hydroxy-1,3-benzoxazol-2-yl)benzene-1,3-diol; 4-(6-hydroxy-1,3-benzoxazol-2-yl)benzene-1,3-diol; 6-chloro-2-(3-fluoro-4-hydroxyphenyl)-1,3-benzoxazol-5-ol; 6-bromo-2-(3-fluoro-4-hydroxyphenyl)-1,3-benzoxazol-5-ol; 6-chloro-2-(4-hydroxyphenyl)-1,3-benzoxazol-5-ol; 5-chloro-2-(4-hydroxyphenyl)-1,3-benzoxazol-6-ol; 7-bromo-2-(3-fluoro-4-hydroxyphenyl)-1,3-benzoxazol-5-ol; 7-bromo-2-(2-fluoro-4-hydroxyphenyl)-1,3-benzoxazol-5-ol; 7-bromo-2-(2,3-difluoro-4-hydroxyphenyl)-1,3-benzoxazol-5-ol; 2-(4-hydroxyphenyl)-7-vinyl-1,3-benzoxazol-5-ol; 7-(1,2-dibromoethyl)-2-(4-hydroxyphenyl)-1,3-benzoxazol-5-ol; 7-(1-bromovinyl)-2-(4-hydroxyphenyl)-1,3-benzoxazol-5-ol; 7-ethynyl-2-(4-hydroxyphenyl)-1,3-benzoxazol-5-ol; 2-(4-hydroxyphenyl)-7-propyl-1,3-benzoxazol-5-ol; 7-butyl-2-(4-hydroxyphenyl)-1,3-benzoxazol-5-ol; 7-cyclopentyl-2-(4-hydroxyphenyl)-1,3-benzoxazol-5-ol; ethyl 5-hydroxy-2-(4-hydroxyphenyl)-1,3-benzoxazole-7-carboxylate; 2-(4-hydroxyphenyl)-7-phenyl-1,3-benzoxazol-5-ol; 2-(4-hydroxyphenyl)-7-methoxy-1,3-benzoxazol-5-ol; 7-ethyl-2-(4-hydroxyphenyl)-1,3-benzoxazol-5-ol; 7-ethyl-2-(2-ethyl-4-hydroxyphenyl)-1,3-benzoxazol-5-ol; 5-hydroxy-2-(4-hydroxyphenyl)-1,3-benzoxazole-7-carbaldehyde; 7-(hydroxymethyl)-2-(4-hydroxyphenyl)-1,3-benzoxazol-5-ol; 7-(bromomethyl)-2-(4-hydroxyphenyl)-1,3-benzoxazol-5-ol; [5-hydroxy-2-(4-hydroxyphenyl)-1,3-benzoxazol-7-yl]acetonitrile; 7-(1-hydroxy-1-methylethyl)-2-(4-hydroxyphenyl)-1,3-benzoxazol-5-ol]; 2-(4-hydroxyphenyl)-7-isopropenyl-1,3-benzoxazol-5-ol; 2-(4-hydroxyphenyl)-7-isopropyl-1,3-benzoxazol-5-ol]; 7-bromo-2-(4-hydroxy-3-(trifluoromethyl)phenyl)-1,3-benzoxazol-5-ol; 7-(2-furyl)-2-(4-hydroxyphenyl)-1,3-benzoxazol-5-ol; 2-(3-fluoro-4-hydroxyphenyl)-7-(2-furyl)-1,3-benzoxazol-5-ol; 2-(4-hydroxyphenyl)-7-thien-2-yl-1,3-benzoxazol-5-ol; 2-(4-hydroxyphenyl)-7-(1,3-thiazol-2-yl)-1,3-benzoxazol-5-ol; 2-(3-fluoro-4-hydroxyphenyl)-5-hydroxy-1,3-benzoxazole-7-carbonitrile; 4-bromo-2-(4-hydroxyphenyl)-7-methoxy-1,3-benzoxazol-5-ol; 4,6-bibromo-2-(4-hydroxyphenyl)-7-methoxy-1,3-benzoxazol-5-ol; or 7-bromo-2-(3,5-difluoro-4-hydroxyphenyl)-1,3-benzoxazol-5-ol.

The ERβ ligand may be 2-(3-fluoro-4-hydroxyphenyl)-1,3-benzoxazol-5-ol, 2-(3-chloro-4-hydroxyphenyl)-1,3-benzoxazol-5-ol, 2-(3-fluoro-4-hydroxyphenyl)-7-vinyl-1,3-benzoxazol-5-ol, 2-(2-chloro-4-hydroxyphenyl)-1,3-benzoxazol-5-ol, 2-(3-fluoro-4-hydroxyphenyl)-1,3-benzoxazol-6-ol, 2-(3-tert-butyl-4-hydroxyphenyl)-1,3-benzoxazol-6-ol, 2-(3-chloro-4-hydroxyphenyl)-1,3-benzoxazol-6-ol, 6-chloro-2-(3-fluoro-4-hydroxyphenyl)-1,3-benzoxazol-5-ol, 6-bromo-2-(3-fluoro-4-hydroxyphenyl)-1,3-benzoxazol-5-ol, 6-chloro-2-(4-hydroxyphenyl)-1,3-benzoxazol-5-ol, 5-chloro-2-(4-hydroxyphenyl)-1,3-benzoxazol-6-ol, 7-bromo-2-(3-fluoro-4-hydroxyphenyl)-1,3-benzoxazol-5-ol, 7-bromo-2-(2-fluoro-4-hydroxyphenyl)-1,3-benzoxazol-5-ol, 7-bromo-2-(2,3-difluoro-4-hydroxyphenyl)-1,3-benzoxazol-5-ol, 7-vinyl-1,3-benzoxazol-5-ol, 7-(1,2-dibromoethyl)-2-(4-hydroxyphenyl)-1,3-benzoxazol-5-ol, 7-(1-bromovinyl)-2-(4-hydroxyphenyl)-1,3-benzoxazol-5-ol, 7-ethynyl-2-(4-hydroxyphenyl)-1,3-benzoxazol-5-ol, 2-(4-hydroxyphenyl)-7-propyl-1,3-benzoxazol-5-ol, 7-butyl-2-(4-hydroxyphenyl)-1,3-benzoxazol-5-ol, 7-cyclopentyl-2-(4-hydroxyphenyl)-1,3-benzoxazol-5-ol, ethyl 5-hydroxy-2-(4-hydroxyphenyl)-1,3-benzoxazole-7-carboxylate, 2-(4-hydroxyphenyl)-7-phenyl-1,3-benzoxazol-5-ol, 2-(4-hydroxyphenyl)-7-methoxy-1,3-benzoxazol-5-ol, 7-ethyl-2-(4-hydroxyphenyl)-1,3-benzoxazol-5-ol, 7-ethyl-2-(2-ethyl-4-hydroxyphenyl)-1,3-benzoxazol-5-ol, 5-hydroxy-2-(4-hydroxyphenyl)-1,3-benzoxazole-7-carbaldehyde, 7-(hydroxymethyl)-2-(4-hydroxyphenyl)-1,3-benzoxazol-5-ol, 7-(bromomethyl)-2-(4-hydroxyphenyl)-1,3-benzoxazol-5-ol, [5-hydroxy-2-(4-hydroxyphenyl)-1,3-benzoxazol-7-yl]acetonitrile, 7-(1-hydroxy-1-methylethyl)-2-(4-hydroxyphenyl)-1,3-benzoxazol-5-ol, 2-(4-hydroxyphenyl)-7-isopropenyl-1,3-benzoxazol-5-ol, 2-(4-hydroxyphenyl)-7-isopropyl-1,3-benzoxazol-5-ol, 7-bromo-2-(4-hydroxy-3-(trifluoromethyl)phenyl)-1,3-benzoxazol-5-ol, 7-(2-furyl)-2-(4-hydroxyphenyl)-1,3-benzoxazol-5-ol, 2-(3-fluoro-4-hydroxyphenyl)-7-(2-furyl)-1,3-benzoxazol-5-ol, 2-(4-hydroxyphenyl)-7-thien-2-yl-1,3-benzoxazol-5-ol, 2-(4-hydroxyphenyl)-7-(1,3-thiazol-2-yl)-1,3-benzoxazol-5-ol, 2-(3-fluoro-4-hydroxyphenyl)-5-hydroxy-1,3-benzoxazole-7-carbonitrile, 4-bromo-2-(4-hydroxyphenyl)-7-methoxy-1,3-benzoxazol-5-ol, 4,6-dibromo-2-(4-hydroxyphenyl)-7-methoxy-1,3-benzoxazol-5-ol, or 7-bromo-2-(3,5-difluoro-4-hydroxyphenyl)-1,3-benzoxazol-5-ol.

In some embodiments, the ERβ ligand is a compound selected from the ERβ ligands disclosed in U.S. Patent Application Publication No. 2007/0021495 or 2013/0274344, each of which is hereby incorporated by reference.

In some embodiments, the ERβ ligand is a halogen-substituted phenyl-2H-indazole, such as indazole chloride (see, e.g., Moore, S. M. et al. Proc. Nat'l Acad. Sci. USA 111(5):18061-66 (2014), hereby incorporated by reference).

In some embodiments, the ERβ ligand is not estriol. The ERβ ligand may be a non-steroidal compound. In some embodiments, the ERβ ligand is not a steroid hormone.

In certain aspects, the invention relates to methods for reducing the number or severity of at least one clinical sign or symptom of a neurodegenerative disease in a patient, comprising administering to the patient an estrogen receptor beta ligand, e.g., wherein the estrogen receptor beta ligand is a compound having the structure of formula I.

In certain embodiments, the invention relates to methods for preserving neurons in a patient afflicted with a neurodegenerative disease, comprising administering to the patient an estrogen receptor beta ligand, e.g., wherein the estrogen receptor beta ligand is a compound having the structure of formula I. Preserving neurons may comprise preserving spinal cord axons.

In certain embodiments, the invention relates to methods for preserving myelinating oligodendrocytes in a patient afflicted with a neurodegenerative disease, comprising administering to the patient an estrogen receptor beta ligand, e.g., wherein the estrogen receptor beta ligand is a compound having the structure of formula I.

In certain embodiments, the invention relates to methods for preserving axon myelination in a patient afflicted with a neurodegenerative disease, comprising administering to the patient an estrogen receptor beta ligand, e.g., wherein the estrogen receptor beta ligand is a compound having the structure of formula I.

In certain embodiments, the invention relates to methods for stimulating axon remyelination in a patient afflicted with a neurodegenerative disease, comprising administering to the patient an estrogen receptor beta ligand, e.g., wherein the estrogen receptor beta ligand is a compound having the structure of formula I.

In certain embodiments, the invention relates to methods reducing axonal loss in a patient afflicted with a neurodegenerative disease, comprising administering to the patient an estrogen receptor beta ligand, e.g., wherein the estrogen receptor beta ligand is a compound having the structure of formula I.

In certain embodiments, the invention relates to methods for reducing synaptic loss in a patient afflicted with a neurodegenerative disease, comprising administering to the patient an estrogen receptor beta ligand, e.g., wherein the estrogen receptor beta ligand is a compound having the structure of formula I.

In certain embodiments, the invention relates to methods for reducing neuronal cell loss in a patient afflicted with a neurodegenerative disease, comprising administering to the patient an estrogen receptor beta ligand, e.g., wherein the estrogen receptor beta ligand is a compound having the structure of formula I.

In certain embodiments, the invention relates to methods for reducing brain volume loss in a patient afflicted with a neurodegenerative disease, comprising administering to the patient an estrogen receptor beta ligand, e.g., wherein the estrogen receptor beta ligand is a compound having the structure of formula I.

In certain embodiments, the invention relates to methods for reducing cerebral cortex volume loss in a patient afflicted with a neurodegenerative disease, comprising administering to the patient an estrogen receptor beta ligand, e.g., wherein the estrogen receptor beta ligand is a compound having the structure of formula I.

In certain embodiments, the invention relates to methods for reducing cerebellum volume loss in a patient afflicted with a neurodegenerative disease, comprising administering to the patient an estrogen receptor beta ligand, e.g., wherein the estrogen receptor beta ligand is a compound having the structure of formula I.

In certain embodiments, the invention relates to methods for reducing local central nervous system inflammation in a patient afflicted with a neurodegenerative disease, comprising administering to the patient an estrogen receptor beta ligand, e.g., wherein the estrogen receptor beta ligand is a compound having the structure of formula I. The reduction in inflammation may be a result of a reduced number of macrophages.

In certain embodiments, the invention relates to methods for treating one or more symptoms of multiple sclerosis in a patient in need thereof, comprising administering to the patient an effective amount of an estrogen receptor beta ligand, e.g., wherein the estrogen receptor beta ligand is a compound having the structure of formula I. The one or more symptoms may include dystaxia, ataxia, or another motor disability.

The compound may be administered at a dose of about 1-100 mg/kg/day. The estrogen receptor beta ligand may be a compound having the structure of formula I, and it may be administered at a dose sufficient to achieve a mean blood concentration of the compound between 1 ng/ml and 1000 ng/ml. For example, the compound may be administered at a dose sufficient to achieve a mean blood concentration of the compound between 10 ng/ml and 50 ng/ml, between 25 ng/ml and 75 ng/ml, between 50 ng/ml and 100 ng/ml, between 75 ng/ml and 125 ng/ml, between 100 ng/ml and 150 ng/ml, between 125 ng/ml and 175 ng/ml, between 100 ng/ml and 200 ng/ml, between 150 ng/ml and 250 ng/ml, between 200 ng/ml and 300 ng/ml, between 250 ng/ml and 350 ng/ml, between 300 ng/ml and 400 ng/ml, between 350 ng/ml and 450 ng/ml, between 400 ng/ml and 500 ng/ml, between 450 ng/ml and 650 ng/ml, between 550 ng/ml and 750 ng/ml, between 650 ng/ml and 850 ng/ml, between 750 ng/ml and 950 ng/ml, or between 850 ng/ml and 1050 ng/ml. In some embodiments, the compound may be administered at a dose sufficient to achieve a mean blood concentration of the compound between 100 ng/ml and 200 ng/ml. In other embodiments, the compound may be administered at a dose sufficient to achieve a mean blood concentration of the compound between 10 ng/ml and 20 ng/ml. In some embodiments, the compound is administered at a dose sufficient to achieve a mean blood concentration of the compound between 10 ng/ml and 500 ng/ml. The compound may be administered at a dose sufficient to achieve a mean blood concentration of the compound between 100 ng/ml and 200 ng/ml.

In certain embodiments, the ligand is administered on a daily basis.

The neurodegenerative disease may be Alzheimer's disease, Parkinson's disease, multiple sclerosis, stroke, amyotrophic lateral sclerosis, cerebellar ataxia, frontotemporal dementia, prion disease, Huntington's disease, cerebral ischemia, cerebral dementia syndrome, infection-induced neurodegeneration disorders (e.g., AIDS-encephalopathy, Creutzfeld-Jakob disease, encephalopathies induced by rubiola and herpes viruses and borrelioses), metabolic-toxic neurodegenerative disorders (such as hepatic-, alcoholic-, hypoxic-, hypo-, or hyperglycemically-induced encephalopathies), encephalopathies induced by solvents or pharmaceuticals, trauma-induced brain damage, or spinal cord injury.

In some embodiments, the neurodegenerative disease is multiple sclerosis or clinically isolated syndrome. The neurodegenerative disease may be multiple sclerosis, and the patient may have one or more of relapsing-remitting multiple sclerosis, secondary-progressive multiple sclerosis, primary-progressive multiple sclerosis and progressive-relapsing multiple sclerosis.

The method may further comprise administering to the patient an immunotherapeutic agent. The immunotherapeutic agent may initiated at the same time or about the same time as initiation of treatment with the estrogen receptor beta ligand. Alternatively, the treatment with the estrogen receptor beta ligand may be initiated after the initiation of treatment with the immunotherapeutic agent.

The immunotherapeutic agent may be selected from interferon-beta 1a, interferon-beta 1b, pegylated interferon-beta-1a, glatiramer acetate, natalizumab, mitoxantrone, fingolimod, teriflunomide, dimethyl fumarate, mycophenolate mofetil, paclitaxel, cyclosporine, corticosteroids, azathioprine, cyclophosphamide, methotrexate, cladribine, 4-aminopyridine, and tizanidine. In some embodiments, the immunotherapeutic agent is selected from interferon-beta 1a, interferon-beta 1b, pegylated interferon-beta-1a, glatiramer acetate, natalizumab, mitoxantrone, fingolimod, teriflunomide, and dimethyl fumarate.

In some embodiments, the amount of the immunotherapeutic agent administered in combination with the estrogen receptor beta ligand is less than a therapeutically effective amount when the immunotherapeutic agent is administered alone (e.g., 20 mg glatiramer five times a week instead of 40 mg three times a week or 20 mg daily; 0.4 mg fingolimod daily instead of 0.5 mg daily; 200 mg dimethyl fumarate daily instead of 240 mg daily; or 0.25 mg interferon beta-1b every third day instead of 0.25 mg every other day). In some embodiments, the dose for glatiramer acetate (Copaxone®) is 20 mg s.c. six times a week, five times a week, four times a week, or three times a week. In some embodiments, the dose for fingolimod (Gilenya®) is 0.45 mg p.o. daily, 0.40 mg p.o. daily, 0.35 mg p.o. daily, 0.30 mg p.o. daily, or 0.25 mg p.o. daily. In some embodiments, the dose for dimethyl fumarate (Tecfidera®) is 220 mg p.o. daily, 200 mg p.o. daily, 180 mg p.o. daily, 160 mg p.o. daily, 150 mg p.o. daily, 140 mg p.o. daily, or 120 mg p.o. daily. In some embodiments, the dose for interferon beta-1a (Avonex®) is 27, 26, 25, 24, 23, 22, 21, 20, 19, 18, 17, 16, or 15 µg i.m. weekly, or 30 µg intramuscularly (i.m.) every 8, 9, 10 or 11 days. In some embodiments, the dose for interferon beta-1a (Rebif®) is 40, 39, 38, 37, 36, 35, 34, 33, 32, 31, 30, 29, 28, 27, 26, 25, 24, 23, or 22 µg s.c. three days a week, or 44 µg s.c. two days a week. In some embodiments, the dose for interferon beta-1b (Betaseron® or Extavia®) is 0.225, 0.200, 0.180, 0.175, 0.170, 0.160, 0.150, 0.140, 0.130, or 0.125 mg s.c. every other day, or 0.25 mg s.c. every third day.

In some embodiments, the patient is not being treated with another immunotherapeutic agent (besides the estrogen receptor beta ligand). The estrogen receptor beta ligand of formula 1 (or compounds of similar structure and function) may be used as a monotherapy in later secondary-progressive multiple sclerosis and primary-progressive multiple sclerosis, in which the inflammatory component of the disease is small. Additionally, the estrogen receptor beta ligand of formula 1 (or compounds of similar structure and function) may be used as a monotherapy (e.g., without conjoint administration of an anti-inflammatory therapy) for treating relapsing-remitting multiple sclerosis and early secondary-progressive multiple sclerosis because the estrogen receptor beta ligand of formula 1 has both neuroprotective and anti-inflammatory properties.

The patient may be a rodent or primate. In some embodiments, the patient is a human.

The patient may be male or female. In some embodiments, the patient is female; in other embodiments, male.

In certain aspects, the invention relates to methods of treating multiple sclerosis in a subject having a loss of brain gray matter of greater than about 0.3% in a period of at least about 6 months, comprising administering an estrogen receptor beta ligand to the subject daily, wherein: the estrogen receptor beta ligand is a compound having the structure of formula I; and the compound is administered at a dose sufficient to achieve a mean blood concentration of the compound between 10 ng/ml and 500 ng/ml. The loss of brain gray matter may be measured by MRI. In some embodiments, the treatment slows or eliminates a loss of brain gray matter. The loss of gray matter may be located in one or more of total brain, cerebral cortex, cerebellum, thalamus, caudate nucleus, and putamen.

In some embodiments, the invention relates to methods of treating a neurodegenerative disease, comprising administering to a subject in need thereof a first treatment regimen; assessing a change in total brain gray matter volume of the subject over a period of time; and changing the treatment regimen if the total brain gray matter volume decreases by at least about 0.3 percent between a first assessment and a second assessment about 6 months after the first assessment, by at least about 0.6 percent between a first assessment and a second assessment about one year after the first assessment, or by at least about 1.0 percent between a first assessment and a second assessment about two years after the first assessment. Changing the treatment regimen may comprise administering an effective amount of an estrogen receptor beta ligand to the subject in addition to the first treatment regimen.

In some embodiments, the invention relates to methods of treating a neurodegenerative disease, comprising administering to a subject in need thereof a first treatment regimen; assessing a change in gray matter volume of at least two brain regions of the subject over a period of time; and changing the treatment regimen if the gray matter volume of the at least two brain regions decreases by at least about 0.3 percent between a first assessment and a second assessment about 6 months after the first assessment, by at least about 0.6 percent between a first assessment and a second assessment about one year after the first assessment, or by at least about 1.0 percent between a first assessment and a second assessment about two years after the first assessment. Changing the treatment regimen may comprise administering an effective amount of an estrogen receptor beta ligand to the subject in addition to the first treatment regimen. The at least two brain regions may be selected from cerebral cortex, cerebellum, thalamus, caudate nucleus, putamen, and any combination thereof. In some embodiments, the at least one brain region is cerebral cortex.

Assessing may comprise performing brain magnetic resonance imaging (MRI). The first assessment may be performed before, at the same time as, or at about the same time as initiating the treatment regimen. The first assessment may be performed after the treatment regimen is initiated. The second assessment may be performed at least about six months, at least about one year, at least about 18 months, or at least about two years after said first assessment. In some embodiments, the second assessment is performed about one year after said first assessment.

The neurodegenerative disease may be Alzheimer's disease, Parkinson's disease, multiple sclerosis, stroke, amyotrophic lateral sclerosis, cerebellar ataxia, frontotemporal dementia, prion disease, Huntington's disease, cerebral ischemia, cerebral dementia syndrome, infection-induced neurodegeneration disorders (e.g., AIDS-encephalopathy, Creutzfeld-Jakob disease, encephalopathies induced by rubiola and herpes viruses and borrelioses), metabolic-toxic neurodegenerative disorders (such as hepatic-, alcoholic-, hypoxic-, hypo-, or hyperglycemically-induced encephalopathies), encephalopathies induced by solvents or pharmaceuticals, trauma-induced brain damage, or spinal cord injury.

In some embodiments, the neurodegenerative disease is multiple sclerosis or clinically isolated syndrome. The subject may have one or more of relapsing-remitting multiple sclerosis, secondary-progressive multiple sclerosis, primary-progressive multiple sclerosis and progressive-relapsing multiple sclerosis.

In some embodiments, the treatment regimen comprises administering to the subject an immunotherapeutic agent. The immunotherapeutic agent may be selected from interferon-beta 1a, interferon-beta 1b, pegylated interferon-beta-1a, glatiramer acetate, natalizumab, mitoxantrone, fingolimod, teriflunomide, dimethyl fumarate, mycophenolate mofetil, paclitaxel, cyclosporine, corticosteroids, azathioprine, cyclophosphamide, methotrexate, cladribine, 4-aminopyridine, and tizanidine. In some embodiments, the immunotherapeutic agent is selected from interferon-beta 1a, interferon-beta 1b, pegylated interferon-beta-1a, glatiramer acetate, natalizumab, mitoxantrone, fingolimod, teriflunomide, and dimethyl fumarate. In some embodiments, the amount of the immunotherapeutic agent administered in combination with the estrogen receptor beta ligand is less than a therapeutically effective amount when the immunotherapeutic agent is administered alone (e.g., 20 mg glatiramer five times a week instead of 40 mg three times a week or 20 mg daily; 0.4 mg fingolimod daily instead of 0.5 mg daily; 200 mg dimethyl fumarate daily instead of 240 mg daily; or 0.25 mg interferon beta-1b every third day instead of 0.25 mg every other day). In some embodiments, the dose for glatiramer acetate (Copaxone®) is 20 mg s.c. six times a week, five times a week, four times a week, or three times a week. In some embodiments, the dose for fingolimod (Gilenya®) is 0.45 mg p.o. daily, 0.40 mg p.o. daily, 0.35 mg p.o. daily, 0.30 mg p.o. daily, or 0.25 mg p.o. daily. In some embodiments, the dose for dimethyl fumarate (Tecfidera®) is 220 mg p.o. daily, 200 mg p.o. daily, 180 mg p.o. daily, 160 mg p.o. daily, 150 mg p.o. daily, 140 mg p.o. daily, or 120 mg p.o. daily. In some embodiments, the dose for interferon beta-1a (Avonex®) is 27, 26, 25, 24, 23, 22, 21, 20, 19, 18, 17, 16, or 15 µg i.m. weekly, or 30 µg intramuscularly (i.m.) every 8, 9, 10 or 11 days. In some embodiments, the dose for interferon beta-1a (Rebif®) is 40, 39, 38, 37, 36, 35, 34, 33, 32, 31, 30, 29, 28, 27, 26, 25, 24, 23, or 22 µg s.c. three days a week, or 44 µg s.c. two days a week. In some embodiments, the dose for interferon beta-1b (Betaseron® or Extavia®) is 0.225, 0.200, 0.180, 0.175, 0.170, 0.160, 0.150, 0.140, 0.130, or 0.125 mg s.c. every other day, or 0.25 mg s.c. every third day.

In certain embodiments, the subject is receiving an immunotherapeutic agent and has cognitive disability. For example, if a subject scores below 50 on PASAT, and optionally if such low score is verified upon retest within about one week to one month, then the subject may be deemed to have cognitive disability. In accordance with the invention, this cognitive disability is treated with an estrogen receptor beta ligand, and, in certain embodiments, followed up with further retest e.g., about six months from the start of an estrogen receptor beta ligand treatment, such as to achieve an increase in test score of at least 3 points.

In certain embodiments, the subject is receiving an immunotherapeutic agent and has progressive walking disability. For example, the subject performs a 25 foot walk test, e.g., at 0 months (baseline), 6 months, 1 year, and/or 2 years. If there is documented worsening in walking (takes more seconds), e.g., by 20 percent as compared to baseline, and this worsening is confirmed on a repeated walk test, e.g., about 3 months later, then the subject is deemed to have progressive worsening in walking. In accordance with the invention, this progressive walking disability is treated with an estrogen receptor beta ligand, and, in certain embodiments, followed up with repeat walking test, e.g., at about 1 year or 2 years from the start of an estrogen receptor beta ligand treatment, such as to stabilize or halt any further worsening in walking times.

In some embodiments, the first treatment regimen does not comprise an estrogen receptor beta ligand. The estrogen receptor beta ligand may be a compound having the structure of formula I. The compound of formula I is called AC-186. In some embodiments, the estrogen receptor beta ligand is a compound that is substantially similar in structure and function to AC-186, such as one of the compounds disclosed in PCT Patent Publication WO 2013/017619 A1 (incorporated herein by reference).

In some embodiments, the estrogen receptor beta ligand is a compound selected from the compounds disclosed in U.S. Patent Application Publications 2012/0202861 A1 or 2013/0131061 A1 (incorporated herein by reference). In some embodiments, the estrogen receptor beta ligand is KBRV1 or KBRV2 (Karo Bio, Huddinge, Sweden).

The wherein estrogen receptor beta ligand may be a compound having the structure of formula I, and it may be administered at a dose sufficient to achieve a mean blood concentration of the compound between 1 ng/ml and 1000 ng/ml. In some embodiments, the compound is administered at a dose sufficient to achieve a mean blood concentration of the compound between 10 ng/ml and 500 ng/ml. The compound may be administered at a dose sufficient to achieve a mean blood concentration of the compound between 100 ng/ml and 200 ng/ml.

In certain embodiments, the ligand is administered on a daily basis.

The subject may be a rodent or primate. In some embodiments, the subject is a human.

The subject may be male or female. In some embodiments, the subject is female.

This above description and following examples are not to be taken in a limiting sense, but are made merely for the purpose of illustrating the general principles of the invention. The section titles and overall organization of the present detailed description are for the purpose of convenience only and are not intended to limit the present invention.

Example 1

Materials and Methods.

Animals.

C57BL/6 and NOD mice 8 weeks old were purchased from Jackson Laboratories (Bar Harbor, Me.). Animals were maintained under environmentally controlled conditions in a 12-hour light/dark cycle with access to food and water ad libitum. All procedures were done in accordance with the guidelines of the National Institutes of Health and the Chancellor's Animal Research Committee of the University of California, Los Angeles Office for the Protection of Research Subjects.

Reagents.

AC-186 was dissolved in either Miglyol 812N liquid oil (Sasol North America) or sesame oil (Sigma Aldrich) as following concentration; 1.5 mg/mL for 3 mg/kg group, 5 mg/mL for 10 mg/kg group, and 15 mg/mL for 30 mg/kg group. Diarylpropionitrile (DPN, Tocris Biosciences) was dissolved in 10% molecular-grade ethanol and diluted with 90% of either Miglyol 812N liquid oil or sesame oil.

EAE and Treatments.

Animals were injected subcutaneously with Myelin Oligodendrocyte Glycoprotein (MOG), amino acids 35-55 (200 µg/animal, American Peptides), emulsified in complete Freund's adjuvant (CFA) and supplemented with *Mycobacterium Tuberculosis* H37ra (300 µg/animal, Difco Laboratories), over two sites drained by left inguinal and auxiliary lymph nodes in a total volume of 0.1 ml/mouse. One week later, a booster immunization was delivered over contra lateral lymph nodes. Pertussis toxin (500 ng/mouse) (List Biological Laboratories, Inc.) was injected intraperitoneally on days 0 and 2. Animals were monitored daily for EAE signs based on a standard EAE 0-5 scale scoring system: 0—healthy, 1—complete loss of tail tonicity, 2—loss of righting reflex, 3—partial paralysis, 4—complete paralysis of one or both hind limbs, and 5—moribund. Animals received 0.05 ml of either of 1.5, 5, 15 mg/mL AC-186, vehicle (sesame oil or Miglyol 812N liquid oil), or DPN (8 mg/kg/day) via subcutaneous injections every other day. Animals were treated with AC-186 or vehicle after EAE induction. Specifically, treatment was initiated at the first clear signs of clinical disease (EAE day 13-15), and continued to the endpoint of the experiment.

Rotarod Testing.

Motor behavior was tested up to two times per week for each mouse using a rotarod apparatus (Med Associates Inc., St. Albans, Vt.). Briefly, animals were placed on a rotating horizontal cylinder for a maximum of 200 seconds. The amount of time the mouse remained walking on the cylinder, without falling, was recorded. Each mouse was tested on a speed of 3-30 rpm and given three trials for any given day. The three trials were averaged to report a single value for an individual mouse, and then averages were calculated for all animals within a given treatment group. The first two trial days prior to immunization (day 0), served as practice trials.

Histological Preparation.

Mice were exposed to a lethal dose of isoflurane and perfused transcardially with ice-cold 1×PBS for 8-15 min, followed by 10% formalin for 10-15 min. Spinal cords and brains were dissected and submerged in 10% formalin overnight at 4° C., followed by 30% sucrose in PBS for 24 h. Tissues were embedded in 75% gelatin 15% sucrose solution for cryostat sectioning then post-fixed overnight in 10% formalin and cryoprotected in 30% sucrose. The embedded tissues were stored in −80° C. after flash frozen in dry ice. 40 µm thick free-floating spinal cord cross-sections, and sagittal brain sections were obtained with a microtome b cryostat (model HM505E) at −20° C. Tissues were collected serially and stored in 1×PBS with 1% sodium azide in 4° C. until immunohistochemistry.

Immunofluorescence.

Prior to histological staining, 40-mm thick free-floating sections were thoroughly washed with 1×PBS to remove residual sodium azide. In the case of anti-MBP labeling, tissue sections were processed with an additional 1 hour incubation with 5% glacial acetic acid in 100-proof ethanol at room temperature (RT). After washing tissue sections were permeabilized with 0.3% TritonX-100 and 2% normal goat serum in 1×PBS for 30 minutes at room temperature and blocked with 10% normal goat serum in 1×PBS for 1 hour. Tissues were then incubated with primary antibodies overnight in 4° C. The following primary antibody (Ab) were used: Rat anti-MBP (Millipore) at 1:1000 dilutions, Rabbit anti-NF200 (Sigma Aldrich) at 1:750 dilutions, Rabbit anti-beta-APP (Life Technologies) at 1:200 dilutions, Mouse anti-NeuN at 1:1000 dilutions (Millipore), Rabbit anti-PSD95, and Rabbit anti-Synapsin 1 at 1:500 dilutions (Millipore), and Rat anti-CD45 at 1:1500 dilutions (Millipore). The next day tissues were washed and incubated with secondary antibodies conjugated to Cy5 or Cy3 (Millipore) for 1 hour at room temperature. A nuclear stain DAPI (2 ng/mL; Molecular Probes) was added 10 minutes prior to final washes after secondary Ab incubation. Sections were mounted on slides, allowed to semi-dry, and cover slipped in fluoromount G (Fisher Scientific). IgG-control experiments were performed for all primary Ab, and only non-immunoreactive tissues under these conditions were analyzed.

Chromagen Immunohistochemistry.

Tissue sections were thoroughly washed with 1×PBS to remove residual sodium azide and treated with 3% hydrogen peroxide for 30 minutes at room temperature and then simultaneously blocked with 10% NGS and permeabilized with 0.3% Triton X-100 in 1×PBS for 1 hour at room temperature. Tissues were then incubated with primary antibodies overnight in 4° C. The following primary antibodies were used: Rat anti-CD3 at 1:2000 dilutions (BD Pharmigen), anti-Calbindin D28K at 1:1000 dilutions (Millipore), and Rabbit anti-Iba1 at 1:10000 dilutions (Wako Chemicals), were added for 2 hour at room temperature, and then placed in 4° C. overnight. Tissue sections then followed with secondary Ab labeling at 1:1000 dilutions (Vector labs) for 1 hour at room temperature and then with Avidin-Biotin Conjugation solution (Vector Labs) for 1 hour at room temperature. Tissue sections were treated with DAB peroxidase substrate (Vector labs) according to manufacturer instructions. IgG-control experiments were performed for all primary Ab, and only non-immunoreactive tissues under these conditions were analyzed.

Microscopy and Quantification.

Three spinal cord cross-sections at the C5-12 level from each mouse (n=3-6) were captured under microscope at 10× magnification. To quantify demyelination in the spinal cord and cerebellum, white matter was manually delineated on the basis of DAPI staining, and MBP staining intensity was calculated and reported in the sampled area. Axonal damage was assessed by counting beta-APP$^+$ cells in a confocal 10× microscope in spinal cord. Axonal densities were calculated by counting the number of NF200$^+$ or NeuN$^+$ neuronal cells in a 10× confocal image in the sampled area of the captured tissue section. Cerebellar Purkinje (Calbindin$^+$) cells were manually counted using a brightfield 10× microscope over the entire sagittal cerebellum. PSD-95 and Synapsin1 density was measured and reported as a percentage of the sampled area. CD45$^+$, CD3$^+$, and Iba1$^+$ cells in spinal cord cross-sections were manually quantified under either of a confocal 10× microscope for CD45$^+$ cells or a brightfield 10× microscope for CD3$^+$ and Iba1$^+$ cells. Histological Preparation. Mice were exposed to a lethal dose of isoflurane and perfused transcardially with ice-cold 1×PBS for 8-15 min, followed by 10% formalin for 10-15 min. Spinal cords and brains were dissected and submerged in 10% formalin overnight at 4° C., followed by 30% sucrose in PBS for 24 h. Tissues were embedded in 75% gelatin/15% sucrose solution for cryostat sectioning then post-fixed overnight in 10% formalin and cryoprotected in 30% sucrose. The embedded tissues were stored in −80° C. after flash frozen in dry ice. 40 µm thick free-floating spinal cord cross-sections, and sagittal brain sections were obtained with a microtome b cryostat (model HM505E) at −20° C. Tissues were collected serially and stored in 1×PBS with 1% sodium azide in 4° C. until immunohistochemistry.

Immunofluorescence.

Prior to histological staining, 40-mm thick free-floating sections were thoroughly washed with 1×PBS to remove residual sodium azide. In the case of anti-MBP labeling, tissue sections were processed with an additional 1 hour incubation with 5% glacial acetic acid in 100-proof ethanol at room temperature (RT). After washing tissue sections were permeabilized with 0.3% Triton X-100 and 2% normal goat serum in 1×PBS for 30 minutes at room temperature and blocked with 10% normal goat serum in 1×PBS for 1 hour. Tissues were then incubated with primary antibodies overnight in 4° C. The following primary antibody (Ab) were used: Rat anti-MBP (Millipore) at 1:1000 dilutions, Rabbit anti-NF200 (Sigma Aldrich) at 1:750 dilutions, Rabbit anti-beta-APP (Life Technologies) at 1:200 dilutions, Mouse anti-NeuN at 1:1000 dilutions (Millipore), Rabbit anti-PSD95, and Rabbit anti-Synapsin1 at 1:500 dilutions (Millipore), and Rat anti-CD45 at 1:1500 dilutions (Millipore). The next day tissues were washed and incubated with secondary antibodies conjugated to Cy5 or Cy3 (Millipore) for 1 hour at room temperature. A nuclear stain DAPI (2 ng/mL; Molecular Probes) was added 10 minutes prior to final washes after secondary Ab incubation. Sections were mounted on slides, allowed to semi-dry, and cover slipped in fluoromount G (Fisher Scientific). IgG-control experiments were performed for all primary Ab, and only non-immunoreactive tissues under these conditions were analyzed.

Chromagen Immunohistochemistry.

Tissue sections were thoroughly washed with 1×PBS to remove residual sodium azide and treated with 3% hydrogen peroxide for 30 minutes at room temperature and then simultaneously blocked with 10% NGS and permeabilized with 0.3% Triton X-100 in 1×PBS for 1 hour at room temperature. Tissues were then incubated with primary antibodies overnight in 4° C. The following primary antibodies were used: Rat anti-CD3 at 1:2000 dilutions (BD Pharmigen), anti-Calbindin D28K at 1:1000 dilutions (Millipore), and Rabbit anti-Iba1 at 1:10000 dilutions (Wako Chemicals), were added for 2 hour at room temperature, and then placed in 4° C. overnight. Tissue sections then followed with secondary Ab labeling at 1:1000 dilutions (Vector labs) for 1 hour at room temperature and then with Avidin-Biotin Conjugation solution (Vector Labs) for 1 hour at room temperature. Tissue sections were treated with DAB peroxidase substrate (Vector labs) according to manufacturer instructions. IgG-control experiments were performed for all primary Ab, and only non-immunoreactive tissues under these conditions were analyzed.

Microscopy and Quantification.

Three spinal cord cross-sections at the C5-12 level from each mouse (n=3-6) were captured under microscope at 10× magnification. To quantify demyelination in the spinal cord and cerebellum, white matter was manually delineated on the basis of DAPI staining, and MBP staining intensity was calculated and reported in the sampled area. Axonal damage was assessed by counting beta-APP$^+$ cells in a confocal 10× microscope in spinal cord. Axonal densities were calculated by counting the number of NF200$^+$ or NeuN$^+$ neuronal cells in a 10× confocal image in the sampled area of the captured tissue section. Cerebellar Purkinje (Calbindin$^+$) cells were manually counted using a brightfield 10× microscope over the entire sagittal cerebellum. PSD-95 and Synapsin1 density was measured and reported as a percentage of the sampled area. CD45$^+$, CD3$^+$, and Iba1$^+$ cells in spinal cord cross-sections were manually quantified under either of a confocal 10× microscope for CD45$^+$ cells or a brightfield 10× microscope for CD3$^+$ and Iba1$^+$ cells.

Example 2

Figure 2:
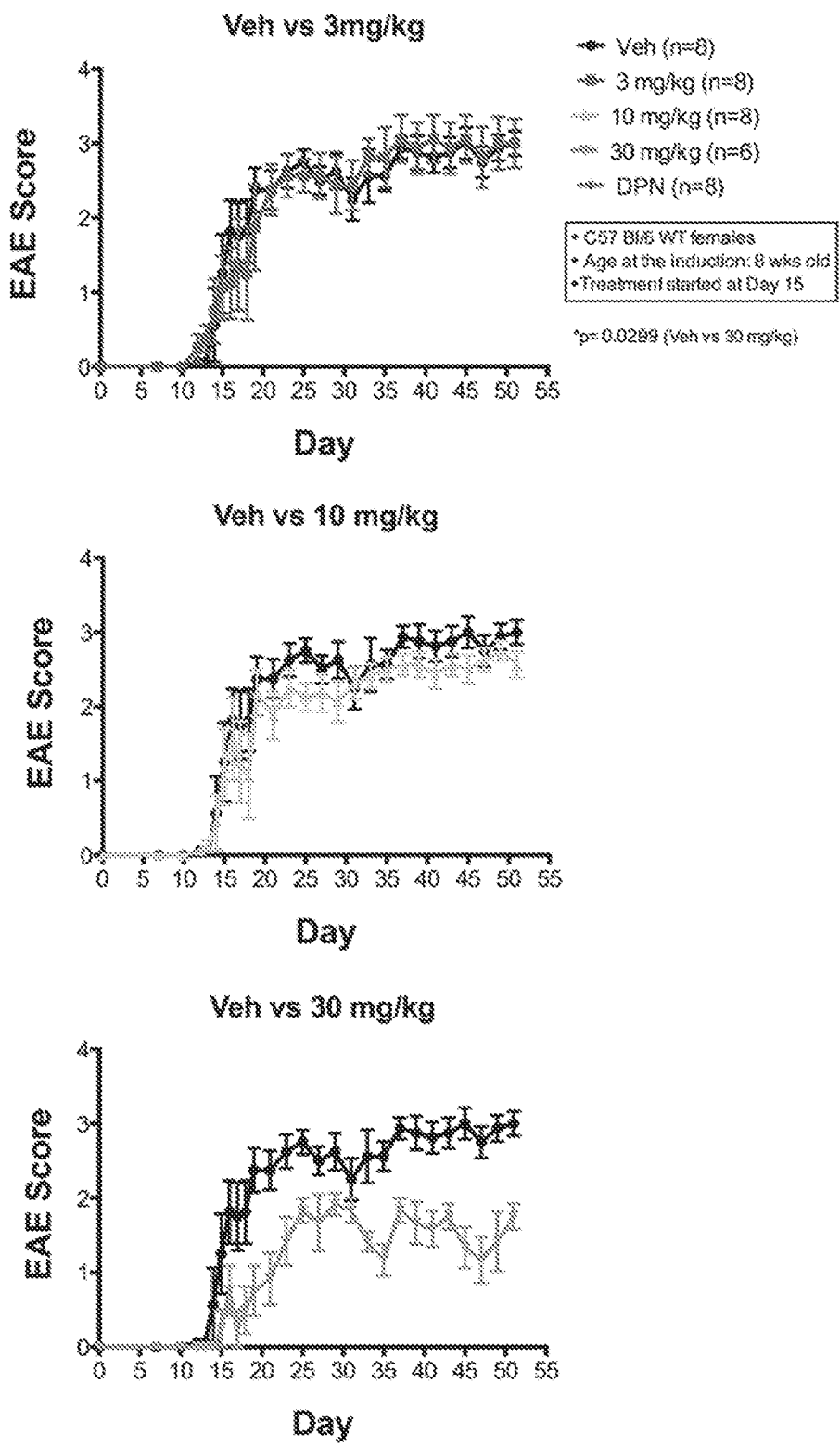
FIG. 2. EAE scores separated by different doses of AC-186 dose. Each graph shows the scores for control animals (Veh; "●"). Animals that received high dose AC-186 treatments (30 mg/kg; lower panel, "▼") had significantly less severe EAE scores as compared to the sesame oil vehicle alone (p=0.0299).

Three doses of the AC-186 compound were tested in C57BL/6 female mice: low (3 mg/kg, every other day), medium (10 mg/kg, every other day), and high (30 mg/kg, every other day), each injected subcutaneously in a sesame oil vehicle. The ERβ ligand diarylpropionitrile (DPN) was tested as a positive control because DPN can partially ameliorate EAE and because the treatment effects in EAE experiments can vary based on the level of disease severity within an experiment. Direct comparisons between treatments were only made between treatment groups within a single EAE experiment and not between treatment groups of different EAE experiments. DPN, however, was difficult to dissolve in sesame oil, and thus, DPN was first dissolved in ethanol and added to sesame oil at a concentration of 10% ethanol in sesame oil. The AC-186 compound dissolved in sesame oil after five minutes on a nutating shaker. Thus, FIG. 1 shows graphs in which the vehicle consisted of sesame oil for AC-186 (all doses) and vehicle, while the DPN vehicle was 10% ethanol in sesame oil. The low (3 mg/kg) dose of AC-186 had no effect on the EAE score, the medium dose (10 mg/kg) displayed a trend toward improvement, and the high (30 mg/kg) dose displayed a significant effect in ameliorating standard EAE clinical scores (p=0.0299) (FIGS. 1 and 2). The difference in improvement between the 30 mg/kg AC-186 group and all other groups increased with time.

Figure 3:
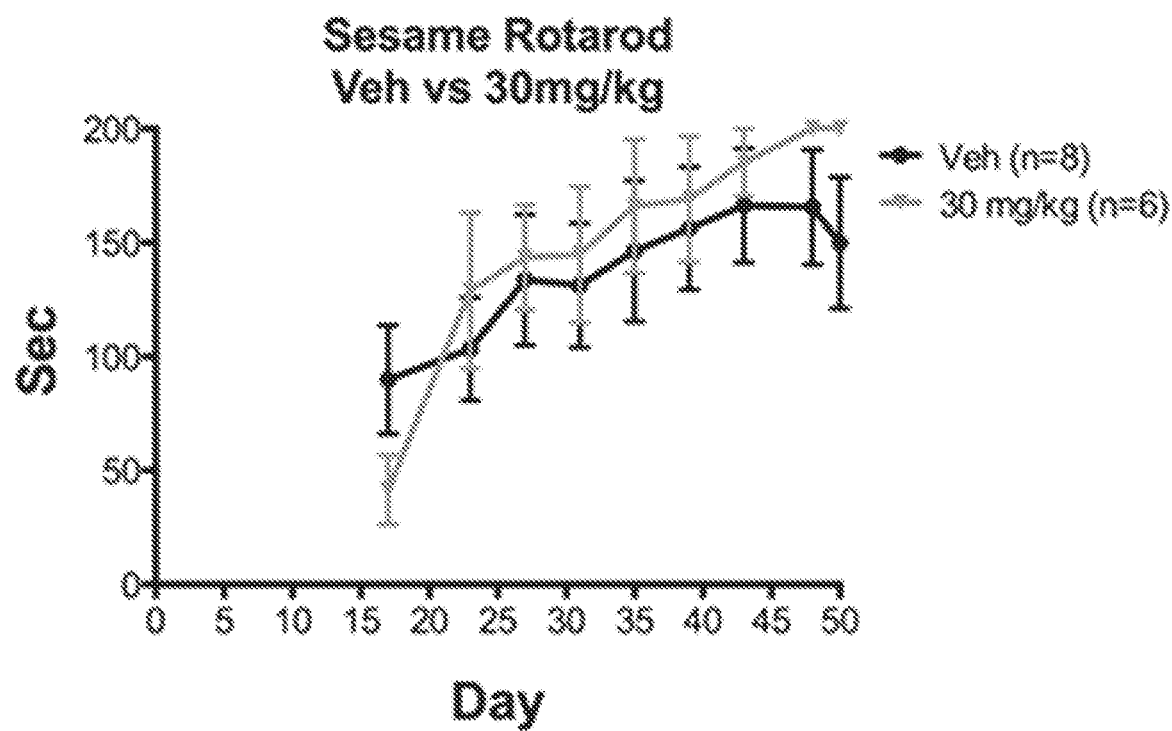
FIG. 3. Rotarod to assess motor coordination and balance. Rotarod times for female C57BL/6 mice that received high dose AC-186 treatments (30 mg/kg; "▼") in sesame oil versus control animals (Veh; "●").
Figure 4:
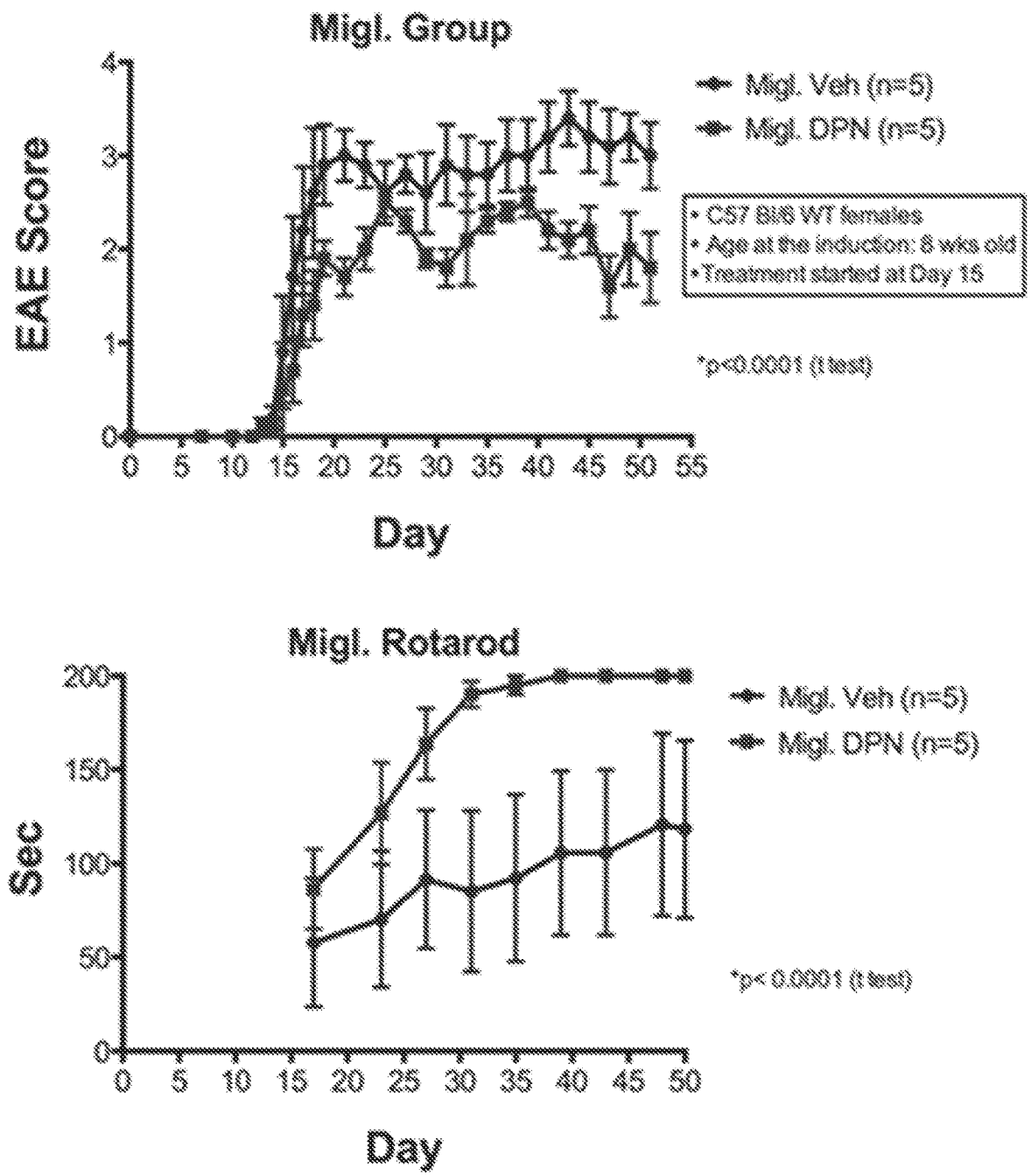
FIG. 4. Comparisons of outcomes with miglyol as the carrier, using DPN as the ER beta ligand. EAE scores and rotarod times for a positive control DPN in the vehicle of 10% ethanol/miglyol solution (Migl. DPN; "■") and for control animals (Migl. Veh; "●"). DPN treated animals displayed better EAE scores and better performance with the rotarod test.

To assess whether a more novel EAE outcome might be affected as well by the high (30 mg/kg) dose, rotarod was also performed, as shown in FIG. 3. Rotarod performance is likely more aligned with coordination and cerebellar function than standard EAE scores, which reflect principally walking and spinal cord pathology. No significant effect was observed for mice receiving 30 mg/kg AC-186 in sesame oil relative to those receiving vehicle only; however, very late in disease, at the time when ER beta ligands are known to start working, the performance curves trended toward divergence, with AC-186 treated mice trending toward improved performance. Further, the rotarod test is insensitive in detecting differences when the vehicle group performs well, and the vehicle group performed well in this case, staying on the rotarod for approximately 150 seconds. Additionally, during the final two time-points, on days 48 and 50, the AC-186 group performed perfectly during the 200 second test, and thus, a significant effect may have been masked by the experimental design.

Example 3

Figure 5:
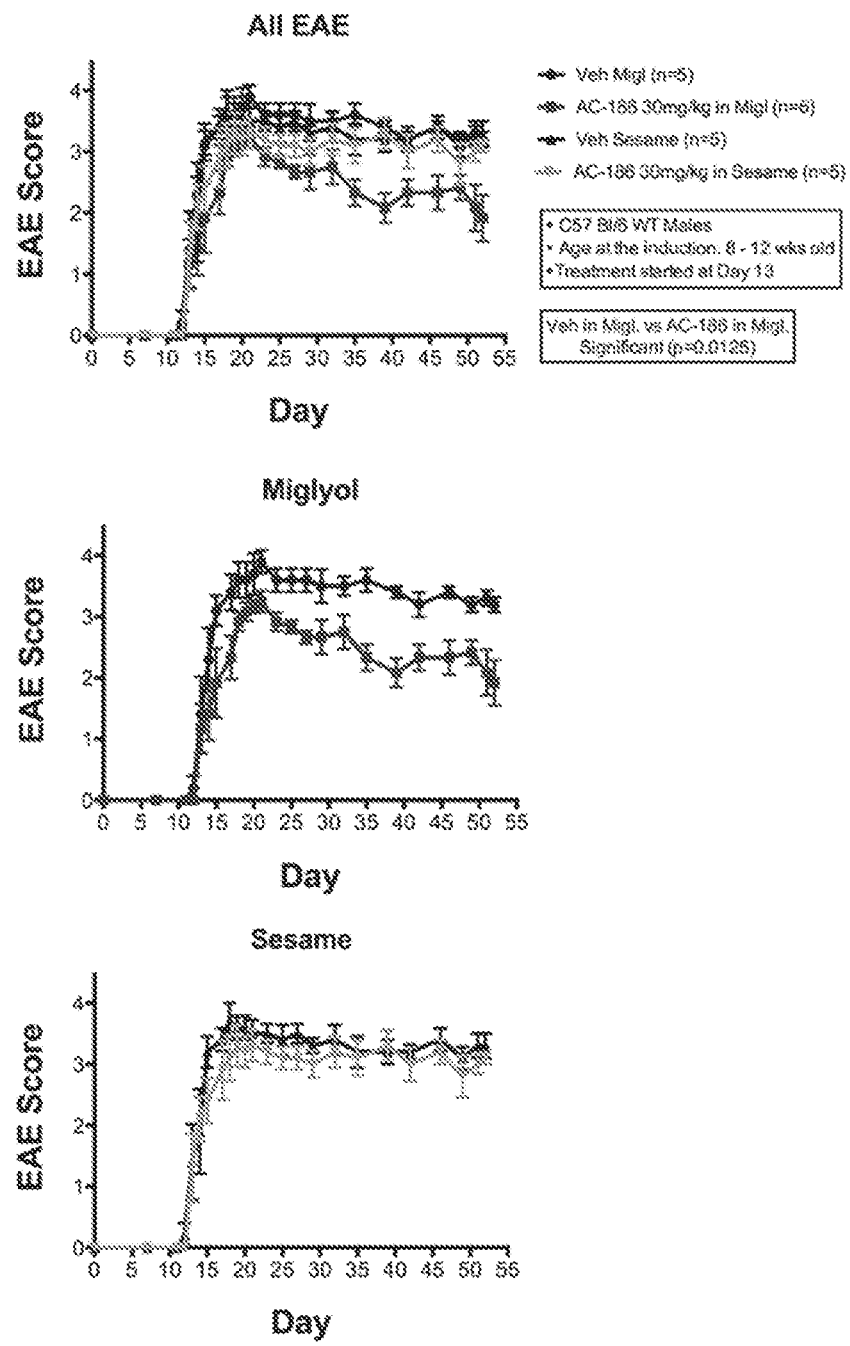
FIG. 5. Comparisons of outcomes using sesame oil versus miglyol as the carrier, using AC-186 as the ER beta ligand (EAE scores). EAE scores for male C57BL/6 mice that received high dose AC-186 treatments (30 mg/kg) in either sesame oil (top and bottom graphs) or miglyol (top and middle graphs) or the vehicle alone. Animals receiving AC-186 in miglyol displayed better EAE scores than those receiving the vehicle alone (see. e.g., middle panel).
Figure 6:
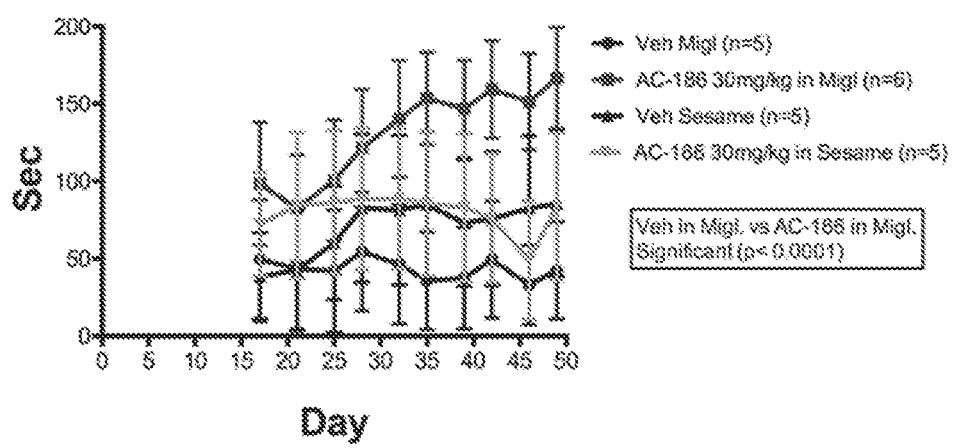
FIG. 6. Comparisons of outcomes using sesame oil versus miglyol as the carrier, using AC-186 as the ER beta ligand (Rotarod times). Rotarod times for male C57BL/6 mice that received high dose AC-186 treatments (30 mg/kg) in either sesame oil (top and bottom graphs) or miglyol (top and middle graphs) or the vehicle alone. Animals receiving AC-186 in miglyol displayed better rotarod scores than those receiving the vehicle alone (see, e.g., middle panel).
Figure 6:
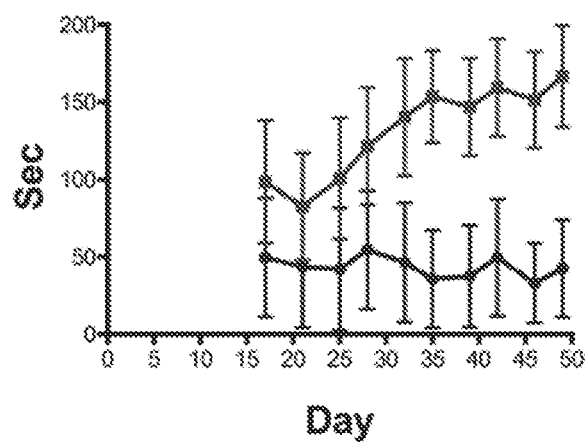
Figure 6:
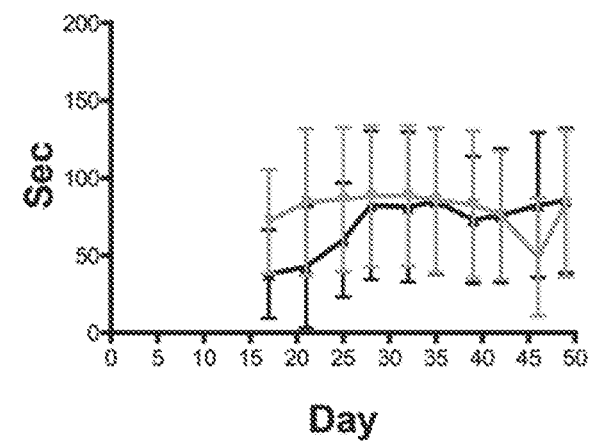

DPN protects against EAE better when administered in a Miglyol vehicle rather than in a sesame oil vehicle, and thus, the effect of the choice of vehicle on the efficacy of AC-186 was assessed. Accordingly, the AC-186 compound was assessed in C57BL/6 males using sesame oil and miglyol as vehicles. Male mice receiving AC-186 administered at 30 mg/kg in miglyol performed significantly better than mice receiving miglyol alone as assessed by both EAE score (FIG. 5) and rotarod performance (FIG. 6). In contrast, male mice receiving AC-186 administered at 30 mg/kg in sesame oil did not perform significantly better than mice receiving sesame oil alone as assessed by EAE score (FIG. 5) and rotarod performance (FIG. 6). Notably, the AC-186 solution dissolved more rapidly in miglyol than sesame oil, and miglyol could dissolve AC-186 by merely pipetting for 30 seconds. In contrast, AC-186 required mixing/nutating for 5 minutes to dissolve the compound in sesame oil.

The 30 mg/kg dose of AC-186 dissolved in sesame oil did not display efficacy in male C57BL/6 mice, in contrast with the results obtained for female C57BL/6 mice as described in Example 2.

Example 4

Figure 7:
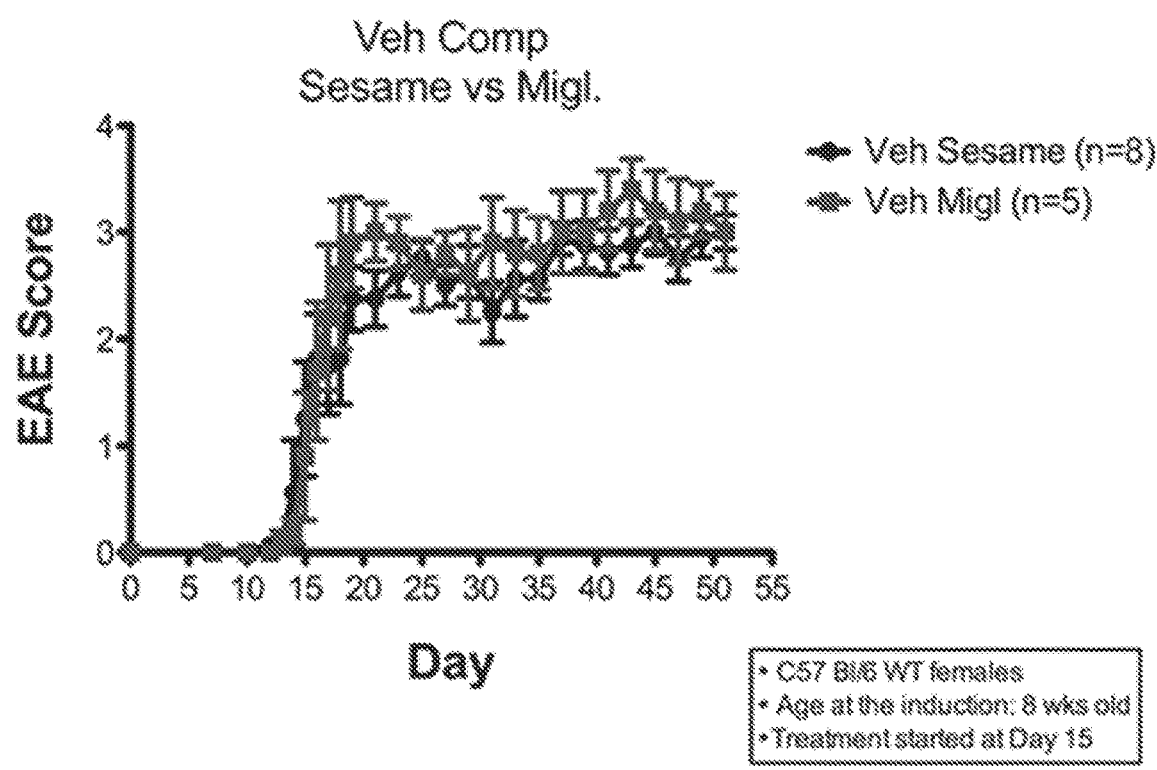
FIG. 7. Treatment with carrier alone and no ER beta ligand. EAE scores for animals that received either the sesame oil or miglyol vehicle and no ERβ ligand. There was no effect on disease, with either carrier, when no ER beta ligand was administered, showing that the ER beta ligand's delivery in each carrier underlies differences in effectiveness with each carrier.

Sesame oil has been shown previously to have some nonspecific immunostimulatory effects, and thus is not most commonly used as a vehicle in EAE. As shown in FIG. 7, the different vehicle type does not affect EAE differentially when given without an ERβ ligand. Rather, the different vehicle type likely affects the ability of a given ERβ ligand to protect in EAE, with Miglyol enabling better EAE protection than sesame oil when either DPN or AC-186 are administered.

Example 5

Figure 8:
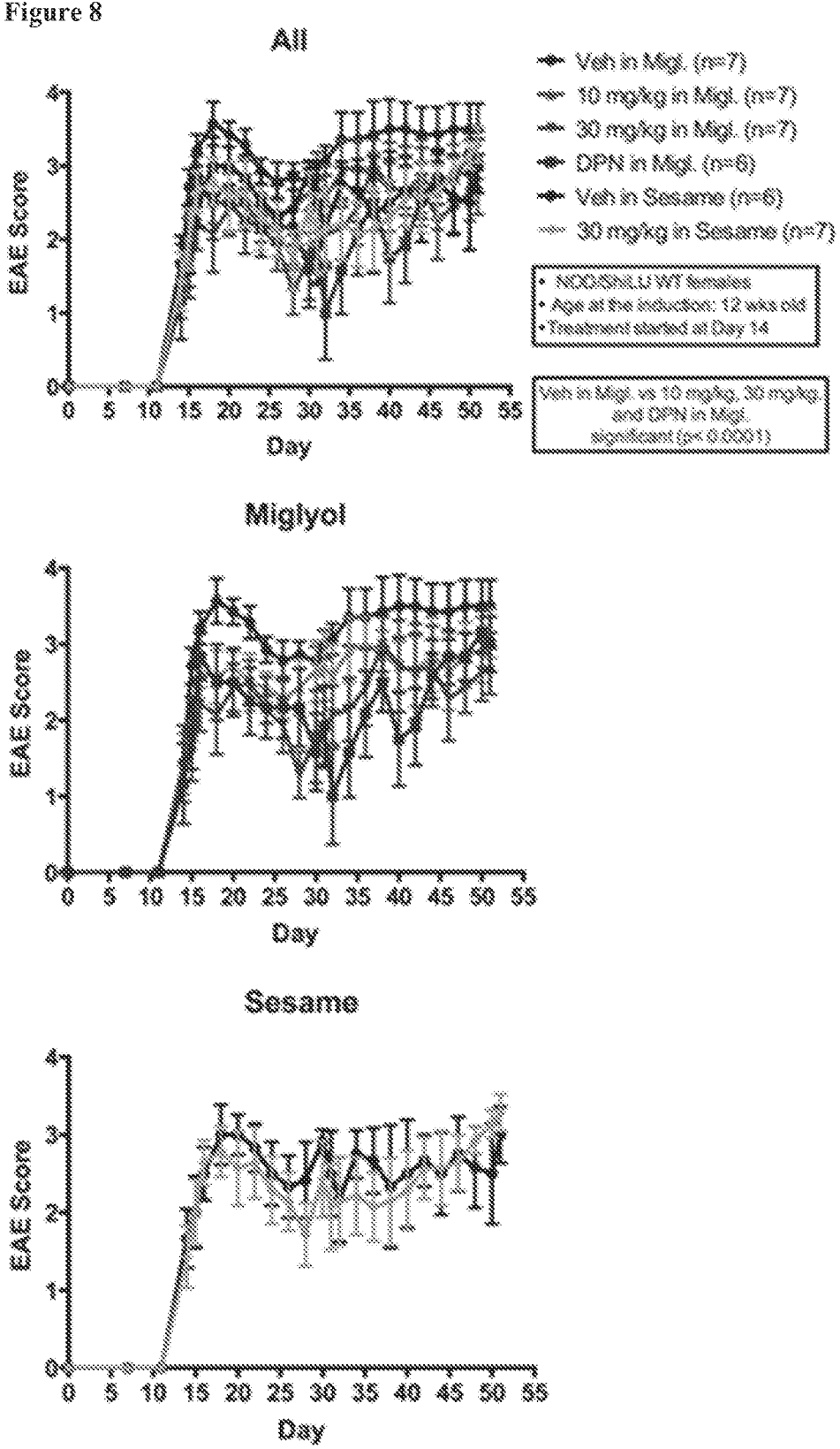
FIG. 8.
Figure 8:
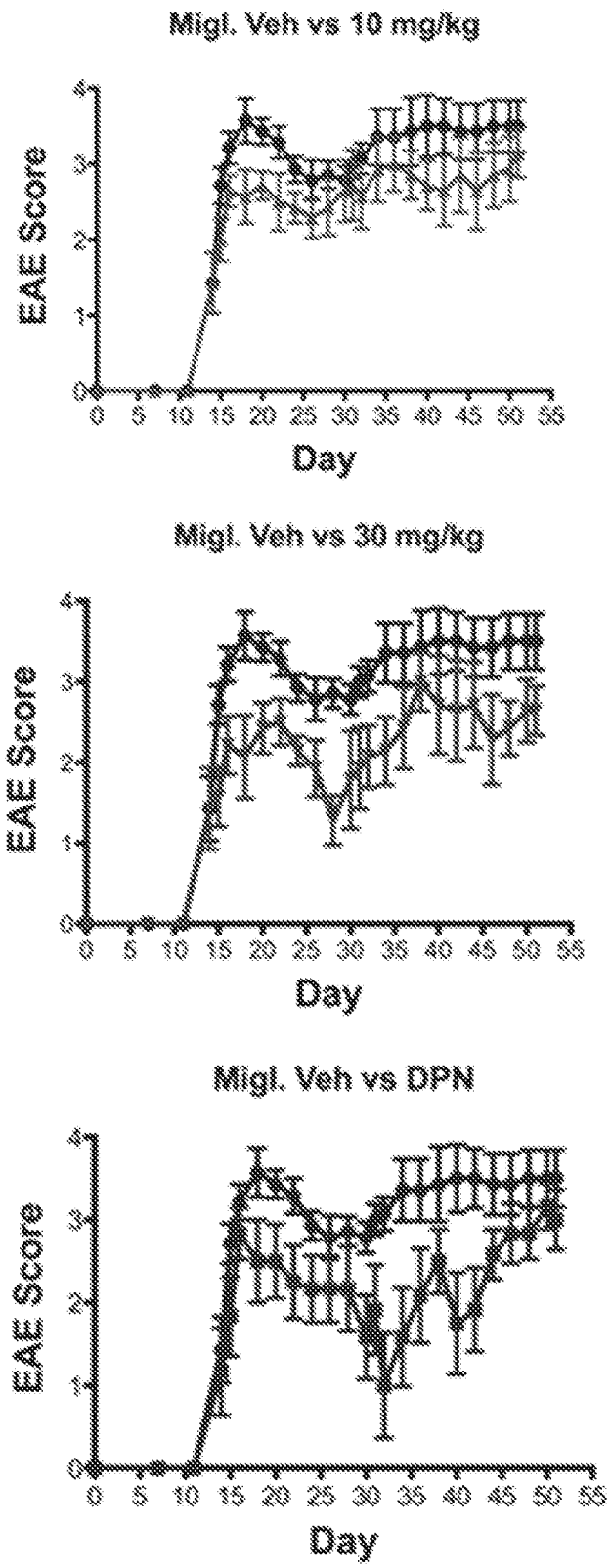

The effect of AC-186 was assessed in female NOD mice using a MOG-induced EAE model. The efficacy of AC-186 was tested in miglyol and sesame oil vehicles. In these models, AC-186 improved EAE scores relative to vehicle only for mice receiving 10 mg/kg or 30 mg/kg in miglyol (p<0.001), and the 30 mg/kg group trended toward increased efficacy relative to the 10 mg/kg group (FIG. 8). In comparison, the positive control DPN, which had not previously been tested in the NOD EAE model, also significantly ameliorated EAE, appearing similar to the disease reduction observed with the 30 mg/kg dose of AC-186. In contrast, AC-186 in sesame oil did not ameliorate EAE scores, consistent with data above in the C57BL/6 male EAE experiment where AC-186 in miglyol ameliorated EAE while AC-186 in sesame oil did not.

Figure 9:
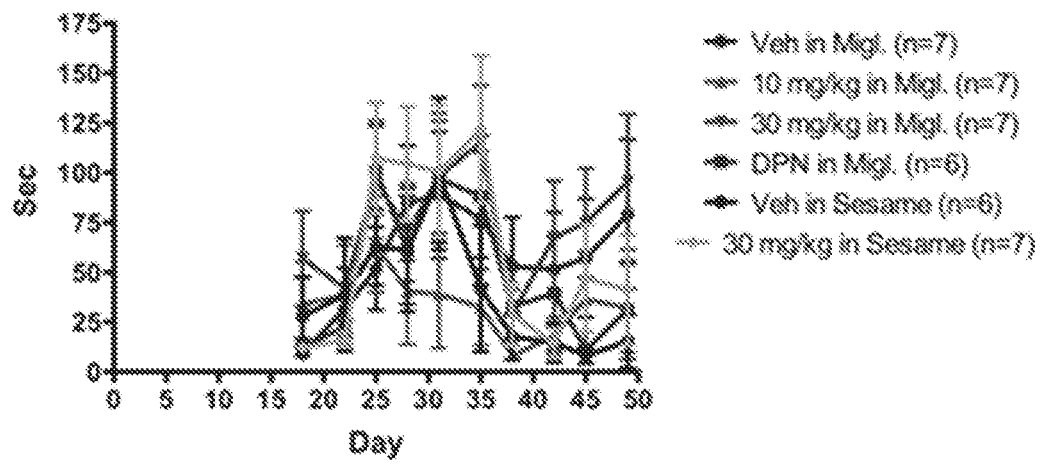
FIG. 9. EAE Rotarod times for NOD females under various treatment conditions. Rotarod performance was relatively poor in all female NOD groups with no significant difference between treatment groups.
Figure 9:
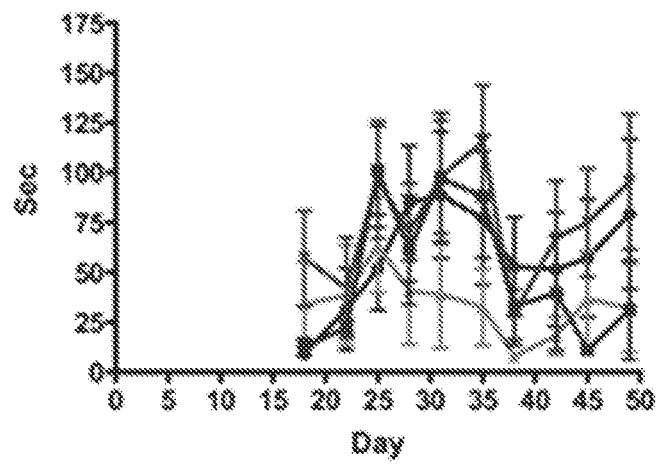
Figure 9:
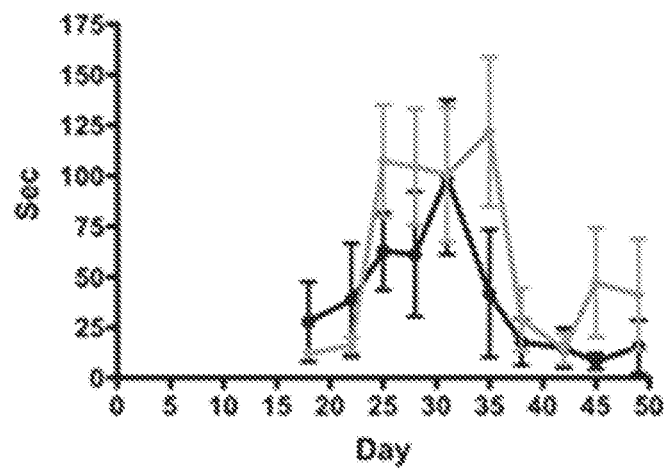

Rotarod testing had never before been done in the NOD EAE model, and rotarod scores were surprisingly poor with most mice staying on the rotarod for only 0-100 seconds and none staying on for 125-200 seconds. These results were surprising in part because the EAE walking scores were reasonably, although not dramatically, severe in the moderate range of 2-3. These results may suggest that EAE in the NOD model preferentially affects cerebellar or other balance related pathways as compared to EAE in the C57BL/6 model. The intervention produced no significant improvement in rotarod scores (FIG. 9).

Example 6

Figure 10:
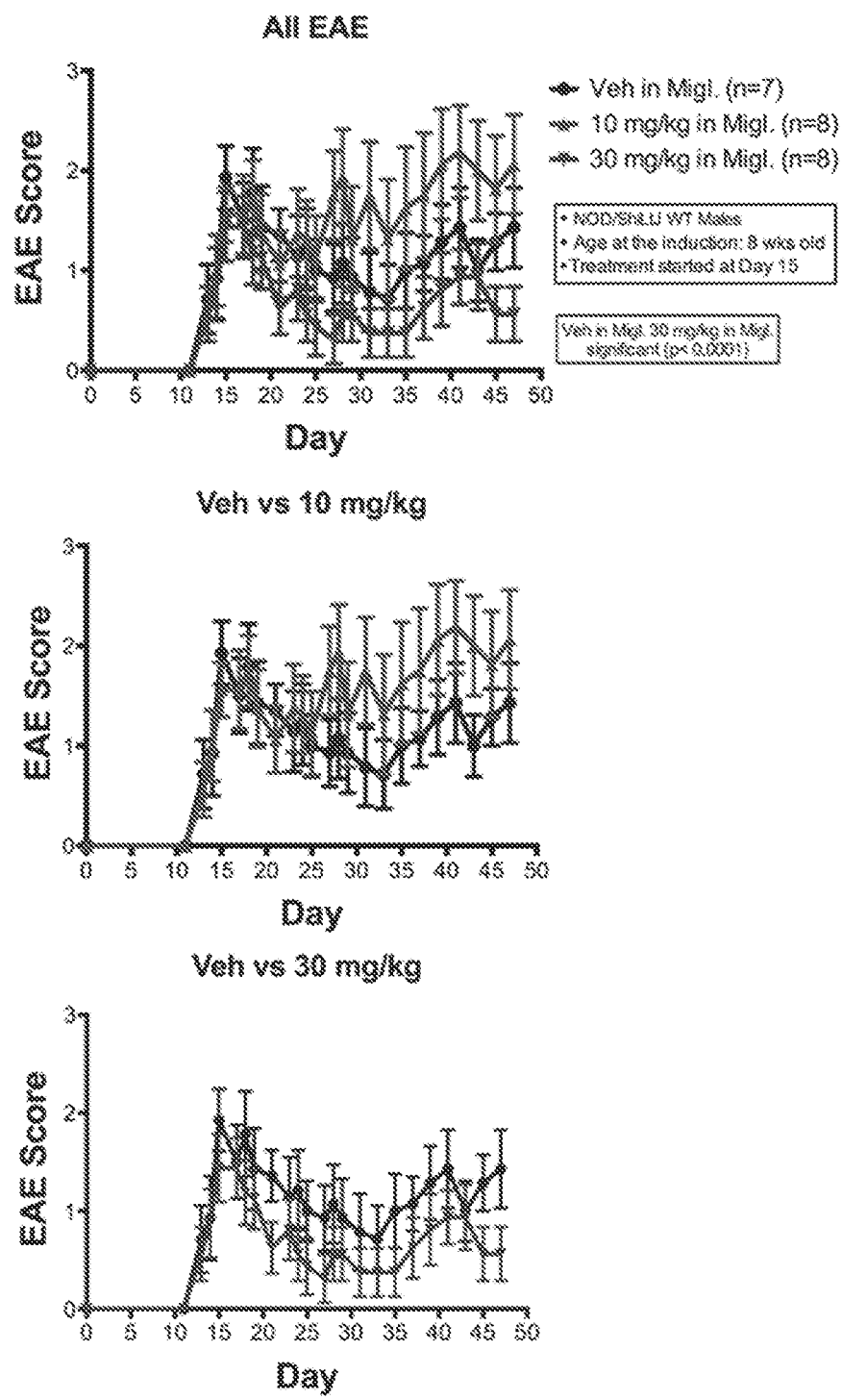
FIG. 10. EAE scores in NOD males under various treatment conditions. Standard EAE disease scores were ameliorated with AC-186 at 30 mg/kg, but not with AC-186 at 10 mg/kg, dose, each as compared to carrier vehicle alone (miglyol).
Figure 11:
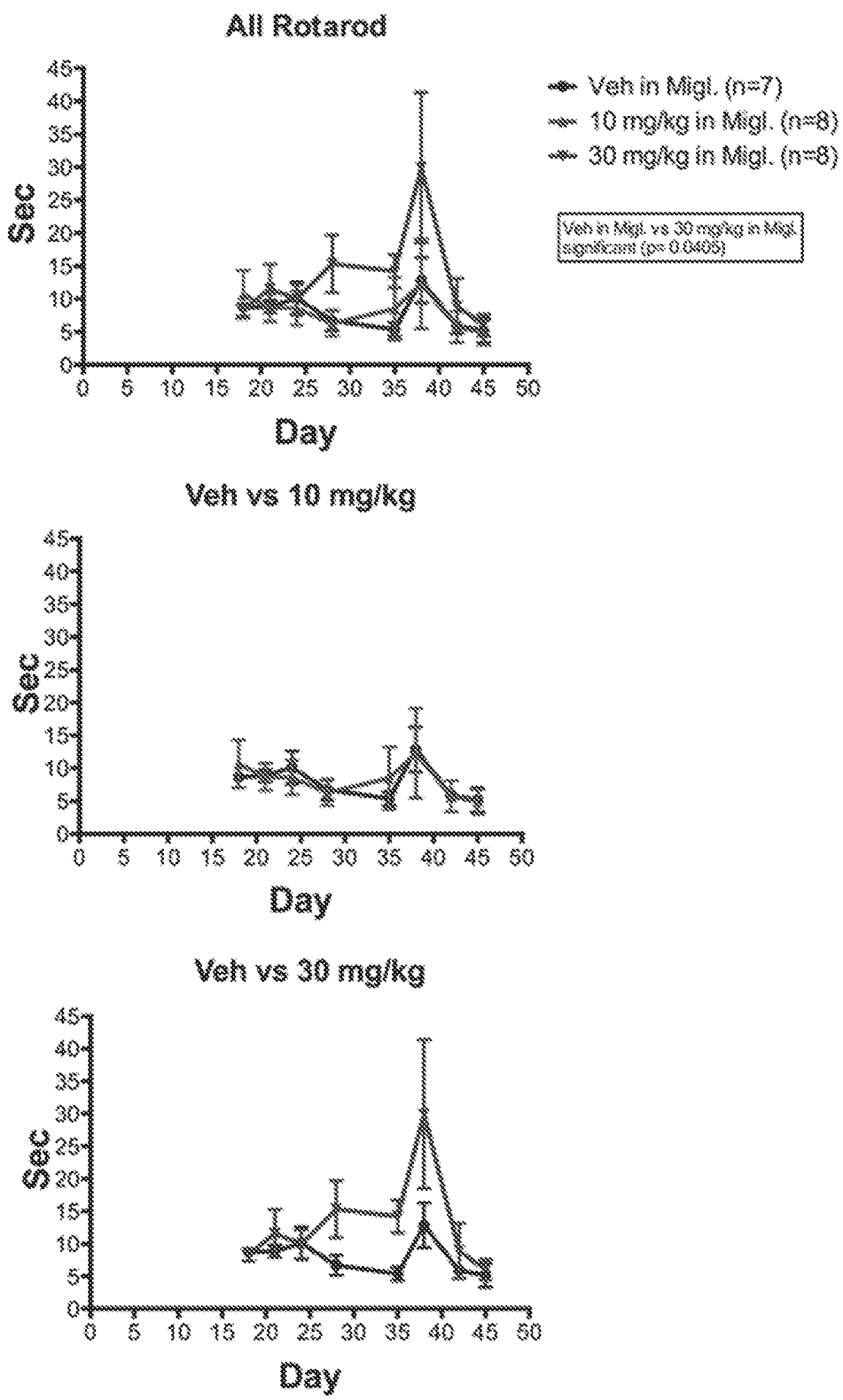
FIG. 11. EAE Rotarod times for NOD males under various treatment conditions. Rotarod performance was relatively poor in all male NOD groups with no significant difference between treatment groups.

The effect of AC-186 was assessed in male NOD mice using a MOG-induced EAE model. The efficacy of AC-186 was tested in miglyol vehicle only. AC-186 improved EAE scores relative to vehicle only for mice receiving 30 mg/kg in miglyol (p<0.0001) (FIG. 10). Mice treated with AC-186 displayed no significant improvement in performance in the rotarod experiment relative to mice treated with vehicle only (FIG. 11).

Example 7

Figure 12:
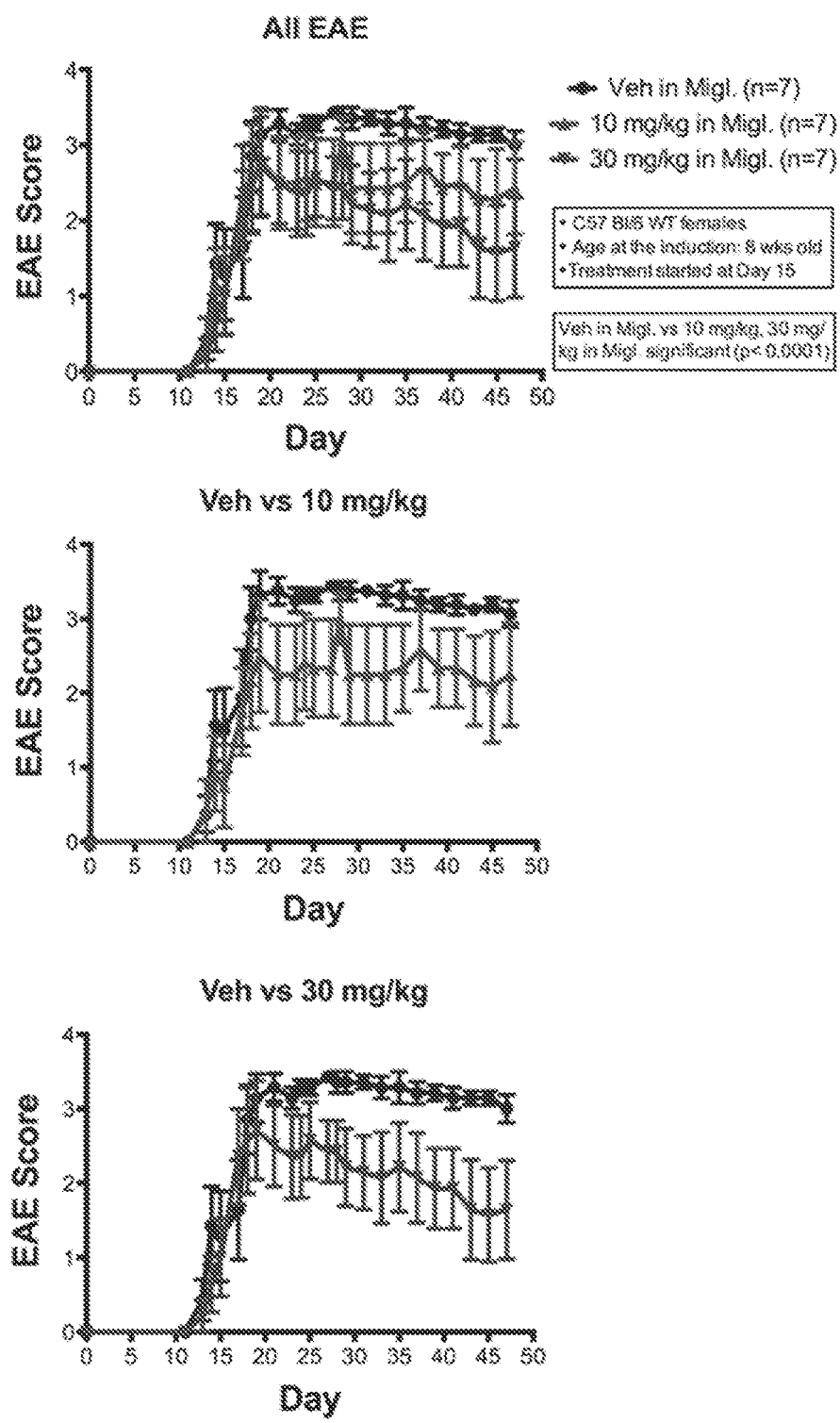
FIG. 12. EAE scores for C57BL/6 females under optimized treatment conditions. Standard EAE disease scores were ameliorated with AC-186 at 30 mg/kg and 10 mg/kg (p<0.0001), each as compared to vehicle (miglyol).
Figure 13:
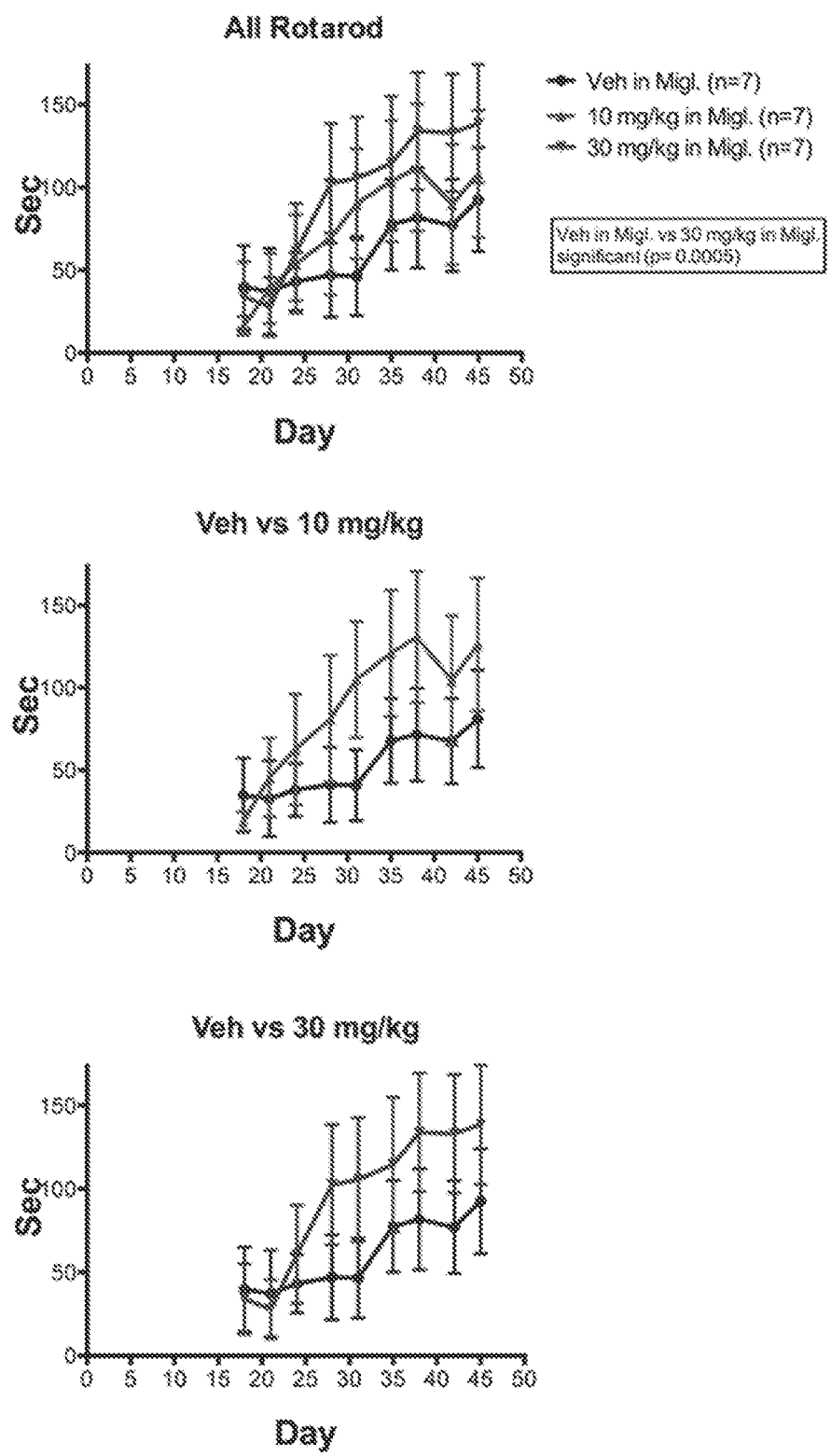
FIG. 13. Rotarod times for C57BL/6 females under optimized treatment conditions. Rotarod testing showed an improvement with the AC-186 30 mg/kg dose (p=0.0005).

Two doses of the AC-186 compound were tested in C57BL/6 female mice: medium (10 mg/kg) and high (30 mg/kg), each in a miglyol vehicle. Both the medium dose (10 mg/kg) and high dose (30 mg/kg) displayed significant efficacy in ameliorating the standard EAE clinical scores relative to the miglyol vehicle alone (p=0.0001) (FIG. 12). Additionally, the high dose (30 mg/kg) displayed significant efficacy in the rotarod experiment relative to the miglyol vehicle alone (p=0.0005) (FIG. 13).

TABLE 1

Summary of standard EAE and rotarod scores

| Mouse Strain | Sex | AC186 | Vehicle | Standard EAE Score (Results) | Rotarod Score |
|---|---|---|---|---|---|
| C57BL/6 | F | 30 mg/kg | miglyol | **** | *** |
| C57BL/6 | M | 30 mg/kg | miglyol | **** | **** |
| NOD | F | 30 mg/kg | miglyol | **** | n.i. |
| NOD | M | 30 mg/kg | miglyol | **** | n.i. |
| C57BL/6 | F | 10 mg/kg | miglyol | **** (less robust than 30 mg/kg) | n.s. |
| C57BL/6 | M | 10 mg/kg | miglyol | N/A | N/A |
| NOD | F | 10 mg/kg | miglyol | **** | n.i. |
| NOD | M | 10 mg/kg | miglyol | n.s. | n.i. |
| C57BL/6 | F | 30 mg/kg | sesame | * | n.s. |
| C57BL/6 | M | 30 mg/kg | sesame | n.s. | n.s. |
| NOD | F | 30 mg/kg | sesame | n.s. | n.i. |
| NOD | M | 30 mg/kg | sesame | N/A | N/A |
| C57BL/6 | F | 10 mg/kg | sesame | n.s. | n.s. |
| C57BL/6 | F | 3 mg/kg | sesame | n.s. | n.s. | n.s. = not significant;
N/A = not applicable, not done;
*p < 0.05,
***p = 0.0004,
****p < 0.0001
n.i. = not informative;
NOD females and NOD males have very poor rotarod performance, and thus the rotarod experiment is not sensitive in the NOD strain.

Example 8

Figure 14:
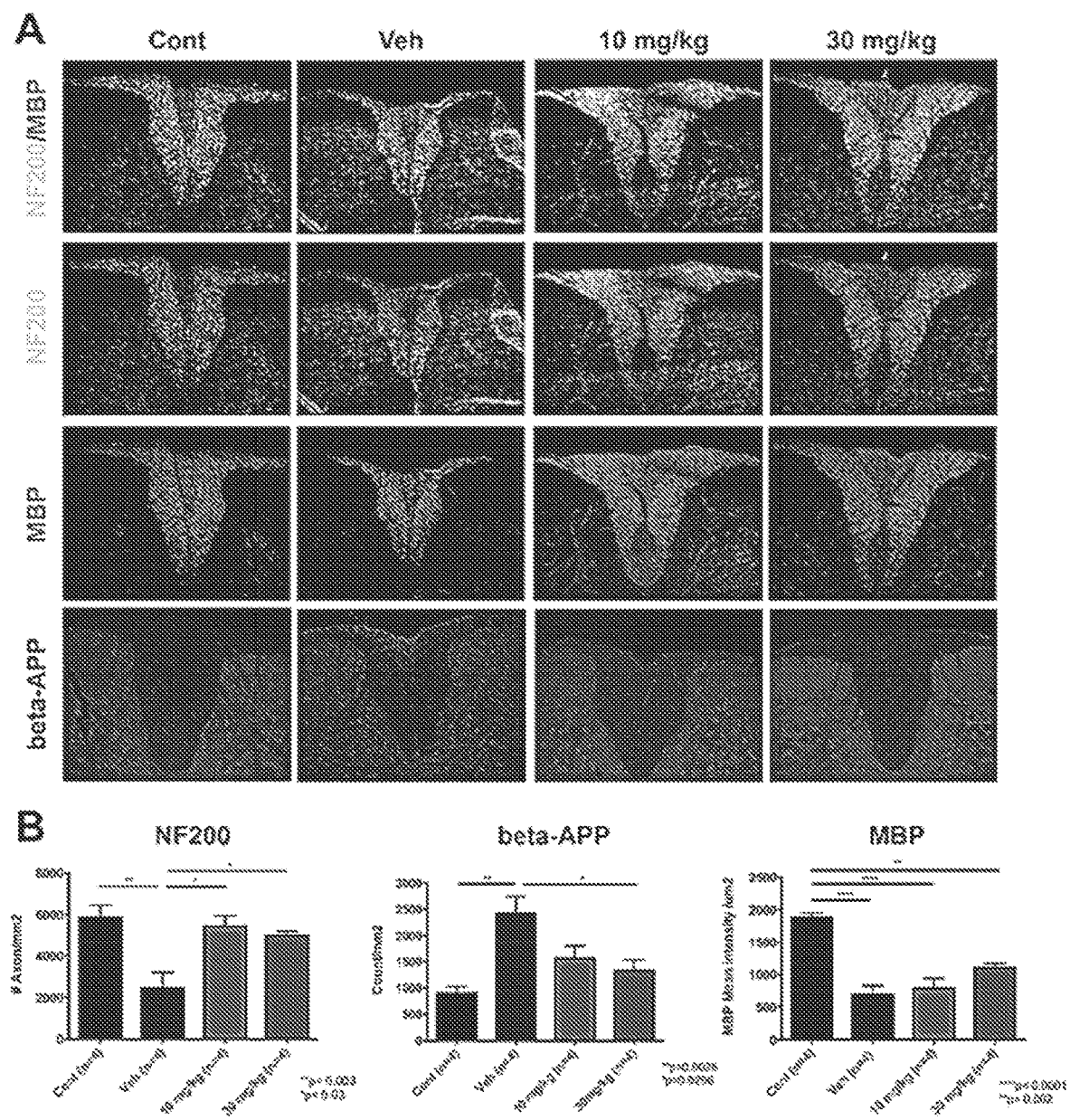
FIG. 14. AC-186 post-treatment during EAE: effects on axonal densities, beta-APP, and myelin in spinal cord. Pathology was performed on spinal cords of C57BL/6 females with EAE under optimized treatment conditions with AC-186 administered at either 30 mg/kg or 10 mg/kg, each in miglyol versus carrier vehicle alone.

Neuroprotective effects of AC-186 were observed by NF200 and beta-APP staining, with each of the 30 mg/kg and the 10 mg/kg doses (FIG. 14). C57BL/6 female mice were treated with AC-186 at 30 mg/kg/every other day in miglyol vehicle, 10 mg/kg/every other day in miglyol vehicle or with miglyol vehicle alone then underwent immunohistochemistry for axonal and myelin integrity using antibody staining for NF200, beta-APP and MBP. NF200 indicated axonal integrity with decreases indicating axonal loss, beta-APP also indicated axonal integrity with increases indicating axonal damage, and MBP staining indicated myelin integrity with decreases indicating demyelination during EAE. AC-186 30 mg/kg/every other day treatment in EAE significantly preserved axon numbers (NF200) and reduced axonal damage (beta-APP), with a trend for sparing myelin (MBP). These beneficial effects on axons in spinal cord are consistent with protective effects on clinical scores as assessed by EAE standard scores and rotarod performance above.

Figure 15:
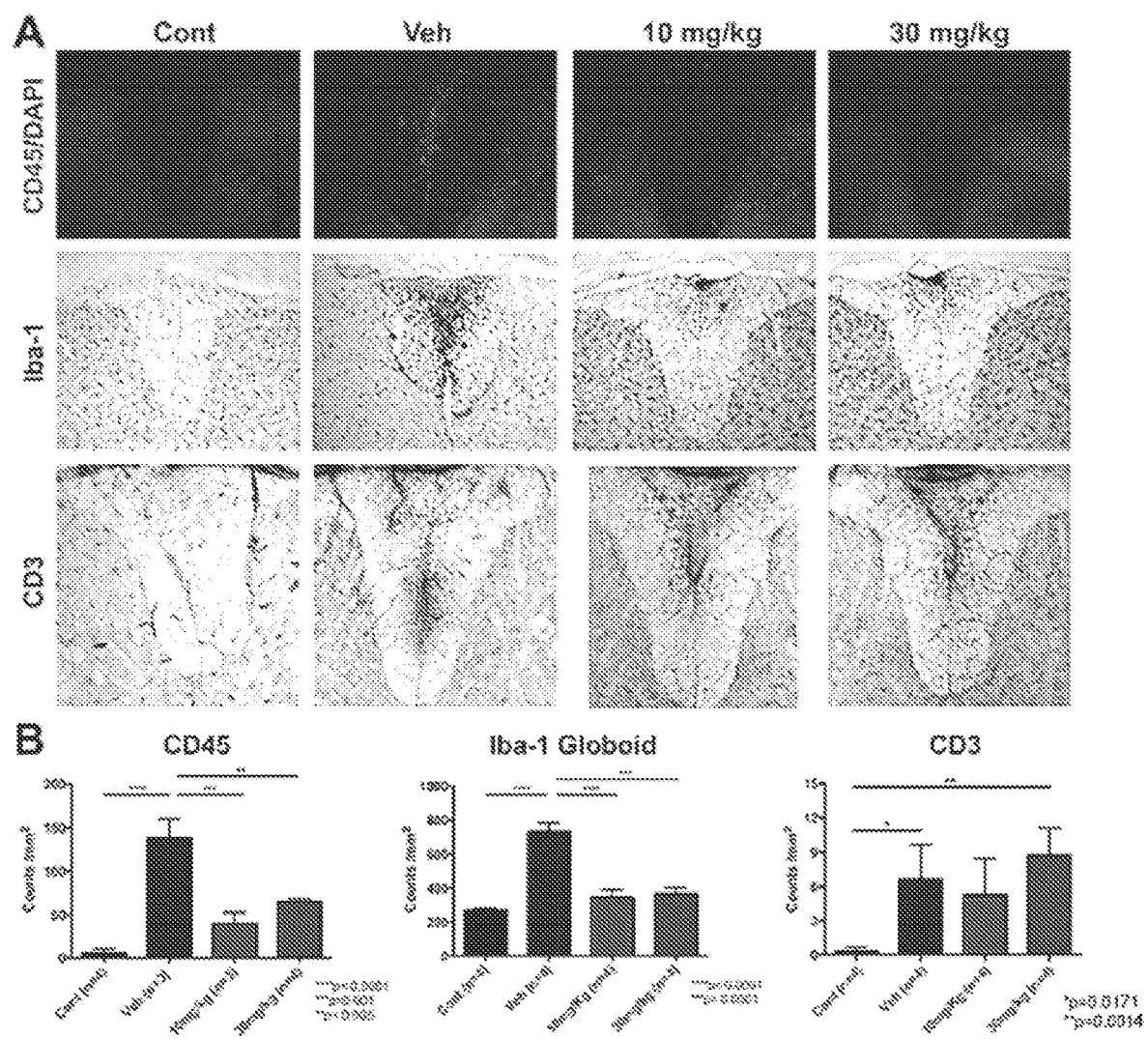
FIG. 15. AC-186 post-treatment during EAE: effects on macrophages and T cells. Further neuropathology was done on spinal cords from FIG. 14, here focusing on immune cell infiltrates.

Neuropathology of spinal cords focusing on immune cells is shown in FIG. 15. Regarding the assessment of immune cells by neuropathology, in contrast to previous experiments with DPN, which showed no significant effect on CD45 staining in the CNS, AC-186 treatment at both the 10 mg/kg and the 30 mg/kg doses reduced CD45 staining. To determine which immune cell population was reduced, Iba-1 stained cells with globoid morphology were used to assess macrophages and CD3 staining was used to assess T lymphocytes. AC-186 treatment at both the 30 mg/kg and the 10 mg/kg dose each reduced Iba-1 globoid cell staining, while neither AC-186 dose affected levels of CD3 staining.

These data are consistent with protective effects on clinical EAE scores. Effects on myelin staining were much less striking as compared to effects on axons as has been previously observed. Surprisingly, in contrast to previous experiments with DPN, which showed no effect on CD45 or Iba-1 globoid cell staining, AC-186 treatment reduced CD45 and Iba-1 globoid cell staining. However, neither dose of AC-186 affected levels of CD3 staining (FIG. 15). Whether the effect of AC-186 on reducing Iba-1 globoid cells was due to a reduction in macrophage infiltration into the CNS or due to a reduction in the transition of CNS resident cells to the globoid morphology as a reaction to less axonal damage during AC-186 treatment remains unknown. The observation that T lymphocyte levels were unaffected by AC-186 treatment suggests that the adaptive immune response is not affected by treatment like the innate immune response is.

Taken together, these results suggest that ER beta ligands differ in their effect on CD45 and other immune marker staining, which can have therapeutic and mechanistic implications for the treatment of MS subtypes.

MRI Methods

MRI Acquisition.

Mice were anesthetized with isofluorane and their heads secured with bite and ear bars. Respiration rate was monitored and the mice were maintained at 37° C. using a circulating water pump. In vivo magnetic resonance imaging was performed using a 200 mm horizontal bore 7.0 T Bruker imaging spectrometer with a micro-imaging gradient insert with a maximum gradient strength of 100 G/cm and 30 mm birdcage RF coil (Bruker Instruments, Billerica, Mass.). An actively decoupled quadrature surface coil array was used for signal reception and a 72-mm birdcage coil was used for transmission. Images were acquired and reconstructed using ParaVision 5.1 software. Imaging parameters were as follows: rapid-acquisition with relaxation enhancement (RARE) sequence, matrix dimensions=256×128×64; field of view=3.84 cm×1.92 cm×0.96 cm; repetition time (TR) =3500 ms; apparent time to echo (apparent TE)=32 ms; echo train length=16; total scan time=37 mins. Spatial resolution was 150 µm$^3$ per voxel.

MRI Analysis.

Images were skull-stripped using the Brain Surface Extractor (BSE) and residual non-brain signal was removed by a single operator manually editing the masks using BrainSuite 11a and bias-field inhomogeneities removed using the N3 correction. After inhomogeneity correction, a minimum deformation atlas (MDA) was produced. Images were spatially and intensity normalized to the MDA using a rigid-body transformation and an intensity rescaling cost function in Alignlinear (AIR). This process permits the comparison of images in a standard space correcting for both gross positional and intensity differences, yet preserving anatomically significant local changes. Following creation of this atlas, cerebral cortices and cerebella were manually labeled on the atlas. The labels were then warped onto the individual spatially normalized images to produce standardized estimates of gray matter volumes in individual subjects. All automated image processing was performed using the LONI Pipeline Processing Environment on an 8-processor core Mac Pro computer (Apple, Cupertino, Calif.).

Cerebral cortex and cerebellum labels were based on the Mouse Atlas Project 2003 mouse brain atlas. For clarity and consistency, the cerebral cortex label was bounded ventrally by the plane inferior to the most anterior point of the corpus callosum at midline. Importantly, this label contained the somatosensory regions (primary and secondary) and the motor cortex (primary and secondary). Additional anatomical information was obtained from the Franklin and Paxinos mouse brain atlas (Franklin and Paxinos, 2008).

Statistics.

Global and regional brain volume changes in EAE mice and control animals were compared with repeated measures ANOVAs using SPSS 22 (IBM, Armonk, N.Y.). If Mauchly's test indicated that the assumption of sphericity had been violated (p<0.05), then the degrees of freedom were corrected using the Huynh-Feldt estimates of sphericity. Regression analysis and Welch's t-tests were performed in Excel 2011 (Microsoft, Redmond, Wash.). All results are presented as mean±standard deviation.

Example 9

Figure 16:
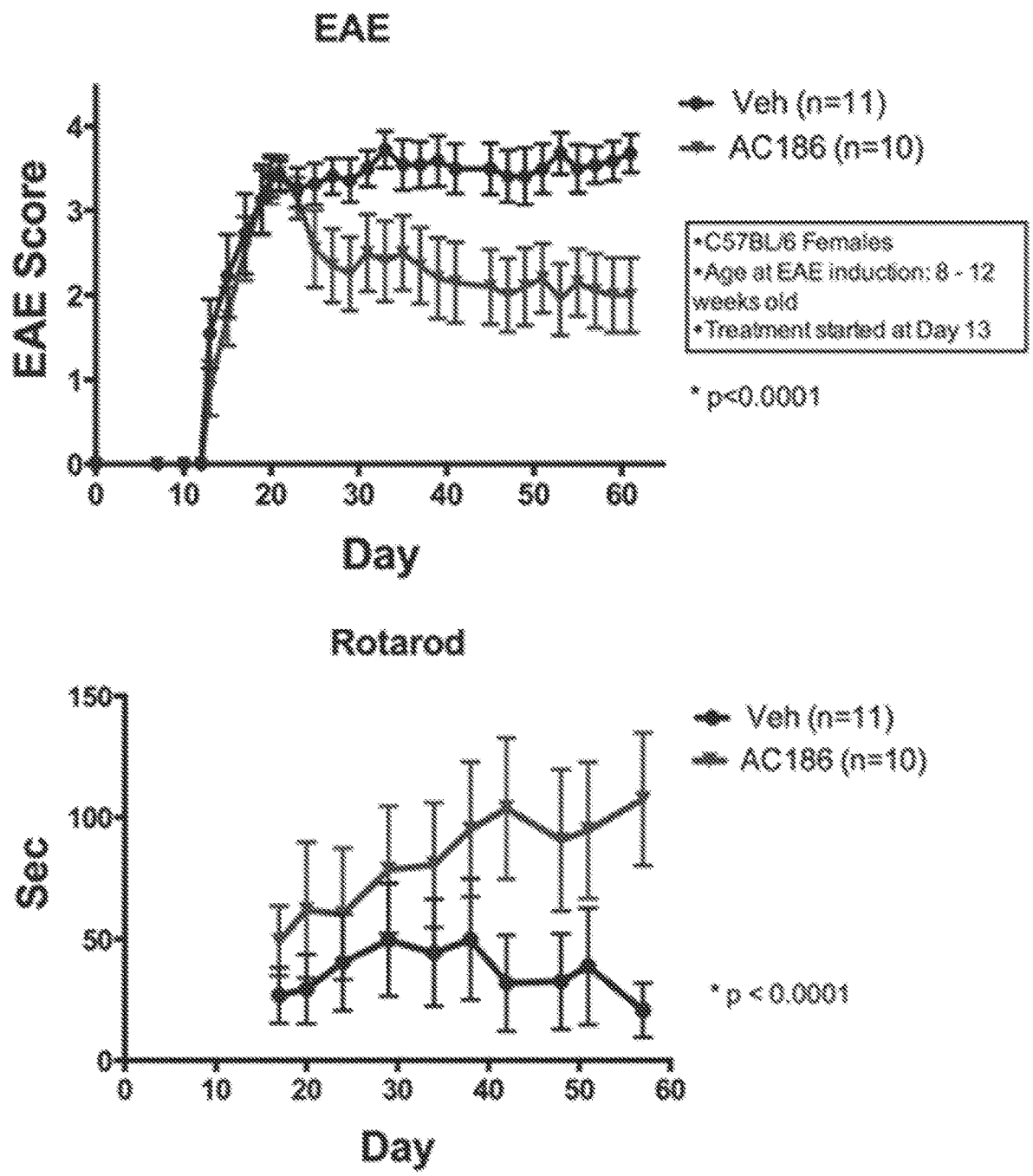
FIG. 16. EAE scores and rotarod times for female C57BL/6 mice who received 30 mg/kg AC-186 in miglyol for subsequent in vivo MRI of the brain followed by neuropathologic analyses of cerebrum and cerebellum. (Top) Standard EAE disease scores were ameliorated in female C57BL/6 mice treated with AC-186 at 30 mg/kg as compared to vehicle (miglyol), p<0.0001. (Bottom) Rotarod testing showed significant improvement with the AC-186 30 mg/kg as compared to vehicle (miglyol), p<0.0001.

Female C57BL/6 mice treated with AC-186 at 30 mg/kg underwent in vivo, longitudinal MRI scanning at day 0, 30, and 60 after EAE induction. The mice treated with AC-186 displayed beneficial effects for both standard EAE clinical scores and for rotarod times, similar to the effects observed in Example 7 (FIG. 16). Whole brain, cerebral cortex and cerebellar volumes were determined at each EAE time point in female C57Bl/6 mice that were treated with either AC-186 (AC-186) or vehicle (EAE), as well as in age- and sex-matched healthy control mice (NOR).

Mice underwent in vivo, longitudinal MRI scanning at day 0, 30, and 60 after EAE induction. Whole brain, cerebral cortex and cerebellar volumes were determined at each EAE time point in female C57Bl/6 mice that were treated with either AC-186 (AC-186, 30 mg/kg/every other day) or vehicle (EAE), as well as in age- and sex-matched healthy control mice (NOR).

NORMAL vs. EAE.

Figure 17:
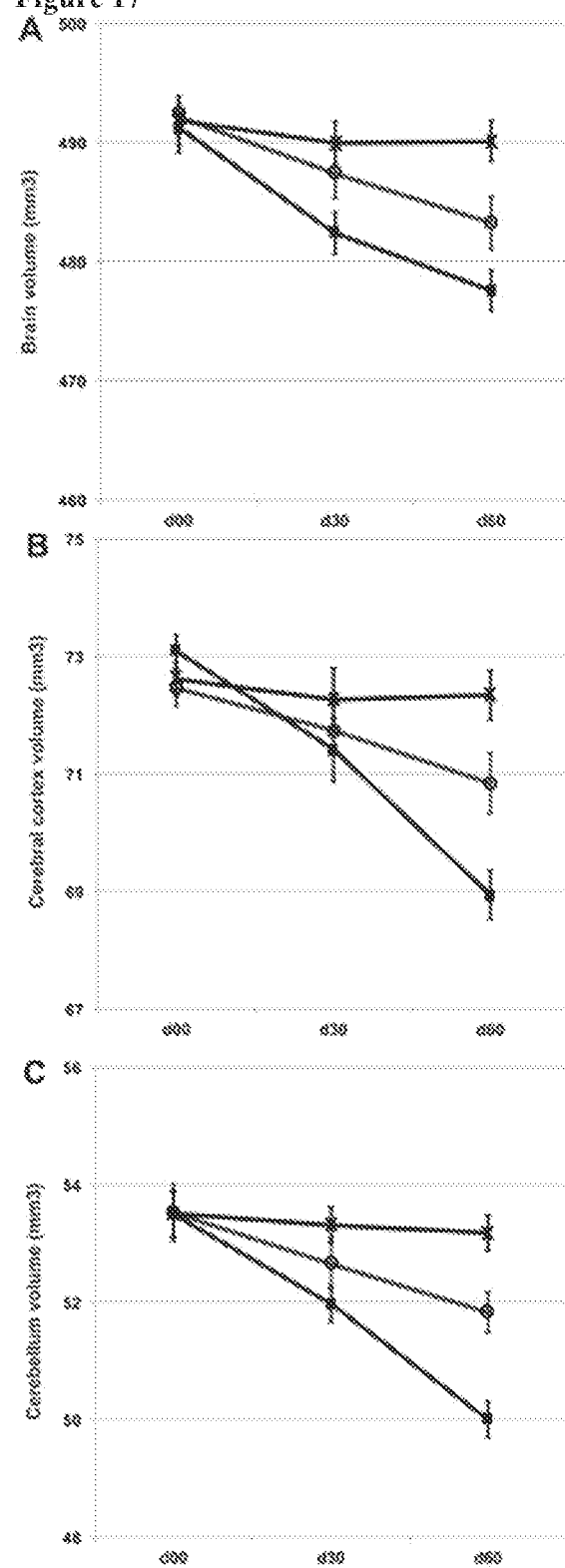
FIG. 17. AC-186 treatment protects against Whole Brain, Cortical and Cerebellar Atrophy by in vivo MRI in EAE.

Whole brain volumes of both NOR (black lines) and EAE vehicle mice were plotted against the disease duration (starting with the scans prior to disease induction) (FIG. 17A). In order to quantify the significance of the decreases in whole brain volume observed in individual animals, a repeated-measures ANOVA was performed to assess the effect of time on whole brain volume. Brain volume remained stable over time in the NOR group, but showed a gradual decrease in the EAE group (time×group interaction p=1.1×10$^{-7}$). The volume of the whole brain of mice sixty days after disease induction (d60) was 490 mm$^3$ (3.2 mm$^3$) in NOR mice and 478 mm$^3$ (3.7 mm$^3$) in EAE mice, indicating a 4.7% decrease (p=5.3×10$^{-6}$) in volume.

Cerebral cortex volumes of NOR and EAE mice were plotted against disease duration and a similar pattern was observed (FIG. 17B). Cerebral cortex volumes were stable in the NOR group, while gradually decreasing in the EAE group (time×group interaction p=4.0×10$^{-6}$). The volume of the cerebral cortex at sixty days after disease induction (d60) was 72.3 mm$^3$ (1.4 mm$^3$) in NOR mice and 68.9 mm$^3$ (1.8 mm$^3$) in EAE mice, a 4.7% decrease (p=1.5×10$^{-4}$) in volume.

Similarly, a progressive loss of cerebellar volume during EAE was observed in EAE mice compared to NOR mice (time×group interaction p=1.1×10$^{-5}$) (FIG. 17C). The volume of the whole cerebellum at sixty days after disease induction (d60) was 53.2 mm$^3$ (1.1 mm$^3$) in NOR mice and 50.0 mm$^3$ (1.1 mm$^3$) in EAE mice, a 6.0% decrease (p=3.1×10$^{-6}$) in volume.

These results demonstrated that whole brain, cerebral cortex and cerebellum volume decreases over time in mice with EAE.

AC-186 EAE vs. Vehicle EAE.

A decrease in the rate of atrophy was observed in AC-186 treated mice compared to vehicle treated EAE mice when whole brain volumes were plotted against the disease duration (starting with the scans prior to disease induction) (FIG. 17A). In order to quantify the effect of AC-186 treatment on EAE mice, a repeated-measures ANOVA was performed. Brain volume decreased in both EAE and AC-186 mice, however this brain volume decrease was significantly smaller in AC-186 treated EAE mice (time×group interaction p=0.0013). The volume of the whole brain sixty days after disease induction (d60) was 483 mm$^3$ (7.0 mm$^3$) in AC-186 treated EAE mice and 478 mm$^3$ (3.7 mm$^3$) in vehicle treated EAE mice, indicating a 2.7% difference (p=0.021) in volume.

Cerebral cortex volumes of AC-186 treated EAE mice and vehicle treated EAE mice were plotted against disease duration and a similar pattern was observed (FIG. 17B). Cerebral cortex atrophy rates were decreased in AC-186 treated EAE mice compared to vehicle treated EAE mice (time×group interaction p=0.0035). The volume of the cerebral cortex at sixty days after disease induction (d60) was 70.8 mm$^3$ (1.6 mm$^3$) in AC-186 treated EAE mice and 68.9 mm$^3$ (1.8 mm$^3$) in vehicle treated EAE mice, a 5.0% difference (p=0.014) in volume.

When cerebellar volume was plotted against disease duration in AC-186 treated EAE mice and vehicle treated EAE mice, volume decreases over time were again observed (FIG. 17C). However, AC-186 treatment decreased the amount of volume loss compared to vehicle treatment (time×group interaction p=9.5×10$^{-4}$). The volume of the whole cerebellum at sixty days after disease induction (d60) was 51.8 mm$^3$ (1.1 mm$^3$) in AC-186 treated EAE mice and 50.0 mm$^3$ (1.1 mm$^3$) in vehicle treated EAE mice, a 3.5% difference (p=0.0013) in volume.

Figure 18:
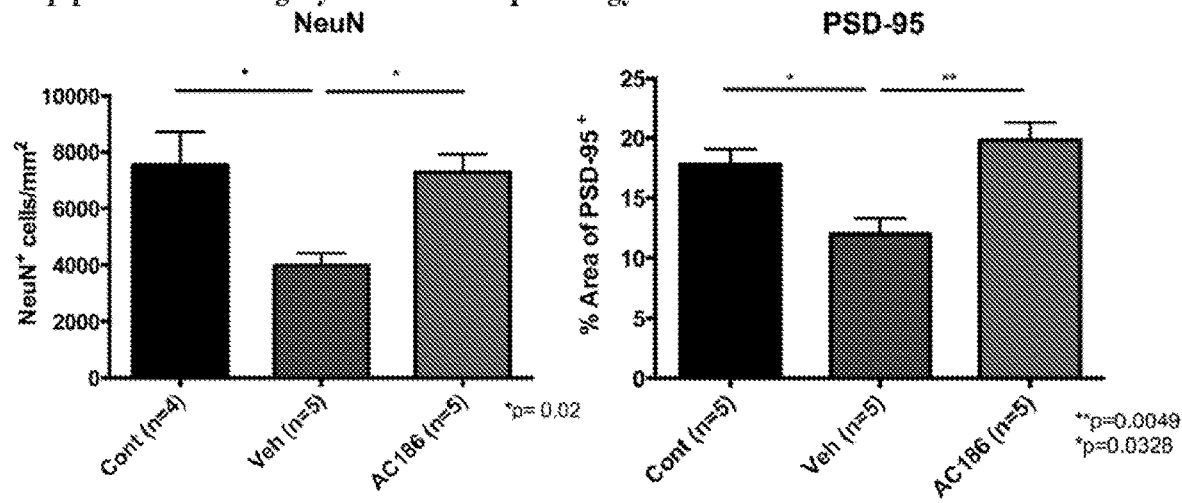
FIG. 18. AC-186 treatment protects against loss of cerebral and cerebellar neurons and synapses in gray matter. (Top row) Quantification of NeuN$^+$ neuronal cells in the cerebral cortex gray matter (left), and percent area of Post-Synaptic Density-95 (PSD-95, right) positivity in healthy controls (Cont), Vehicle (Veh), and AC-186-treated EAE mice. Vehicle treated EAE mice, as compared to age-matched healthy controls, had fewer numbers of NeuN$^+$ cortical neurons and less PSD-95 staining (p=0.02, NeuN; p=0.0328, PSD-95, one-way ANOVA). AC-186 treated EAE mice, as compared to Vehicle, had higher numbers of NeuN$^+$ cortical neurons and greater PSD-95 staining, with values comparable to age-matched healthy controls (p=0.02, NeuN, p=0.0049, PSD-95, one-way ANOVA). (Bottom row) Quantification of Calbindin$^+$ Purkinje cells (left) in the cerebellar gray matter, and PSD-95 (right) in cerebellar gray matter of age-matched healthy controls, Vehicle, and AC-186-treated EAE mice. Vehicle treated EAE mice, as compared to age-matched healthy controls, had fewer numbers of Calbindin$^+$ Purkinje cells and less PSD-95 staining (p=0.02, Calbindin; p=0.0328, PSD-95; one-way ANOVA). AC-186 treated EAE mice, as compared to Vehicle, had higher numbers of Calbindin$^+$ Purkinje cells and greater PSD-95 staining, with values comparable to age-matched healthy controls (p=0.04, Calbindin; p=0.0005, PSD-95; one-way ANOVA).
Figure 18:
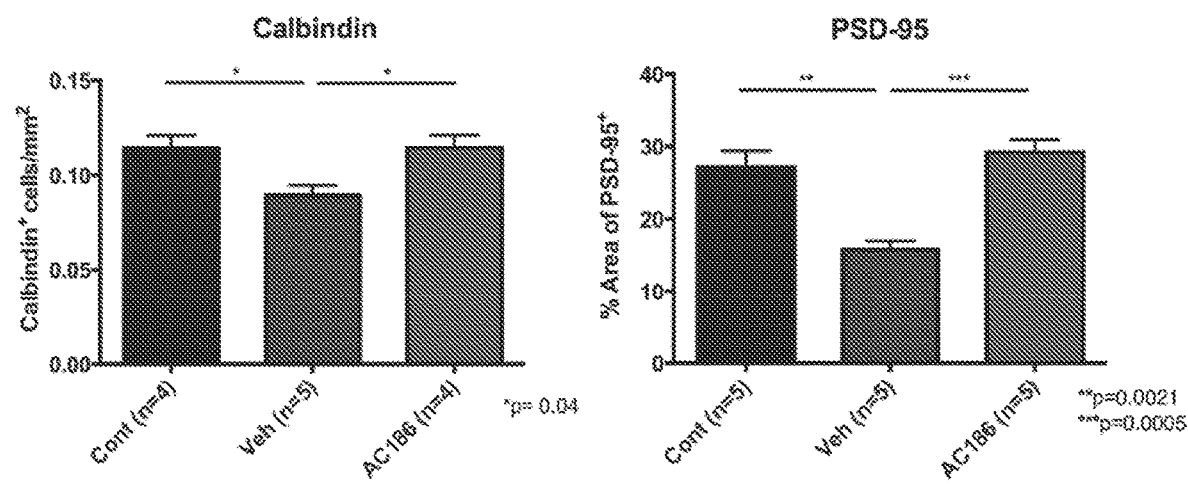

Cerebral and cerebellar neuropathology revealed that AC-186 treatment prevented neuronal cell (NeuN) and synaptic (PSD-95) loss in cerebral cortex gray matter (FIG. 18 top panel) and Purkinje neuronal cell (Calbindin) and synaptic (PSD-95) loss in the cerebellar cortex gray matter (FIG. 18 bottom panel).

Spinal Cord Neuropathy.

Figure 19:
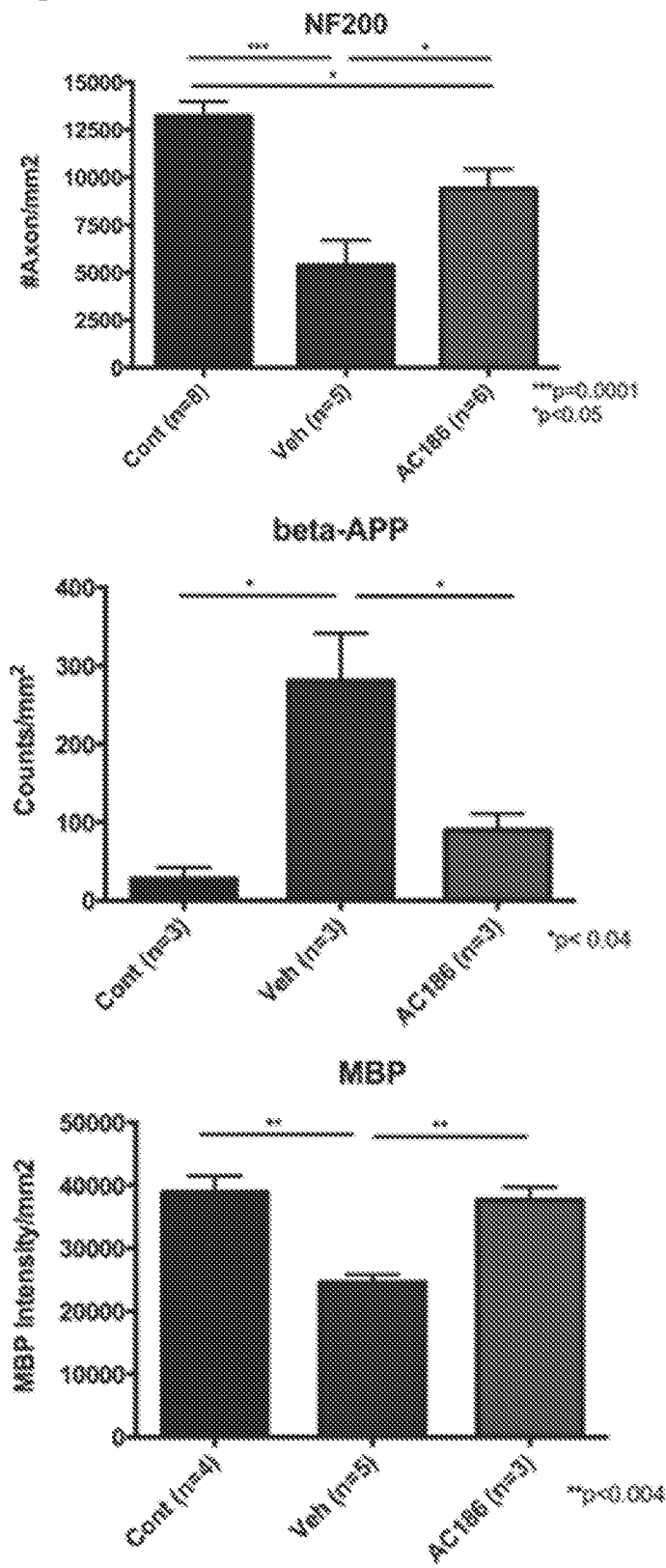
FIG. 19. AC-186 treatment protects against axonal loss, axonal damage, and myelin loss in spinal cord white matter. EAE mice receiving AC-186 at 30 mg/kg or vehicle were sacrificed. Quantification is shown of axonal densities by NF200 staining (top), beta-APP expression for axonal damage (middle), and myelin staining intensity by MBP (bottom). The vehicle treated (Veh) group as compared to matched healthy controls (Cont) showed significantly reduced axon numbers (left), increased beta-APP (middle) and reduced myelin (right). The AC-186 30 mg/kg treated EAE group showed significantly more axon numbers compared with the Vehicle treated EAE group (p<0.05, Veh vs AC-186 30 mg/kg). The beta-APP staining showed that the AC-186 30 mg/kg treated group had significantly less expression of beta-APP compared with the Vehicle treated EAE group (p<0.04, Veh vs AC-186 30 mg/kg). MBP staining showed that the AC-186 treatment group had higher MBP staining intensity as compared to vehicle (p<0.004, Veh vs AC-186 30 mg/kg). Three to five mice were examined for each treatment group. p-values were determined by one-way ANOVA. These results largely reproduce the results in FIG. 14, showing a protective effect on axons. However, a beneficial effect of AC-186 as compared to vehicle with regard to increased MBP staining, which was observed as a trend in the experiment in FIG. 14, was observed as significant in FIG. 19. Together, this data suggests that AC-186 treatment indeed has a beneficial effect on preserving not only axons, but also myelin, in the CNS.
Figure 20:
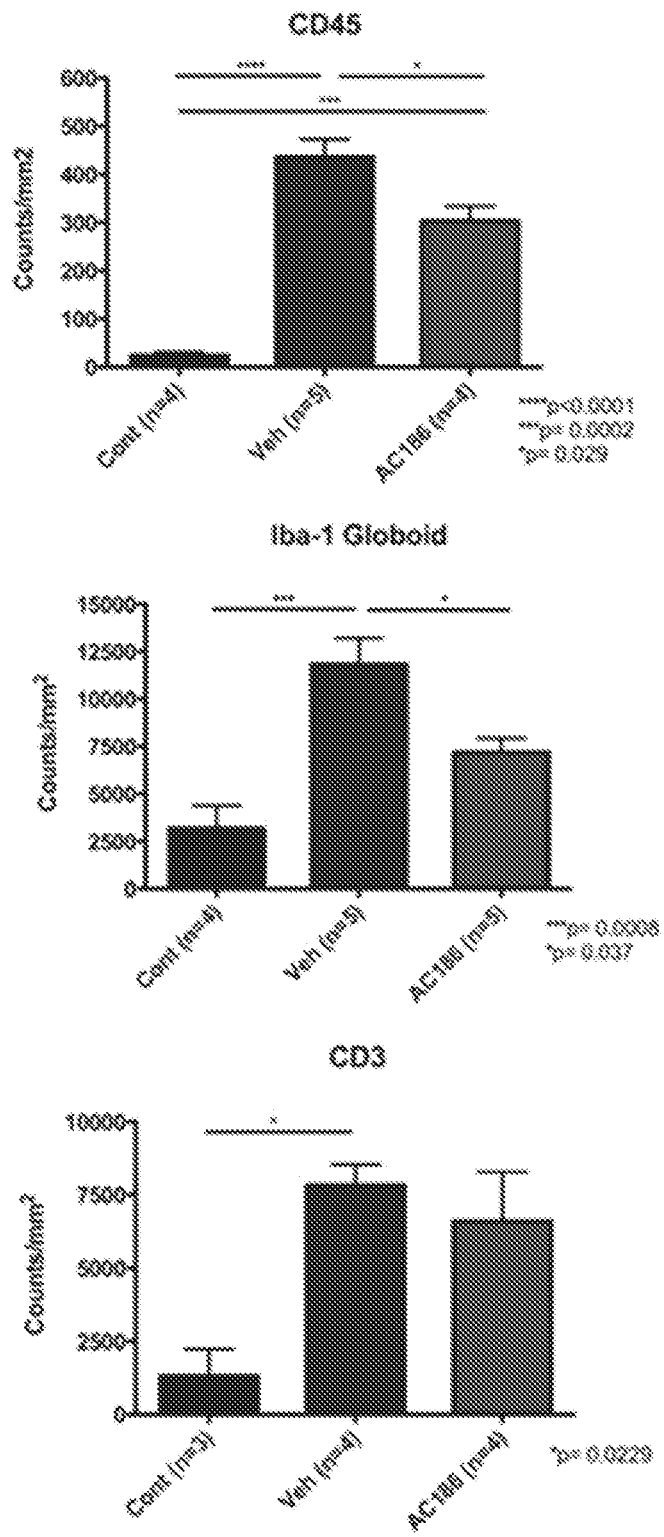
FIG. 20. AC-186 treatment during EAE: effects on macrophages and T cells. EAE mice receiving AC-186 at 30 mg/kg or vehicle were sacrificed. Quantification of CD45 immunoreactivity to quantify all immune cells (top), Iba-1 globoid to quantify macrophage like cells (middle), and CD3 to quantify T lymphocytes (bottom) was done. Vehicle treated EAE (Veh) as compared to matched healthy controls (Cont) showed significantly increased CD45 staining (top), increased Iba-1 globoid cells (middle), and increased CD3 cells (bottom). AC-186 30 mg/kg treated EAE groups showed a reduction of CD45 expression compared with the Vehicle treated EAE group (p=0.029, Veh vs AC-186 30 mg/kg). The AC-186 treatment group also showed a significant reduction in the number of Iba-1 stained cells with globoid morphology as compared with the Vehicle treated EAE group (p=0.037, Veh vs AC-186 30 mg/kg). There were no differences in the number of CD3 stained cells between the AC-186 treated group as compared to the Vehicle EAE treatment group. Three to five mice were examined for each treatment group. p-values were determined by one-way ANOVA. These results largely reproduce the results of FIG. 15, showing protective effects on macrophages but not T cells.

Neuropathology was repeated on spinal cord to confirm the results observed in Example 8. The results depicted in FIGS. 19 and 20 largely reproduce the results in FIGS. 14 and 15, showing a protective effect on axons. However, a beneficial effect of AC-186 as compared to vehicle with regard to increased MBP staining, that was observed as a trend in Example 8 (FIG. 14), was observed as significant (FIG. 19). Together, these data indicate that given a large enough sample size, AC-186 treatment does indeed have a beneficial effect on preserving myelin staining in the CNS. Thus, AC-186 treatment on EAE resulted in sparing of axons and myelin in spinal cords. Notably, the effect of AC-186 on lowering CD45 and Iba-1, but not CD3, which was observed in Example 8, was confirmed (FIG. 20). Lower CD45 and Iba-1 staining in the CNS during AC-186 treatment is consistent with a beneficial effect of AC-186 treatment on clinical scores since these cells are thought to contribute to the pathogenesis of disease.

Cerebellar and Cerebral White Matter Neuropathy.

Figure 21:
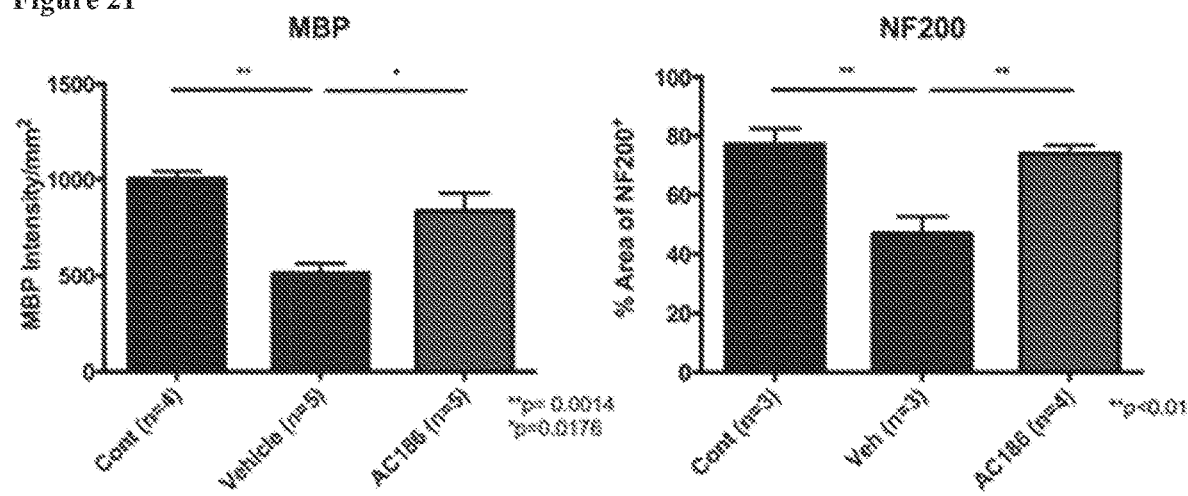
FIG. 21. AC-186 treatment during EAE: effects on cerebellar white matter. EAE mice receiving AC-186 at 30 mg/kg or vehicle were sacrificed. Quantification is shown of myelin staining intensity by MBP (left) and axonal densities by NF200 staining (right). The vehicle treated (Veh) group as compared to matched healthy controls (Cont) showed significantly reduced myelin (left) and reduced axon numbers (right). MBP staining showed that the AC-186 treated group had higher MBP staining intensity as compared to vehicle (p<0.0176, Veh vs AC-186 30 mg/kg). The AC-186 30 mg/kg treated EAE group showed significantly more axon numbers compared with the Vehicle treated EAE group (p<0.01, Veh vs AC-186 30 mg/kg). Three to five mice were examined for each treatment group. p-values were determined by one-way ANOVA.
Figure 22:
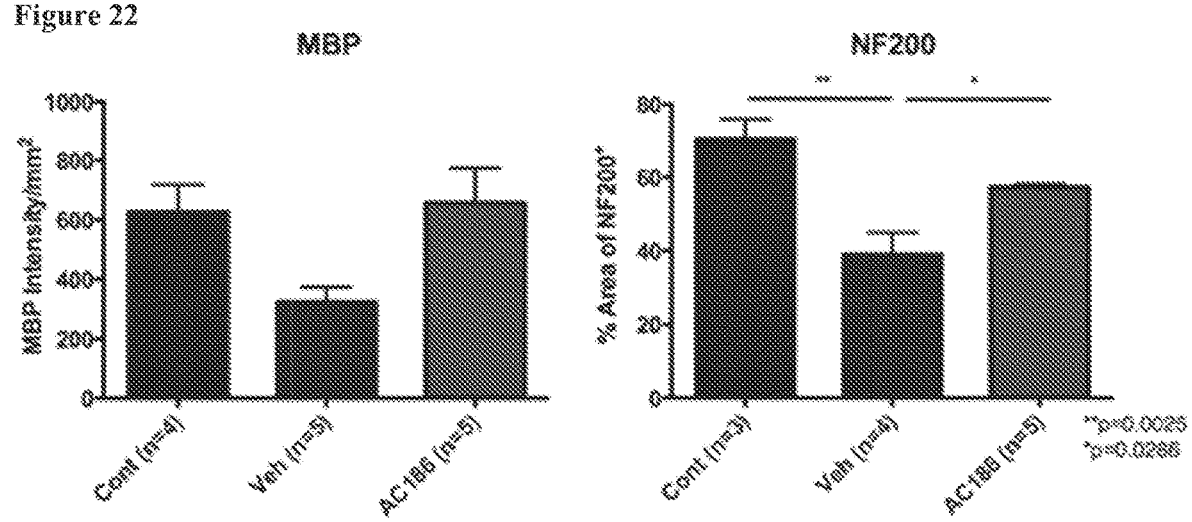
FIG. 22. AC-186 treatment during EAE: effects on cerebral white matter. Quantification is shown of myelin staining intensity by MBP (left) and axonal densities by NF200 staining (right) in the splenium of the corpus callosum of the cerebrum. The vehicle treated (Veh) group as compared to matched healthy controls (Cont) showed a trend for reduced myelin, but this did not reach significance (left), and a significant reduction in axon numbers (p=0.0025, Cont vs Veh) (right). Regarding the effect of AC-186 treatment, MBP staining showed that the AC-186 treated group had a trend for higher MBP staining intensity as compared to vehicle (left), but this did not reach significance. The AC-186 30 mg/kg treated EAE group showed significantly more axon numbers compared with the Vehicle treated EAE group (p=0.0286, Veh vs AC-186 30 mg/kg) (right). Three to five mice were examined for each treatment group. p-values were determined by one-way ANOVA.

As an extension of effects of AC-186 treatment on spinal cord white matter neuropathology, AC-186 treatment on cerebral and cerebellar white matter was assessed. AC-186 administered at 30 mg/kg/every other day had a protective effect on cerebellar and cerebral axons (NF200) and myelin (MBP) (FIGS. 21 and 22). These findings were consistent with the finding that AC-186 protected spinal cord white matter. Together, these data show a beneficial effect for AC-186 treatment initiated after disease onset, which reduced myelin and axonal loss in the white matter of the cerebellum and cerebrum during EAE.

Cerebellar and Cerebral Gray Matter Neuropathy.

Figure 23:
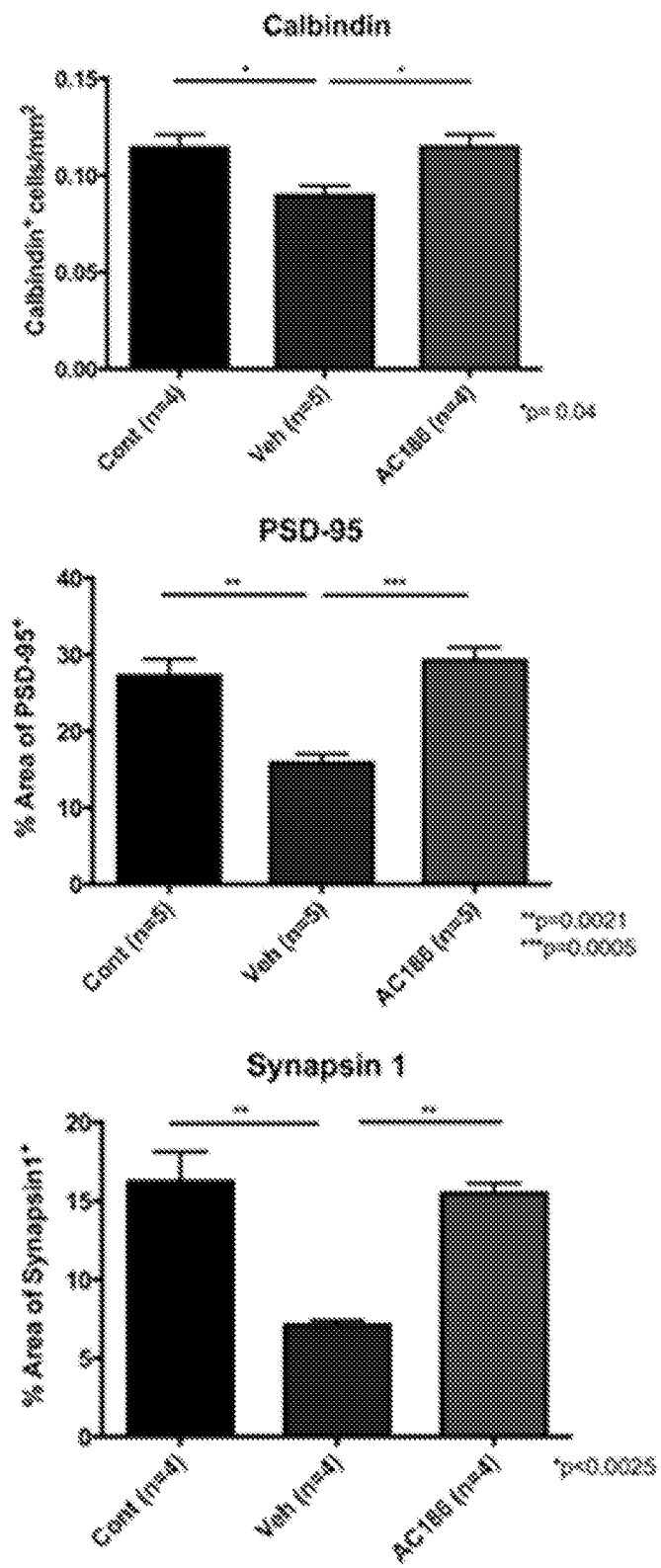
FIG. 23. AC-186 treatment during EAE: effects on cerebellar gray matter neurons and synapses. Quantification of Calbindin cells in the Purkinje cell layer, as well as PSD-95 and Synapsin-1 positivity in cerebellar molecular layer of age-matched healthy controls, Vehicle, and AC-186-treated EAE mice. Vehicle treated EAE mice, as compared to age-matched healthy controls, had fewer numbers of Calbindin$^+$ cells in the cerebellar Purkinje cell layer and less PSD-95 and Synapsin1 staining (p=0.02, Calbindin; p=0.0328, PSD-95; p=0.0021, Synapsin1, one-way ANOVA) in the molecular layer. AC-186 treated EAE mice, as compared to Vehicle, had higher numbers of Calbindin$^+$ cells in the Purkinje cell layer and greater PSD-95 and Synapsin1 staining in the molecular layer, with values comparable to age-matched healthy controls (p=0.04, Calbindin; p=0.0005, PSD-95; p<0.0025, Synapsin1, one-way ANOVA).
Figure 24:
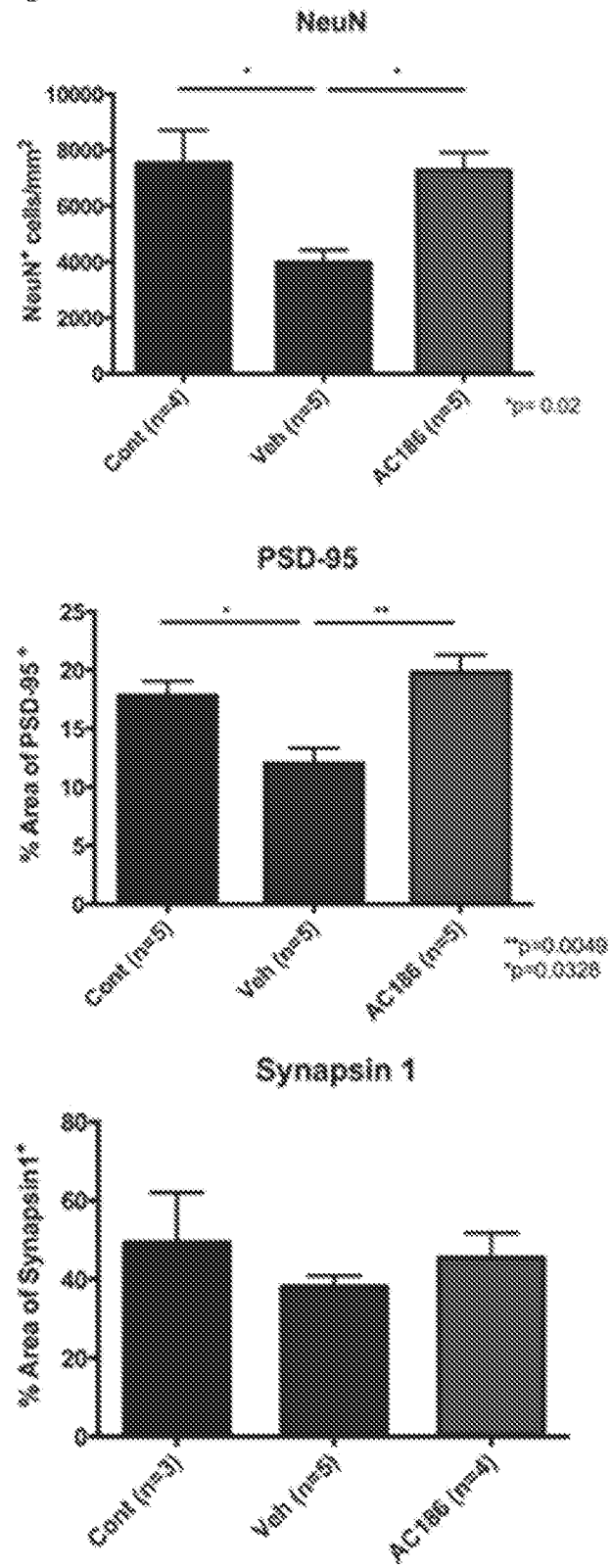
FIG. 24. AC-186 treatment during EAE: effects on cerebral gray matter neurons and synapses. Quantification of NeuN$^+$ neuronal cells, percent area of Post-Synaptic Density-95 (PSD-95) and presynaptic Synapsin-1 positivity in cerebral cortex of healthy controls (Cont), Vehicle (Veh), and AC-186-treated EAE mice. Vehicle treated EAE mice, as compared to age-matched healthy controls, had fewer numbers of NeuN$^+$ cortical neurons and less PSD-95 staining in the cerebral cortex (p=0.0$^2$, NeuN; p=0.0328, PSD-95, one-way ANOVA). AC-186 treated EAE mice, as compared to Vehicle, had higher numbers of NeuN$^+$ cortical neurons and greater PSD-95 staining in the cerebral cortex, with values comparable to age-matched healthy controls (p=0.02, NeuN, p=0.0049, PSD-95, one-way ANOVA). There were no significant differences in Synapsin-1 staining. Three to five mice were examined for each treatment group. p-values were determined by one-way ANOVA.
Figure 25:
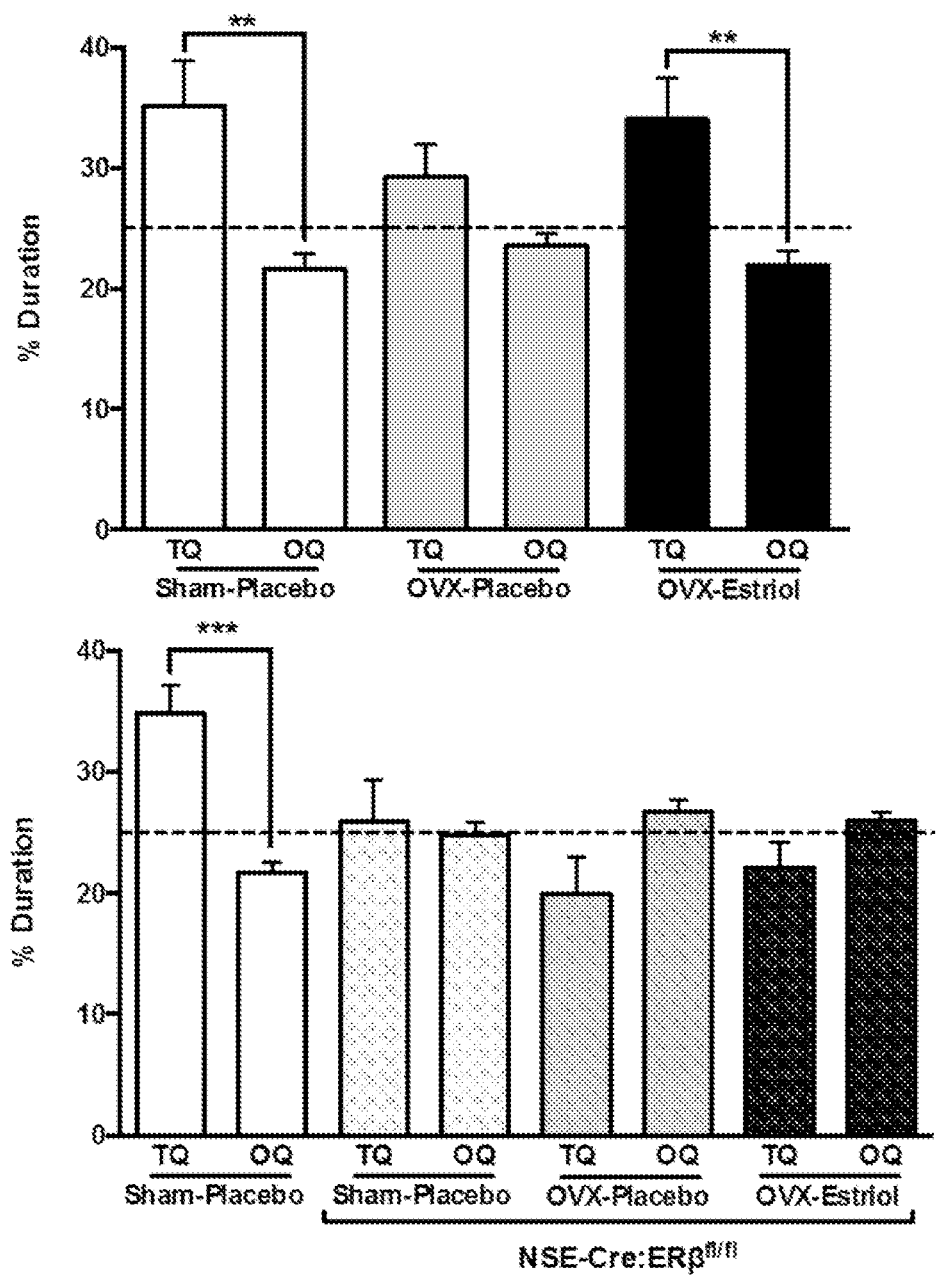
FIG. 25. Peripheral estrogens Improve performance on the Morris water maze via ERβ expressed on neurons. Healthy female C57BL/6 (with no EAE induced) were tested for cognitive performance (spatial memory) using the Morris water maze, whereby mice learn to spend more time in a target quadrant (TQ) as compared to three other quadrants (OQ). (Top graph) Sham-Placebo mice (SP, n=6) spent more time in the target quadrant due to proper learning, whereas ovariectomized, placebo-treated mice (OVX-Placebo, OP, n=7) did not show learning, thereby confirming that the loss of endogenous ovarian hormones causes cognitive disability. In contrast, ovariectomized, estriol-treated mice (OVX-Estriol, OE, n=7) displayed that the ability to learn may be restored with estriol treatment (p≤0.01, ANOVA-Sidak's posttest). (Bottom graph) To determine (a) whether ER beta is required for proper learning and, more specifically, (b) whether ER beta expression in neurons is required for learning, mice were generated that had ER beta conditionally knocked out using CreLox technology, with Cre driving the knock out in neurons via the neuron-specific enolase (NSE) promoter. Wild-type SP (n=7), but not SP NSE-Cre:Erβ$^{fl/fl}$ (n=7), OP NSE-Cre:Erβ$^{fl/fl}$ (n=7), or OE NSE-Cre:Erβ$^{fl/fl}$ (n=7) mice, spent significantly greater % duration in the TQ than in the OQ, averaged. (*p≤0.001, ANOVA-Sidak's posttest). These results suggest that, when ER beta is removed from neurons in the brain, mice lose the ability to learn. Further, these findings suggest that the ability of estriol to rescue learning is mediated by ER beta expression in neurons. The dashed line on the graphs indicates the time expected to be spent in a quadrant by random chance in the absence of learning (25%).

As an extension of effects of AC-186 treatment on cerebellar and cerebral white matter neuropathology, the effects of AC-186 treatment on cerebral and cerebellar gray matter was assessed. As shown in FIG. 23, AC-186 displayed a protective effect at a dose of 30 mg/kg/every other day for cerebellar cells (Calbindin+ Purkinje cells) and synapses (PSD-95 and Synapsin 1). Further, AC-186 displayed a protective effect at a dose of AC-186 30 mg/kg/every other day for cerebral cells (NeuN+ neurons) and synapses (PSD-95) (FIG. 24). No effect was observed for Synapsin 1 in cerebral gray matter, in contrast to cerebellar gray matter. These results are consistent with the previous findings on the differential effect of EAE on pre (Synapsin 1) versus post (PSD-95) synaptic protein expression (Du et al., *Proceedings of the National Academy of Sciences USA*, 111:2806-2806, 2014). Together, these data show a beneficial effect of AC-186 treatment, initiated after disease onset, in halting cellular and synaptic loss in cerebellar and cerebral gray matter during EAE.

Example 10

Examination of the Effect of Estrogen Receptor β Ligands, KBRV1 and KBRV2 on Neurodegeneration in the EAE Model.

Methods.

Animals: Female WT C57BL/6 mice age 6-8 weeks at the time of disease onset, were obtained from Jackson Laboratories (Bar Harbor, Me., USA). Animals were maintained in accordance with the guidelines set by the National Institute of Health and as mandated by the University of California Los Angeles Office for the Protection of Research Subjects, the Chancellor's Animal Research Committee, and the PHS Policy on Human Care and Use of Laboratory Animals.

Reagents: Two estrogen receptor β ligands, KBRV1 and KBRV2, were provided by Karo Bio (Huddinge, Sweden). Diarylpropionitrile (DPN) was used as a positive control during the experiment. MOG peptide, amino acids 35-55, was synthesized to >98% purity by Mimotopes (Clayton, Victoria, Australia).

Induction of EAE: In order to model brain inflammation, EAE was induced in the mice. First, the mice were immunized by subcutaneous injections into the left flank of 200 μg of MOG peptide, amino acids 35-55, and 200 μg of *Mycobacterium tuberculosis* in complete Freund's adjuvant. Immediately after immunization, mice received an intraperitoneal injection of 500 ng pertussis toxin dissolved in 400 μL phosphate buffered saline (PBS). Two days later, the mice received another intraperitoneal injection of pertussis toxin of the same quantity. Seven days after the initial immunization, the MOG immunization was repeated.

Treatment: The mice were treated with vehicle, KBRV1, KBRV2, or DPN seven days prior to disease induction. Treatment was administered every other day. DPN was administered as a positive control at a dose of 8 mg/kg. Doses of KBRV1 included 3 μmol/kg and 10 μmol/kg. Doses of KBRV2 were administered at 1 μmol/kg, 3 μmol/kg, and 10 μmol/kg.

Clinical Scoring: Animals were monitored daily for EAE signs based on a standard EAE 0 to 5 scale scoring system: 0, healthy; 1, complete loss of tail tonicity; 2, loss of righting reflex; 3, partial paralysis; 4, complete paralysis of one or both hind limbs; and 5, moribund.

Tissue Collection: In order to analyze the drug exposure of each animal, the plasma, brains, and spleen of the animals were taken from each dosing group in Trial 1 (except for the group that were administered DPN), as well as all groups in Trial 2, for bioanalysis. In Trial 3, the tissue was collected for histopathology.

Statistical Analysis: The results and measurements were evaluated using a repeated measure ANOVA model with Bonferonni correction. The statistical significance level was set at 0.05, so any calculated p-value less than 0.05 was considered significant.

Results.

Trial 1: Trial 1 tested KBRV1 doses of 3 μmol/kg and 10 μmol/kg, as well as KBRV2 doses of 10 μmol/kg. The results demonstrated that both KBRV1 and KBRV2 were effective at ameliorating EAE when compared to the vehicle treatment. The KBRV1 dose of 3 μmol/kg was effective but the 10 μmol/kg dose was not effective. In performing the statistical analysis, the F-test statistic of the 3 μmol/kg dose compared to the vehicle was 36.59, giving a p-value less than 0.0001. The KBRV2 dose of 10 μmol/kg was also effective when compared to the vehicle, giving an F-test statistic of 36.59 and a p-value of less than 0.0001.

Trial 2: Trial 2 tested alternative doses of KBRV2 at both the 3 μmol/kg and 10 μmol/kg level. The results demonstrated that KBRV2 was again effective in ameliorating EAE when compared to the vehicle treatment. The 3 μmol/kg dose resulted in an F-test statistic of 29.20 and a p-value of less than 0.0001 when compared to the vehicle treatment.

Trial 3: Trial 3 repeated the tests of Trial 2 to confirm whether both the 3 μmol/kg and 10 μmol/kg doses of KBRV2 were successful in ameliorating EAE. The results demonstrated that both doses were effective in ameliorating EAE. When comparing either dose to the vehicle treatments, the F-test statistic was calculated as 30.67, giving a p-value of less than 0.0001.

Treatment with ERβ ligand KBRV2 reduced demyelination and preserved myelin in spinal cords of mice with EAE in a dose dependent manner with greatest effects at the 10 μmol/kg dose and lesser effects at the 3 μmol/kg dose. Treatment with ERβ ligand KBRV2 reduced axonal loss in spinal cords of mice with EAE in a dose dependent manner with greatest effects at the 10 μmol/kg dose and lesser effects at the 3 μmol/kg dose. Further, treatment with ERβ ligand KBRV2 reduced local CNS inflammation and assessed by the global marker CD45 which stains all immune cells. This effect of ERβ ligand KBRV2 on inflammation within the CNS appears to be due to effects on T lymphocytes, and not macrophages.

Example 11

Ovariectomized mice (OVX-Placebo) display worse performance in the Morris water maze than control mice (Sham-Placebo) (FIG. 19, top panel). The administration of an estrogen improves performance for ovariectomized mice (OVX-Estriol) (FIG. 19, top panel). This effect is likely mediated by estrogen receptor β expressed by neurons because estrogen-mediated improvement is lost in mice comprising a conditional knockout of estrogen receptor β in a neuron-specific enolase-CRE mouse (NSE-Cre:ERβ$^{fl/fl}$; FIG. 19, bottom panel). Thus, estrogen receptor β ligands can likely protect against neuronal defects and disability during neurodegenerative processes.

EQUIVALENTS

Although the present invention has been described in terms of the embodiments above, numerous modifications and/or additions to the above-described embodiments would be readily apparent to one skilled in the art.

INCORPORATION BY REFERENCE

All of the patents, published patent applications, and other documents cited herein are hereby incorporated by reference.

What is claimed is:

1. A method of slowing cerebral cortex gray matter atrophy in a subject suffering from multiple sclerosis, comprising administering to the subject an estrogen receptor beta ligand and evaluating the subject's brain gray matter.

2. The method of claim 1, wherein the subject has greater than about 0.1%, about 0.2%, or about 0.3%, or about 0.4%, or about 0.5%, or about 0.6%, or about 0.7%, or about 0.8%, or about 0.9%, or about 1.0%, or about 1.1%, or about 1.2%, or about 1.3%, or about 1.4%, or about 1.5%, or about 2.0% brain gray matter atrophy per annum.

3. The method of claim 2, wherein evaluating the subject's gray matter comprises using an imaging technique selected from magnetic resonance imaging (MRI), fast fluid-attenuated inversion recovery (FLAIR), double inversion recovery (DIR), phase-sensitive inversion recovery (PSIR), ultra high-field MRI, magnetization transfer imaging (MTI), T1-relaxometry, diffusion tensor imaging (DTI), proton magnetic resonance spectroscopy (MRS)), and related techniques and combinations thereof, or surrogate marker selected from one or more of nogo receptor, kallikrein-6 (neurosin), cerebellin-1, ceruloplasmin, dickkopf-3 (rig-like 7-1), amyloid beta precursor-like protein 1, activated leukocyte cell adhesion molecule (CD166), neural cell adhesion molecule 2, neural epidermal growth factor like 2/cerebral protein-12, clusterin (apolipoprotein j, complement lysis inhibitor), brevican, neuronal cadherin, chitinase-3-like 1 protein, neogenin, multifunctional protein MFP (collagen alpha 1 (XVIII) chain; endostatin), dystroglycan 1, contactin 2, ephrin type a receptor 4, neural cell adhesion molecule L1 like protein, and contactin 1.

4. The method of claim 1, wherein the estrogen receptor beta ligand is a compound having the structure of formula I:

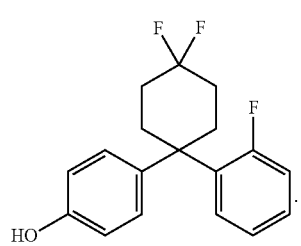

5. The method of claim 1, wherein the multiple sclerosis is relapsing-remitting multiple sclerosis, secondary-progressive multiple sclerosis, primary-progressive multiple sclerosis, or progressive-relapsing multiple sclerosis.

6. The method of claim 1, wherein the method further comprises administering to the subject an immunotherapeutic agent.

7. The method of claim 6, wherein the immunotherapeutic agent is selected from interferon-beta 1a, interferon-beta 1b, pegylated interferon-beta-1a, glatiramer acetate, natalizumab, mitoxantrone, fingolimod, teriflunomide, dimethyl fumarate, mycophenolate mofetil, paclitaxel, cyclosporine, corticosteroids, azathioprine, cyclophosphamide, methotrexate, cladribine, 4-aminopyridine, and tizanidine.

8. The method of claim 6, wherein the immunotherapeutic agent is glatiramer acetate.

9. The method of claim 8, wherein the multiple sclerosis is relapsing-remitting multiple sclerosis or secondary-progressive multiple sclerosis.

10. The method of claim 9, wherein the subject is a woman.

11. The method of claim 1, wherein, prior to administering the estrogen receptor beta ligand, the subject is receiving an immunotherapeutic agent or an anti-inflammatory agent.

12. The method of claim 11, wherein the immunotherapeutic agent is selected from interferon-beta 1a, interferon-beta 1b, pegylated interferon-beta-1a, glatiramer acetate, natalizumab, mitoxantrone, fingolimod, teriflunomide, dimethyl fumarate, mycophenolate mofetil, paclitaxel, cyclosporine, corticosteroids, azathioprine, cyclophosphamide, methotrexate, cladribine, 4-aminopyridine, and tizanidine.

13. The method of claim 11, wherein evaluating the subject's brain gray matter comprises the steps of:
assessing the change in the gray matter volume of the subject's cerebral cortex over a period of time; and
administering an effective amount of an estrogen receptor beta ligand to the subject conjointly with the immunotherapeutic agent or the anti-inflammatory agent if the gray matter volume of the cerebral cortex decreases by at least 0.3 percent between a first assessment and a second assessment about 6 months after the first assessment, by at least 0.6 percent between a first assessment and a second assessment about one year after the first assessment, or by at least 1.0 percent between a first assessment and a second assessment about two years after the first assessment.

14. The method of claim 13, wherein the first assessment is performed before, at the same time as, or at about the same time as the first time the immunotherapeutic therapeutic agent or anti-inflammatory agent is administered.

15. The method of claim 13, wherein the second assessment is performed at least about six months, at least about one year, at least about 18 months, or at least about two years after said first assessment.

16. The method of claim 1, wherein after about 12 months of administration the subjects gray matter atrophy is less than 1.5%, less than 1.4%, less than 1.3%, less than 1.2%, less than 1.1%, less than 1.0%, less than 0.9%, less than 0.8%, less than 0.7%, less than 0.6%, or less than 0.5% as compared to the start of administration.

17. The method of claim 1, wherein the subject's gray matter atrophy is reduced by 3.5% as compared to a subject who has not been administered the estrogen receptor beta ligand.

18. The method of claim 1, wherein the estrogen receptor beta ligand is diarylpropionitrile.

19. The method of claim 1, wherein the multiple sclerosis is relapsing-remitting multiple sclerosis or secondary-progressive multiple sclerosis.

20. The method of claim 1, wherein the subject is a woman.

* * * * *